(12) United States Patent
Wu et al.

(10) Patent No.: US 7,452,892 B2
(45) Date of Patent: Nov. 18, 2008

(54) TRIAZOLOPYRIMIDINE CANNABINOID RECEPTOR 1 ANTAGONISTS

(75) Inventors: Gang Wu, Princeton, NJ (US); Amarendra B. Mikkilineni, Easton, PA (US); Philip M. Sher, Plainsboro, NJ (US); Natesan Murugesan, Princeton Junction, NJ (US); Zhengxiang Gu, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/455,083

(22) Filed: Jun. 16, 2006

(65) Prior Publication Data

US 2006/0287341 A1 Dec. 21, 2006

Related U.S. Application Data

(60) Provisional application No. 60/692,001, filed on Jun. 17, 2005.

(51) Int. Cl.
 *A61K 31/519* (2006.01)
 *A01N 43/90* (2006.01)
 *C07D 487/00* (2006.01)

(52) U.S. Cl. .................................... 514/259.5; 544/280
(58) Field of Classification Search .................. 544/280
See application file for complete search history.

(56) References Cited

U.S. PATENT DOCUMENTS

| | | | |
|---|---|---|---|
| 3,674,836 A | 7/1972 | Creger |
| 3,983,140 A | 9/1976 | Endo et al. |
| 4,027,009 A | 5/1977 | Grier et al. |
| 4,231,938 A | 11/1980 | Monaghan et al. |
| 4,346,227 A | 8/1982 | Terahara et al. |
| 4,379,785 A | 4/1983 | Weyer et al. |
| 4,448,784 A | 5/1984 | Glamkowski et al. |
| 4,450,171 A | 5/1984 | Hoffman et al. |
| 4,499,289 A | 2/1985 | Baran et al. |
| 4,613,610 A | 9/1986 | Wareing |
| 4,639,436 A | 1/1987 | Junge et al. |
| 4,647,576 A | 3/1987 | Hoefle et al. |
| 4,681,893 A | 7/1987 | Roth |
| 4,686,237 A | 8/1987 | Anderson |
| 4,759,923 A | 7/1988 | Buntin et al. |
| 4,871,721 A | 10/1989 | Biller |
| 4,904,769 A | 2/1990 | Rauenbusch |
| 4,924,024 A | 5/1990 | Biller |
| 5,011,930 A | 4/1991 | Fujikawa et al. |
| 5,177,080 A | 1/1993 | Angerbauer et al. |
| 5,260,440 A | 11/1993 | Hirai et al. |
| 5,273,995 A | 12/1993 | Roth |
| 5,354,772 A | 10/1994 | Kathawala |
| 5,385,929 A | 1/1995 | Bjorge et al. |
| 5,447,954 A | 9/1995 | Gribble et al. |
| 5,488,064 A | 1/1996 | Sher |
| 5,491,134 A | 2/1996 | Sher et al. |

(Continued)

FOREIGN PATENT DOCUMENTS

DE 196 22 222 12/1997

(Continued)

OTHER PUBLICATIONS

Vippagunta et. al., Advanced Drug Delivery Reviews, 48 (2001) 3-26.*

(Continued)

*Primary Examiner*—James Wilson
*Assistant Examiner*—Jeffrey H Murray
(74) *Attorney, Agent, or Firm*—Rosemary M. Miano; Maureen S. Gibbons

(57) ABSTRACT

The present application describes compounds according to both Formulas I and II, pharmaceutical compositions comprising at least one compound according to either Formula I or II and optionally one or more additional therapeutic agents, and methods of treatment using the compounds according to Formulas I and II both alone and in combination with one or more additional therapeutic agents. The compounds have the following general formulas:

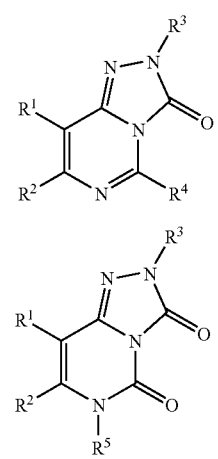

including all prodrugs, solvates, pharmaceutically acceptable salts and stereoisomers, wherein $R^1$, $R^2$, $R^3$, $R^4$ and $R^5$ are described herein.

3 Claims, No Drawings

U.S. PATENT DOCUMENTS

| | | | |
|---|---|---|---|
| 5,506,219 | A | 4/1996 | Robl |
| 5,541,204 | A | 7/1996 | Sher et al. |
| 5,594,016 | A | 1/1997 | Ueno et al. |
| 5,612,359 | A | 3/1997 | Murugesan |
| 5,686,104 | A | 11/1997 | Mills et al. |
| 5,691,322 | A | 11/1997 | Robl |
| 5,698,527 | A | 12/1997 | Kim |
| 5,712,396 | A | 1/1998 | Magnin et al. |
| 5,753,675 | A | 5/1998 | Wattanasin |
| 5,770,615 | A | 6/1998 | Cheng et al. |
| 5,776,983 | A | 7/1998 | Washburn et al. |
| 5,990,109 | A | 11/1999 | Chen et al. |
| 6,043,265 | A | 3/2000 | Murugesan et al. |
| 6,184,231 | B1 | 2/2001 | Hewawasam et al. |
| 6,414,002 | B1 | 7/2002 | Cheng et al. |
| 6,528,512 | B1 | 3/2003 | Gallagher et al. |
| 6,635,626 | B1 | 10/2003 | Barrish et al. |
| 6,737,085 | B2 * | 5/2004 | Nishibe et al. ............. 424/725 |
| 2004/0063580 | A1 | 4/2004 | Kuragano et al. |

FOREIGN PATENT DOCUMENTS

| | | |
|---|---|---|
| EP | 0 142 146 | 5/1985 |
| EP | 0 221 025 | 5/1987 |
| EP | 0 675 714 | 10/1995 |
| EP | 0 818 448 | 1/1998 |
| EP | 0 992 496 | 4/2000 |
| EP | 1 022 272 | 7/2000 |
| EP | 1 333 031 | 8/2003 |
| FR | 2 596 393 | 10/1987 |
| GB | 1 291 417 | 10/1972 |
| GB | 2 205 837 | 12/1988 |
| GB | 2 304 106 | 3/1997 |
| WO | WO 86/03488 | 6/1986 |
| WO | WO 86/07054 | 12/1986 |
| WO | WO 94/15592 | 7/1994 |
| WO | WO 97/21993 | 6/1997 |
| WO | WO 97/35576 | 10/1997 |
| WO | WO 97/48701 | 12/1997 |
| WO | WO 99/00353 | 1/1999 |
| WO | WO 00/01389 | 1/2000 |
| WO | WO 00/15201 | 3/2000 |
| WO | WO 00/30665 | 6/2000 |
| WO | WO 00/38722 | 7/2000 |
| WO | WO 00/39077 | 7/2000 |
| WO | WO 00/50574 | 8/2000 |
| WO | WO 2004/009560 | 1/2004 |
| WO | WO2005/049615 | 6/2005 |
| WO | WO2005/063761 | 7/2005 |
| WO | WO2005/063762 | 7/2005 |

OTHER PUBLICATIONS

Muccioli, G.G. ; Lambert, D.M., "Latest advances in cannabinoid receptor antagonists and inverse agonists", Expert Opin. Ther. Patents, vol. 16(10), pp. 1405-1423 (2006).

Aranyos, A. et al., "Novel Electron-Rich Bulky Phosphine Ligands Facilitate the Palladium-Catalyzed Preparation of Diaryl Ethers", J. Am. Chem. Soc., vol. 121, pp. 4369-4378 (1999).

Biller, Scott et al., "Squalene Synthase Inhibitors", Current Pharmaceutical Design, vol. 2, pp. 1-40 (1996).

Biller, Scott et al., "Isoprenoid (Phosphinylmethyl) phosphonates as Inhibitors of Squalene Synthetase", J. of Medicinal Chemistry, vol. 31(10), pp. 1869-1871 (1988).

Brown, D.J., "Pyrimidines and their Benzo Derivatives", Comprehensive Heterocyclic Chemistry, vol. 3, Part 2B, pp. 57-142 (1984).

Buback, M. et al., "Diastereoselectivity and Kinetics of Intermolecular Hetero Diels-Alder Reactions under High Pressure. A Significant Pressure-Induced Increase in Stereoselectivity", Chem. Ber., vol. 122, pp. 1179-1186 (1989).

Capson, T.L., "Synthesis and Evaluation of Ammonium Analogs of Carbocationic Intermediates in Squalene Biosynthesis", Dissertation, Dept Med Chem U of Utah, Abstract, Table of Contents, pp. 16, 17, 40-43,48-51, Summary (1987).

Cocco, M.T. et al., "1,2,4-Triazolo[4,3-c] From 4-Acylhydrazinopyrimidines", J. Heterocyclic Chem, vol. 29, pp. 1341-1347 (1992).

Colombo, G. et al., "Appetite Suppression and Weight Loss after the Cannabinoid Antagonist SR 141716", Life Sciences, vol. 63(8), pp. 113-117 (1998).

Corey, E.J. et al., "Application of Unreactive Analogs of Terpenoid Pyrophosphates to Studies of Multistep Biosynthesis. Demonstration that "Presqualene Pyrophosphate" is an Essential Intermediate on the Path to Squalene"J. of Amer. Chem. Soc., vol. 98(5), pp. 1291-1293 (1976).

DiMarzo, V. et al., "Leptin-regulated endocannabinoids are involved in maintaining food intake" Nature, vol. 410, pp. 822-825 (2001).

Erian, A.W., "The Chemistry of β-Enaminonitriles as Versatile Reagents in Heterocyclic Synthesis", Chem. Rev., vol. 93, pp. 1991-2005 (1993).

Galiegue, S. et al., "Expression of central and peripheral cannabinoid receptors in human immune tissues and leukocyte subpopulations", Eur. J. Biochem., vol. 232, pp. 54-61 (1995).

Ghiselli, G., "The Pharmacological Profile of FCE 27677: A Novel ACAT Inhibitor with Potent Hypolipidemic Activity Mediated by Selective Suppression of the Hepatic Secretion of ApoB-100-Containing Lipoprotein", Cardiovascular Drug Reviews, vol. 16(1), pp. 16-30 (1998).

Glass, M., et al., "Cannabinoid Receptors in the Human Brain: A Detailed Anatomical and Quantitative Autoradiographic Study in the Fetal, Neonatal and Adult Human Brain", Neuroscience, vol. 77(2), pp. 299-318 (1997).

Groziak, M.P., "Six-Membered Ring Systems: Diazines and Benzo Derivatives", Progress in Heterocyclic Chemistry, vol. 8, pp. 231-254 (1996).

Groziak, M.P., "Six-Membered Ring Systems: Diazines and Benzo Derivatives", Progress in Heterocyclic Chemistry, vol. 15, pp. 306-338 (2003).

Hamann, B.C. et al., "Sterically Hindered Chelating Alkyl Phosphines provide large rate accelerations in Palladium-Catalyzed Amination of Aryl Iodides, Bromides and Chlorides, and the First Amination of Aryl Tosylates", J. Am. Chem. Soc., vol. 120, pp. 7369-7370 (1998).

Hara, S., "Ileal Na+/bile acid cotransporter inhibitors", Drugs of the Future, vol. 24(4), pp. 425-430 (1999).

Heinisch, G. et al., "Six-Membered Ring Systems: Diazines and Benzo Derivatives", Progress in Heterocyclic Chemistry, vol. 7, pp. 226-243 (1995).

Hildebrandt, A. et al., "Antiobesity effects of chronic cannabinoid $CB_1$ receptor antagonist treatment in diet-induced obese mice", Eur. J. of Pharmacology, vol. 462, pp. 125-132 (2003).

Hojo, M. et al., "O-N, S-N and N-N exchange reactions at olefinic carbon atoms: Facile Synthetic Method for β-Trifluoroacetylvinylamines", Tetrahedron Letters, vol. 30(45), pp. 6173-6176 (1989).

Hollenbaugh, D. et al., "The human T cell antigen gp39, a member of the TNF gene family, is a ligand for the CD40 receptor: expression of a soluble form of gp39 with B cell co-stimulatory activity", The EMBO Journal, vol. 11(12) pp. 4313-4321 (1992).

Hollenbaugh, D. et al., "Cleavable CD40lg fusion proteins and the binding to sgp39", J. of Immunological Methods, vol. 188, pp. 1-7 (1995).

Katritzky, A. et al., "The Mechanisms of Heterocyclic Ring Closures", Tetrahedron, vol. 43(22), pp. 5171-5186 (1987).

Krause, B.R., et al., "ACAT Inhibitors: Physiologic Mechanisms for Hypolipidemic and Anti-Atherosclerotic Activities in Experimental Animals", Inflammation :Mediators and Pathways, pp. 173-198 (1995).

Kress, T. et al., "Six-membered Ring Systems: Diazines & Benzo Derivatives", Progress in Heterocyclic Chemistry, vol. 4, pp. 186-203 (1992).

Kress, T. et al., "Six-membered Ring Systems: Diazines and Benzo Derivatives", Progress in Heterocyclic Chemistry, vol. 3, pp. 205-222 (1991).

Ljung, B. et al., "AZ 242, a novel PPARα/γ agonist with beneficial effects on insulin resistance and carbohydrate and lipid metabolism in ob/ob mice and obese Zucker rats", J. of Lipid Research, vol. 43, pp. 1855-1863 (2002).

Matsuda, L. et al., "Structure of a cannabinoid receptor and functional expression of the cloned cDNA", Letters to Nature, vol. 346, pp. 561-564 (1990).

McClard, R. et al., "Novel Phophonylphosphinyl (P-C-P-C-) Analogues of Biochemically interesting Diphosphates. Syntheses and Properties of P-C-P-C- Analogues of Isopentenyl Diphosphate and Dimethylallyl Disphosphate", J. Am. Chem. Soc., vol. 109, pp. 5544-5545 (1987).

Moreland, L. et al., "Treatment of Rheumatoid Arthritis with a Recombinant Human Tumor Necrosis factor receptor (p75)-Fc Fusion Protein", The New England J. of Medicine, vol. 337(3), pp. 141-147 (1997).

Munro, S. et al., "Molecular characterization of a peripheral receptor for cannabinoids", Nature, vol. 365, pp. 61-65 (1993).

Negri, G. et al., "Recent Development in Preparation Reactivity and Biological Activity of Enaminoketones and Enaminothiones and Their Utilization to Prepare Heterocyclic Compounds", J. Heterocyclic Chem., vol. 41, pp. 461-491 (2004).

Nicolai, E. et al., "Synthesis and SAR Studies of Novel Triazolopyrimidine Derivatives as Potent, Orally Active Angiotensin II Receptor Antagonists", J. Med. Chem., vol. 37, pp. 2371-2386 (1994).

Nicolosi, R. et al., "The ACAT inhibitor, CI-1011 is effective in the prevention and regression of aortic fatty streak area in hamsters", Atherosclerosis, vol. 137, pp. 77-85 (1998).

Ortiz de Montellano, P. et al., "Inhibition of Squalene Synthetase by Farnesyl Pyrophosphate Analogues", J. of Medicinal Chemistry, vol. 20(2), pp. 243-249 (1977).

Rosenblum, S. et al., "Discovery of 1-(4-Fluorophenyl)-(3R)-[3-(4-fluorophenyl)-(3S)-hydroxypropyl]-(4S)-(4-hydroxyphenyl)-2-azetidinone (SCH 58235): A Designed, Potent, Orally Active Inhibitor of Cholesterol Absorption", J. Med. Chem., vol. 41, pp. 973-980 (1998).

Rowland, N. et al., "Effects of the cannabinoid receptor antagonist SR 141716, alone and in combination with dexfenfluramine or naloxone, on food intake in rats", Psychopharmacology, vol. 159, pp. 111-116 (2001).

Salisbury, B. et al., "Hypocholesterolemic activity of a novel inhibitor of cholesterol absorption, SCH 48461", Atherosclerosis, vol. 115, pp. 45-63 (1995).

Sliskovic, D. et al., "ACAT Inhibitors: Potential Anti-atherosclerotic Agents", Current Medicinal Chemistry, vol. 1, pp. 204-225 (1994).

Stout, David M., "Inhibitors of Acyl-CoA: Cholesterol O-Acyl Transferase (ACAT) as Hypocholesterolemic Agents. 6. The First Water-Soluble ACAT Inhibitor with Lipid-regulating Activity Inhibitors of Acyl-CoA: Cholesterol Acyltransferase (ACAT). 7. Development of a Series of Substituted N-Phenyl-N-[(1-phenylcyclopentyl)-Hypocholestrolemic Activity", Chemtracts-Organic Chemistry, vol. 8, pp. 359-362 (1995).

Smith, C. et al., "RP 73163: A Bioavailable Alkylsulphinyl-Diphenylimidazole ACAT Inhibitor", Bioorganic & Medicinal Chemistry Letters, vol. 6(1), pp. 47-50 (1996).

Sorbera, L. et al., "Treatment of Lipoprotein Disorders", Avasimibe, Drugs of the Future, vol. 24(1), pp. 9-15 (1999).

Takahashi, M. et al., "Synthesis of 3-Substituted 5, 6-Diphenylpyrimidin-4-Ones from Diphenylcyclopropenone and N-Substituted Amide Oximes", Heterocycles, vol. 22(3), pp. 581-584 (1984).

Temple, Jr. C. et al., "The Preparation of 9-Amino-9H-purines. II. 9-Amino-6-chloro-9H-purin-8(7H)-one", The J. of Organic Chemistry, vol. 33(2), pp. 530-533 (1968).

Tominaga, Y. et al., "Synthesis of Pyrimidine Derivatives and Their Related Compounds using Ketene Dithioacetals", Heterocycles, vol. 29(7), pp. 1409-1429 (1989).

Trillou, C.R., et al., "Anti-obesity effect of SR141716, a CB1 receptor antagonist, in diet-induced obese mice", Am.J. Physiol Regul Integr Comp Physiol., vol. 284, pp. R345-R353 (2003).

Undheim, K. et al., "Pyrimidines and their Benzo Derivatives", Comprehensive Heterocyclic Chemistry II, vol. 6, pp. 93-232 (1996).

Von Angerer, S., "Produce Class 12: Pyrmidines", Science of Synthesis, vol. 16, pp. 379-572 (2004).

Williams, C. et al., "Anandamide induces overeating: mediation by central cannabinoid (CB1) receptors", Psychopharmacology, vol. 143, pp. 315-317 (1999).

Yajima, K. et al., "Combination therapy with PPARγ and PPARα agonists increases glucose-stimulated insulin secretion in db/db mice" Am. J. Physiol. Endocrinol. Metab., vol. 284, pp. E966-E971 (2003).

Seada, M. et al., "Synthesis and Biological Activities of Some New Pyrimidine Derivatives", Asian J. of Chemistry, vol. 4(3), pp. 544-552 (1992).

Katoch-Rouse et al., Journal of Medicinal Chemistry, vol. 46, pp. 642-645, 2003.

Krishnamurthy et al., Biorganic & Medicinal Chemistry, vol. 12, pp. 393-404, 2004.

Mussinu et al., Bioorganic & Medicinal Chemistry, vol. 11, pp. 251-263, 2003.

Pagotto et al., Endocrine Reviews, vol. 27, No. 1, pp. 73-100, 2006.

* cited by examiner

TRIAZOLOPYRIMIDINE CANNABINOID RECEPTOR 1 ANTAGONISTS

RELATED APPLICATION

This application claims priority benefit under Title 35 § 119(e) of U.S. Provisional Application No. 60/692,001, filed Jun. 17, 2005, the contents of which are herein incorporated by reference.

BACKGROUND

Delta-9-tetrahydrocannabinol or Delta-9 THC, the principle active component of Cannabis sativa (marijuana), is a member of a large family of lipophilic compounds (i.e., cannabinoids) that mediate physiological and psychotropic effects including regulation of appetite, immunosuppression, analgesia, inflammation, emesis, anti-nocioception, sedation, and intraocular pressure. Other members of the cannabinoid family include the endogenous (arachidonic acid-derived) ligands, anandamide, 2-arachidonyl glycerol, and 2-arachidonyl glycerol ether. Cannabinoids work through selective binding to and activation of G-protein coupled cannabinoid receptors. Two types of cannabinoid receptors have been cloned including CB-1 (L. A. Matsuda, et al., *Nature*, 346, 561-564 (1990)), and CB-2 (S. Munro, et al., *Nature*, 365, 61-65 (1993)). The CB-1 receptor is highly expressed in the central and peripheral nervous systems (M. Glass, et al., *Neuroscience*, 77, 299-318 (1997)), while the CB-2 receptor is highly expressed in immune tissue, particularly in spleen and tonsils. The CB-2 receptor is also expressed on other immune system cells, such as lymphoid cells (S. Galiegue, et al., *Eur J Biochem*, 232, 54-61 (1995)). Agonist activation of cannabinoid receptors results in inhibition of cAMP accumulation, stimulation of MAP kinase activity, and closure of calcium channels.

There exists substantial evidence that cannabinoids regulate appetitive behavior. Stimulation of CB-1 activity by anandamide or Delta-9 THC results in increased food intake and weight gain in multiple species including humans (Williams and Kirkham, *Psychopharm.*, 143, 315-317 (1999)). Genetic knock-out of CB-1 result in mice that were hypophagic and lean relative to wild-type litter mates (DiMarzo, et al., *Nature*, 410, 822-825 (2001)). Published studies with CB-1 small molecule antagonists have demonstrated decreased food intake and body weight in rats (Trillou, et. al., *Am. J. Physiol. Regul. Integr. Comp. Physiol.*, R345-R353, (2003)). Chronic administration of the CB-1 antagonist AM-251 for two weeks resulted in substantial body weight reduction and decreased adipose tissue mass (Hildebrandt, et. al., *Eur. J. Pharm*, 462, 125-132 (2003)). There are multiple studies that have assessed the anorexic effect of the Sanofi CB-1 antagonist, SR-141716 (Rowland, et. al., *Pyschopharm.*, 159, 111-116 (2001); Colombo, et. al., *Life Sci.*, 63, 113-117 (1998)). There are at least two CB-1 antagonists in clinical trials for regulation of appetite, Sanofi's SR-141716 and Solvay's SLV-319. Published Phase IIb data reveal that SR-141716 dose-dependently reduced body weight in human subjects over a 16 week trial period. CB-1 antagonists have also been shown to promote cessation of smoking behavior. Phase II clinical data on smoking cessation were presented in September of 2002 at Sanofi-Synthelabo's Information meeting. This data showed that 30.2% of patients treated with the highest dose of SR-141716 stayed abstinent from cigarette smoke relative to 14.8% for placebo.

DETAILED DESCRIPTION

The present application describes compounds according to Formulas I and II, pharmaceutical compositions comprising at least one compound according to Formulas I or II and optionally one or more additional therapeutic agents, and methods of treatment using the compounds according to Formulas I or II both alone and in combination with one or more additional therapeutic agents.

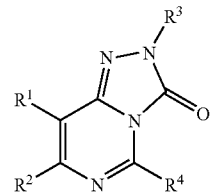

I

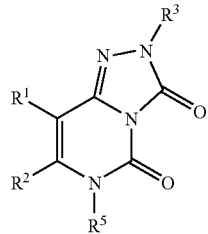

II including all prodrugs, solvates, pharmaceutically acceptable salts and stereoisomers, wherein $R^1$, $R^2$, $R^3$, $R^4$, and $R^5$ are described herein.

DEFINITIONS

The following definitions apply to the terms as used throughout this specification, unless otherwise limited in specific instances.

The term "alkyl" as employed herein, alone or as part of another group, includes saturated straight chain, branched chain, cyclic and bicyclic hydrocarbons, containing 1 to 20 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, cyclopropyl, cyclohexyl, norbornyl, and the like. The term "alkyl" as employed herein therefore encompasses cycloalkyl groups.

Unless otherwise indicated, the term "alkenyl" as used herein alone or as part of another group refers to straight chain, branched chain, cyclic and bicyclic hydrocarbons of 2 to 20 carbons, that include one or more double bonds, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, and 1-cyclohexenyl. The term "alkenyl" as employed herein therefore encompasses cycloalkenyl groups.

Unless otherwise indicated, the term "aryl" or "Ar" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one additional fused heterocyclic ring, for example:

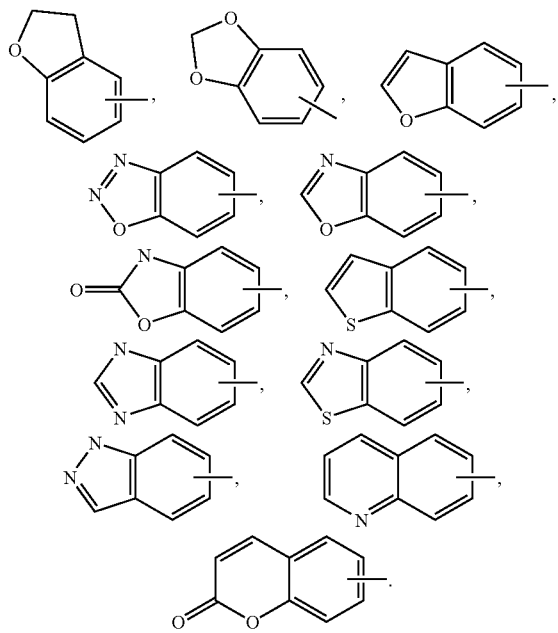

The term "arylalkyl" as used alone or as part of another group refers to an alkyl as defined herein, having an aryl substituent. Representative examples of arylalkyl include, but are not limited to, benzyl, 2-phenylethyl, 3-phenylpropyl, benzhydryl, naphthylmethyl, 4-trifluoromethylphenylpropyl and the like.

The term "halogen" or "halo" as used herein alone or as part of another group refers to chlorine, bromine, fluorine and iodine.

Unless otherwise indicated, the term "alkoxy" or "aryloxy" as employed herein alone or as part of another group refers to an alkyl or aryl group, as defined herein, linked to an oxygen atom.

Unless otherwise indicated, the term "heteroaryl" as used herein alone or as part of another group refers to a 5- or 6-membered aromatic ring which includes 1, 2, 3 or 4 heteroatoms such as nitrogen, oxygen or sulfur, and includes possible N-oxides. Heteroaryl groups may also contain a fused benzene ring. Examples of heteroaryl groups include the following:

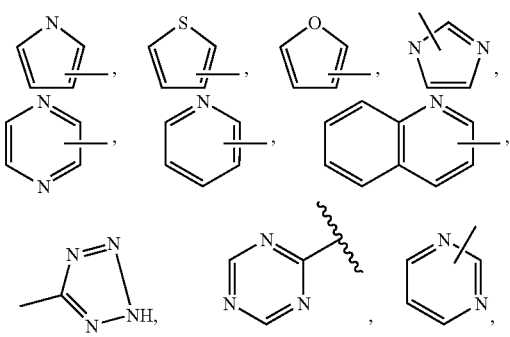

-continued

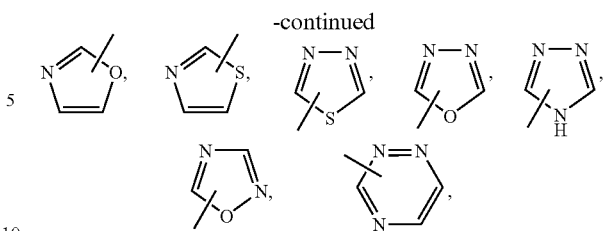

and the like.

As used herein, the term "heteroarylalkyl" means an alkyl group having a heteroaryl substituent.

Unless otherwise indicated, the term "heterocyclyl" as used herein alone or as part of another group refers to a 5- or 6-membered non-aromatic ring which includes 1, 2, 3 or 4 heteroatoms such as nitrogen, oxygen or sulfur, and includes possible N-oxides. Heterocyclyl groups may be saturated or monounsaturated. Examples of heterocyclyl groups include 4-morpholinyl, 3-piperidinyl, 2-tetrahydropyranyl, 3-tetrahydrothiophenyl, and the like.

It is understood that, where necessary, the valency of all atoms is made proper by the addition of hydrogens.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

All stereoisomers of the compounds of the instant invention are contemplated, either in mixture or in pure or substantially pure form. The compounds of the present invention can have asymmetric centers at any of the carbon atoms including those within any of the R substituents. Consequently, compounds of Formulas I and II can exist in enantiomeric or diastereomeric forms or in mixtures thereof. The processes for preparation can utilize racemates, enantiomers or diastereomers as starting materials. In order to prepare diastereomeric or enantiomeric products, conventional methods for isomer separation may be employed. These include, for example, chromatographic techniques, chiral HPLC, fractional crystallization, and sequences of derivatization, separation and de-derivatization.

It is anticipated that compounds of Formulas I and II can be prepared as prodrugs by one skilled in the art, and the definitions of Formulas I and II above include all prodrug, stereoisomers, atropisomers and pharmaceutically acceptable salts of Formulas I and II. Various forms of prodrugs are well known in the art. A comprehensive description of prodrugs and prodrug derivatives are described in:

*The Practice of Medicinal Chemistry*, Camille G. Wermuth et al., Ch 31, (Academic Press, 1996);

*Hydrolysis in Drug and Prodrug Metabolism*, Bernard Testa and Joachim M. Mayer, (Wiley-VCH, 2003);

*Design of Prodrugs*, edited by H. Bundgaard, (Elsevier, 1985);

*A Textbook of Drug Design and Development*, P. Krogsgaard-Larson and H. Bundgaard, eds. Ch 5, pgs 113-191 (Harwood Academic Publishers, 1991).

Said references are incorporated herein by reference.

Any compound that can be converted in vivo to provide the bioactive agent (i.e., the compound of Formula I or II) is a prodrug within the scope and spirit of the invention.

The compounds of Formulas I and II can be present as salts, which are also within the scope of this invention. Pharmaceutically acceptable (i.e., non-toxic, physiologically acceptable) salts are preferred. If the compounds of Formulas I and II have at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 8 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or such as benzoic acid, or with organic sulfonic acids, such as ($C_1$-$C_4$) alkyl or arylsulfonic acids which are unsubstituted or substituted, for example by halogen, for example methyl- or p-toluenesulfonic acid. Corresponding acid addition salts can also be formed having, if desired, an additionally present basic center. The compounds of Formulas I and II having at least one acid group (for example COOH) can form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethylpropylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of Formulas I and II or their pharmaceutically acceptable salts, are also included.

Preferred salts of the compounds of Formulas I and II which contain a basic group include monohydrochloride, hydrogen sulfate, methanesulfonate, phosphate, acetate and nitrate salts.

Preferred salts of the compounds of Formulas I and II which contain an acid group include sodium, potassium and magnesium salts and pharmaceutically acceptable organic amine salts.

The term "modulator" refers to a chemical compound with capacity to either enhance (e.g., "agonist" activity) or partially enhance (e.g., "partial agonist" activity) or inhibit (e.g., "antagonist" activity or inverse agonist activity) a functional property of biological activity or process (e.g., enzyme activity or receptor binding). Such enhancement or inhibition may be contingent on the occurrence of a specific event, such as activation of a signal transduction pathway, and/or may be manifest only in particular cell types.

The present invention provides compounds of Formulas I and II, pharmaceutical compositions employing such compounds and methods of using such compounds. In particular, the present invention provides for a pharmaceutical composition comprising a therapeutically effective amount of a compound of Formulas I or II alone or in combination with a pharmaceutically acceptable carrier.

Further, in accordance with the present invention, a method is provided for preventing, inhibiting or treating the progression or onset of diseases or disorders associated with the cannabinoid receptor, such as the diseases or disorders defined above and hereinafter, wherein a therapeutically effective amount of a compound of Formulas I or II is administered to a mammalian, i.e., human patient in need of treatment.

The compounds of the invention can be used alone, in combination with other compounds of the present invention, or in combination with one or more other agent(s) active in the therapeutic areas described herein.

In addition, a method is provided for preventing, inhibiting or treating the diseases as defined above and hereinafter, wherein a therapeutically effective amount of a combination of a compound of Formulas I or II and another compound of the invention and/or another type of therapeutic agent, is administered to a mammalian patient in need of treatment.

METHODS OF PREPARATION

The compounds of Formulas I and II of the invention can be prepared as shown below in the following reaction schemes, charts and descriptions thereof, as well as by using relevant published literature procedures that may be used by one skilled in the art. Exemplary reagents and procedures for these reactions appear hereinafter and in the working Examples.

The following abbreviations may be employed herein:

| | |
|---|---|
| min = | minute(s) |
| h = | hour(s) |
| L = | liter(s) |
| mL = | milliliter(s) |
| μL = | microliter(s) |
| g = | gram(s) |
| mg = | milligram(s) |
| mol = | mole(s) |
| M = | molar |
| mmol = | millimole(s) |
| HPLC = | high performance liquid chromatography |
| HPLC/MS or LC/MS = | high performance liquid chromatography/mass spectrometry |
| MS or Mass Spec = | mass spectrometry |
| [M + H]$^+$ = | parent plus a proton |
| [M + Na]$^+$ = | parent plus a sodium ion |
| [M − H]$^-$ = | parent minus a proton |
| Me = | methyl |
| Et = | ethyl |
| Ph = | phenyl |
| Bn = | benzyl |
| TMS = | trimethylsilyl |
| Ts = | p-toluenesulfonyl |
| Ac = | acetyl |
| THF = | tetrahydrofuran |
| TFA = | trifluoroacetic acid |
| EDC = | 1-[3-(dimethylamino)propyl]-3-ethylcarbodiimide hydrochloride |
| HOAt = | 1-hydroxy-7-azabenzotriazole |
| (BOC)$_2$O = | di-tert-butyl dicarbonate |
| mCPBA = | m-chloroperoxybenzoic acid |
| Ra-Ni = | Raney ® Nickel |
| LDA = | lithium diisopropylethylamide |
| pyr = | pyridine |
| DIBAl-H = | diisobutylaluminum hydride |
| PXPd = | bis[di-tert-butylphosphinous chloride-κP]di-μ-chlorodichloro-di-palladium |
| Pd$_2$(dba)$_3$ = | tris(dibenzylideneacetone)dipalladium |
| Pd(dppf)Cl$_2$•CH$_2$Cl$_2$ = | (1,1'-bis(diphenylphosphino)ferrocene)-palladium (II) chloride dichloromethane complex |
| dppf = | 1,1'-bis(diphenylphosphino)ferrocene |
| DEAD = | diethyl azodicarboxylate |
| NBS = | N-bromosuccinimide |
| NCS = | N-chlorosuccinimide |
| DMF = | N,N-dimethylformamide |
| DMSO = | dimethyl sulfoxide |
| EtOAc = | ethyl acetate |
| Et$_2$O = | diethyl ether = ether |
| PG = | any standard protecting group known to those |

-continued skilled in the art—see Protective Groups in Organic Synthesis (2nd Edition, T. W. Greene and P. G. M. Wuts, John Wiley & Sons, 1991)

Possible synthetic pathways for preparing the compounds of Formulas I and II are illustrated below through a series of retrosynthetic charts. For example, compounds of Formula I may be prepared from the immediate precursors shown in Chart 1. The compound labeling system employed in the retrosynthetic charts equates Formula I with "A". The immediate precursors of "A" in Chart 1 are "A1", "A2", "A3", "A4", "A5", "A11", and a subset of "B" in which $R^5$ is hydrogen (which is the same as a subset of "A31" in which Q is hydroxyl—see discussion of tautomers below). The compound labeling system employed in the retrosynthetic charts labels each compound as belonging to the "A series" or the "B series". Compounds such as I ("A") in which a carbonyl group is not present between the two pyrimidine nitrogen atoms belong to the "A series". Compounds such as II in which a carbonyl group is present in that position belong to the "B series". Thus, II is "B" itself. As shown in Chart 2, the immediate precursors of "B" are "B1", "B2", "B3", and "A3". Each of the immediate precursors of "A" and "B" are themselves the subject of unnumbered charts, as are the immediate precursors of each of those immediate precursors, and so on as generated by retrosynthetic analysis, which concludes when known or commercially available precursors are reached. Each precursor is labeled as a member of the "A series" or the "B series" according to its structure, as described above, with a label of the form "Annn . . . " or "Bnnn . . . " wherein "nnn . . . " is a sequence of 1 to 9 digits. While the vast majority of the retrosynthetic charts are unnumbered, they appear in an order determined by the subject (product) compound's label. The system used to order these charts is analogous to that used in a telephone book. Therefore, charts having as their product structure a member of the "A series" appear before those having as their product structure a member of the "B series". Furthermore, within each series, order is determined by evaluating the digits from left to right. The relative order of two charts is determined by the first point of difference (reading from left to right) in the subject compounds' labels. The chart having the subject compound's label with the lower digit at this first point of difference appears first. If there is no digit at the first point of difference, a zero is implied, and the chart with the subject compound's label having the implied zero appears first. Thus, for example, the following labels are placed in order: A11, A111, A11111111, A11321, A12, A3, A4, A411.

CHART 1

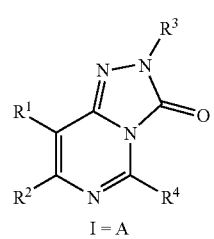

I = A

A CAN BE PREPARED FROM:

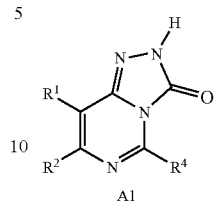

A1

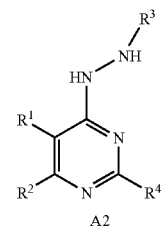

A2

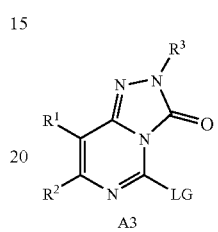

A3

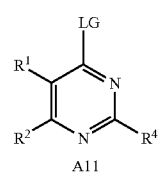

A11

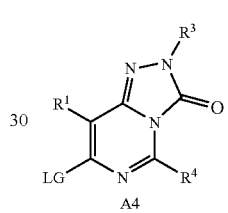

A4

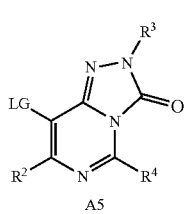

A5

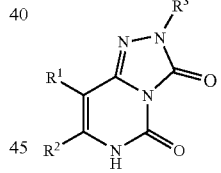

B with $R^5$ = H or
A31 with Q = OH

CHART 2

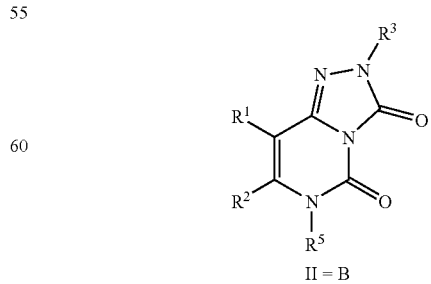

II = B

-continued

B CAN BE PREPARED FROM:

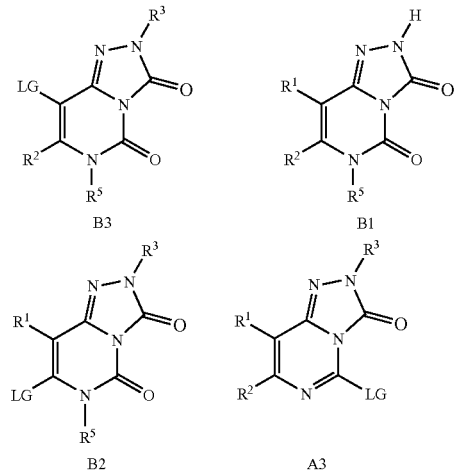

In the retrosynthetic charts and synthetic schemes and descriptions thereof, LG represents a leaving group, especially chloride, bromide, iodide, methanesulfonate, methanesulfinate, trifluoromethanesulfonate, p-toluenesulfonate, dinitrogen (as in a diazonium salt), phenoxide, and imidazolide, which is useful in nucleophilic displacement, electron transfer metallation, and/or palladium and other metal catalyzed coupling reactions. LG may also be trichloromethoxide or acetate or another carboxylic acid conjugate base when it is bonded to a carbonyl as, for example, in triphosgene, acetic anhydride or an organic mixed anhydride. LG may also be a hydroxyl, alkoxy, or amino group when it is bonded to a carbonyl and can be displaced by an intramolecular nucleophilic group. Where multiple LG appear in a single structure, they are independent of one another. For example, one LG may represent chloride and another may represent iodide. Furthermore, one LG may be changed into another LG prior to use in a displacement, metallation, or palladium or other metal catalyzed coupling reaction, for example replacement of chloride with iodide or replacement of dinitrogen (diazonium salt) with bromide.

In the retrosynthetic charts and synthetic schemes and descriptions thereof, Q represents a group that is a common precursor for a leaving group (LG) after one or two chemical steps. For example, Q may be a hydroxyl group because it can be converted to a chloride or a trifluoromethanesulfonate leaving group in one step. As another example, Q may be a methoxy group because it can be converted to a halogen or a sulfonate leaving group in two steps through the intermediacy of a hydroxyl group. As other examples, Q may be an amino group or a nitro group because they may be converted to a dinitrogen (diazonium salt) leaving group in one or two steps, respectively. As another example, Q may be a methylthio group because it can be converted to a methylsulfonyl group (which can leave as methanesulfinate) in one step. Where multiple Q appear in a single structure, they are independent of one another. For example, one Q may represent a hydroxyl group and another may represent an amino group.

In certain cases wherein Q represents a hydroxyl group, a tautomeric carbonyl structure is possible. See, for example, in Chart 1 "B in which $R^5$ is hydrogen" is a tautomer of "A31 in which Q is hydroxyl". While the manner in which a compound that can be represented by multiple tautomeric structures is drawn determines assignment to either the "A series" or the "B series", it is understood that tautomeric structures are chemically equivalent and represent the same compound. In general, tautomeric possibilities exist for compounds which can be drawn with a carbon atom both double bonded to a nitrogen atom and single bonded to the oxygen atom of a hydroxyl group. In the tautomer of this depiction, the carbon atom is double bonded to the oxygen atom and single bonded to the nitrogen atom, which bears a hydrogen atom. Typically, in tautomeric compounds represented in the retrosynthetic charts, the carbon and nitrogen atoms are within a ring.

In the retrosynthetic charts and synthetic schemes and descriptions thereof, some intermediates having a pyrimidine ring without a fused triazole ring have listed among their immediate precursors the expression "acyclic precursors" without a structure. This indicates that the subject intermediate of the chart may be prepared from known or commercially available compounds lacking the pyrimidine ring by chemistry in which the pyrimidine ring is formed using known methods such as those described in the following references and references contained therein:

G. Heinisch and B. Matuszczak, Progress in Heterocyclic Chemistry, volume 7, pp. 226-243, 1995;

M. P. Groziak, Progress in Heterocyclic Chemistry, volume 8, pp. 231-254, 1996;

M. P. Groziak, Progress in Heterocyclic Chemistry, volume 15, pp. 306-338, 2003;

T. J. Kress and D. L. Varie, Progress in Heterocyclic Chemistry, volume 4, pp. 186-203, 1992;

T. J. Kress and D. L. Varie, Progress in Heterocyclic Chemistry, volume 3, pp. 205-222, 1991;

A. W. Erian, Chemical Reviews, volume 93, pp. 1991-2005, 1993;

A. R. Katritzky, et al., Tetrahedron, volume 43, pp. 5171-5186, 1987;

G. Negri, et al., J. Heterocyclic Chem., volume 41, pp. 461-491, 2004;

Y. Tominaga, et al., Heterocycles, volume 29, pp. 1409-1429, 1989;

M. Takahashi, et al., Heterocycles, volume 22, pp. 581-584, 1984;

U.S. Pat. No. 6,528,512;

WO Patent Application 2004/009560;

S. von Angerer, Science of Synthesis, volume 16, pp. 379-572, 2004 (QD 262.535);

D. J. Brown, Comprehensive Heterocyclic Chemistry, volume 3, part 2B, pp. 57-142, 1984 (A. J. Boulton and A. McKillop, eds., Pergamon Press); and K. Undheim and T. Benneche, Comprehensive Heterocyclic Chemistry II, volume 6, pp. 93-232, 1996 (A. J. Boulton, ed., Pergamon Press).

Moreover, these references also describe methods for the manipulation of pyrimidine compound substituents, as required for many of the transformations represented in the retrosynthetic charts, such as the introduction of Q and LG groups by replacement of hydrogen, the conversion of one type of Q group into another, the conversion of Q groups into LG groups, the conversion of LG groups into R groups, and the conversion of one type of R group into another. Among the known methods for the introduction of Q groups by replacement of hydrogen are for example 1. nitration to introduce a nitro group and 2. deprotonation with a strong base followed by treatment with dimethyl disulfide to introduce a methylthio group or t-butyl hydroperoxide to introduce a hydroxyl group. Among the known methods for the introduction of LG groups by replacement of hydrogen are for example 1. deprotonation with a strong base followed by treatment with a halogen source such as molecular iodine and 2. electrophilic halogenation with molecular bromine. Among the known methods for the conversion of one type of Q group into another are for example 1. reduction of a nitro group to an amino group and 2. demethylation of a methoxy group to produce a hydroxyl group. Among the known methods for the conversion of Q groups into LG groups are for example 1. treatment with phosphorus oxychloride to convert a hydroxyl group into a chloride leaving group; 2. trifluoromethanesulfonylation to convert a hydroxyl group into a trifluoromethanesulfonate group; 3. diazotization to convert an amino group into a dinitrogen (diazonium salt) group; and 4. oxidation to convert a methylthio group into methylsulfonyl group (which can leave as methanesulfinate). Among the known methods for the conversion of LG groups into R groups are for example 1. nucleophilic displacement with alkoxides, aryloxides, and heteroaryloxides to introduce oxygen-linked R groups, with alkylamines, arylamines, and conjugate bases of NH-containing heterocycles to introduce nitrogen-linked R groups, with mercaptan salts to introduce sulfur-linked R groups, and with alkyl and aryl Grignard reagents and other organometallics, as well as cyanide, optionally followed by additional steps described below, to introduce carbon-linked R groups; 2. electron transfer metallation (optionally after deprotonation of any OH or NH groups with a base) followed by trapping of the resulting carbanion with an electrophilic form of R, such as R-LG, to introduce carbon-linked and sulfur-linked R groups; and 3. palladium and other metal catalyzed coupling reactions with organometallics such as $RB(OH)_2$, $RSnBu_3$, or RZnCl, to introduce aryl and heteroaryl R groups, with cyanide, optionally followed by additional steps described below, to introduce cyano, acyl, alkoxycarbonyl, arylcarbamoyl, and related carbon-linked R groups, and with alcohols, phenols and amines, to introduce oxygen-linked and nitrogen-linked R groups.

Furthermore, many of the same methods mentioned and referenced above that may be used to manipulate pyrimidine ring substituents in intermediates having a pyrimidine ring without a fused triazole ring may also be used to manipulate substituents in intermediates having a pyrimidine ring with a fused triazole ring (triazolopyrimidines).

Additional useful references, with useful references contained therein, that describe the synthesis and reactions of substituted triazolopyrimidine compounds include:

M. Seada, et al., Asian J. Chem., volume 4, pp. 544-552, 1992;

M. T. Cocco, et al., J. Heterocyclic Chem., volume 29, pp. 1341-1347, 1992;

C. Temple, Jr., et al., J. Org. Chem., volume 33, pp. 530-533, 1968; and

E. Nicolaï, et al., J. Med. Chem., volume 37, pp. 2371-2386, 1994.

Additional transformations that are represented in the retrosynthetic charts deserve comment.

Installation of $R^3$ onto the triazolopyrimidine core, for example in the preparation of "A" from "A1" in Chart 1 and in the preparation of "B" from "B1" in Chart 2, may be accomplished with $R^3$-LG by nucleophilic displacement or palladium catalyzed coupling methods, or when $R^3$ is alkyl and the like, it may also be accomplished by Mitsunobu reaction with $R^3$—OH or by opening of epoxide E1, so that $CR^{33}R^{34}CR^{35}R^{36}H=R^3$. This transformation presents a problem of N-derivatization vs. O-derivatization. Known methods that favor N-derivatization can be employed, for example, nucleophilic displacement reactions using a base with a counterion that coordinates oxygen, such as lithium.

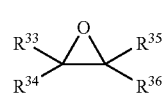

Intermediates such as "A1" (Chart 1), which have a triazolopyrimidine core but which lack $R^3$, may be prepared from pyrimidine intermediates such as "A11" ("A1" chart), which lack a fused triazole ring and which have a leaving group substituting the pyrimidine ring, by displacement of the leaving group with hydrazine, followed by reaction with 1,1'-carbonyldiimidazole, and thermal ring closure. Other examples of LG-CO-LG, such as phosgene, triphosgene, and phenyl chloroformate may be used in place of 1,1'-carbonyldiimidazole. Furthermore, reagents that contain both the hydrazine moiety and the carbonyl moiety ($H_2NNHCO$-LG) may be used to construct the triazole ring in a single operation. Such reagents include semicarbazide ($H_2NNHCONH_2$).

Triazolopyrimidines bearing an $R^3$ group, such as "A" (Chart 1), may also be prepared from pyrimidine intermediates such as "A11", which lack a fused triazole ring and which have a leaving group substituting the pyrimidine ring, by addition of a compound $H_2NNR^3CO$-LG, followed by intramolecular displacement of LG by a pyrimidine nitrogen to form the triazole ring. In this type of reaction LG may be, for example, an amino group. The compound $H_2NNR^3CO$-LG may be prepared by coupling PG-NHNHR$^3$, wherein PG is a protecting group such as t-butyloxycarbonyl, with LG-CO-LG, followed by deprotection. PG-NHNHR$^3$ may be prepared by protection of $H_2NNHR^3$ or by introduction of $R^3$ into PG-NHNH$_2$, for example by reductive alkylation of the primary amino group with $R^{31}COR^=$, so that $R^{31}R^{32}CH=R^3$, or nucleophilic displacement or palladium catalyzed coupling with $R^3$-LG.

As an alternative to the aforementioned method of addition of $H_2NNR^3CO$-LG with subsequent triazole ring closure, triazolopyrimidines bearing an $R^3$ group, may also be prepared from pyrimidine intermediates which lack a fused triazole ring and which have a leaving group substituting the pyrimidine ring, by addition of hydrazine, followed by treatment with 1,1'-carbonyldiimidazole, triphosgene, phenyl chloroformate, or other examples of LG-CO-LG, followed by introduction of $R^3$ with $R^3$-LG prior to triazole ring closure. This alternative method is exemplified in Scheme 1.

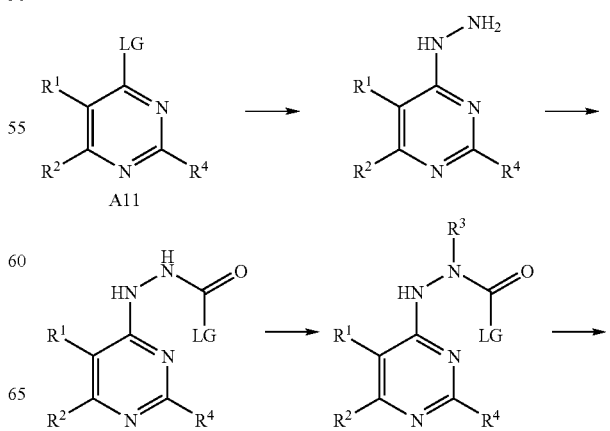

SCHEME 1

-continued

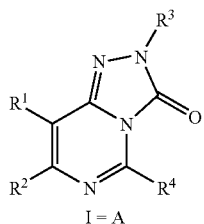

I = A

Triazolopyrimidines bearing an $R^3$ group, such as "A" (Chart 1), may be prepared from pyrimidine intermediates such as "A2", which have an $R^3$ substituted hydrazine moiety, by treatment with 1,1'-carbonyldiimidazole, phosgene, triphosgene, phenyl chloroformate, or other examples of LG-CO-LG, followed by triazole ring closure.

Pyrimidine intermediates such as "A2" (Chart 1), which have an $R^3$ substituted hydrazine moiety, may be prepared from pyrimidine intermediates such as "A11" ("A2" chart), which lack a fused triazole ring and which have a leaving group substituting the pyrimidine ring, by 1. addition of an $R^3$ substituted hydrazine, $H_2NNHR^3$; 2. addition of hydrazine, followed by reductive alkylation of the primary amino group with $R^{31}COR^{32}$, wherein $R^{31}R^{32}CH=R^3$, or nucleophilic displacement or palladium catalyzed coupling with $R^3$-LG; or 3. addition of trifluoroacetylhydrazine, followed by introduction of $R^3$ onto the trifluoroacetylated nitrogen by nucleophilic displacement with $R^3$-LG or by Mitsunobu reaction with $R^3$—OH, followed by hydrolytic removal of the trifluoroacetyl group.

According to the retrosynthetic charts, conversion of a Q group to an R group is generally a two-step process that involves the intermediacy of an LG group. However, certain oxygen-linked $R^1$, $R^2$, and $R^4$ groups may also be generated from a Q group without the intermediacy of an LG group when the Q group is a hydroxyl group. Generally, the hydroxyl group may be derivatized to produce the desired $R^1$, $R^2$, or $R^4$ group when it acts as the nucleophile in nucleophilic displacement, palladium catalyzed coupling, or Mitsunobu reactions. This process is represented in the retrosynthetic charts only where $R^4$ groups are derived from hydroxyl-containing precursors depicted in their tautomeric carbonyl forms. The following describes this.

In "A series" compounds, installation of a subset of $R^4$ groups which are O-linked to the triazolopyrimidine core may result not only from replacement of a leaving group with $R^4$, but also from O-derivatization of a "B series" compound in which $R^5$ is hydrogen. For example, the preparation of "A" (Chart 1), in which $R^4$ is benzyloxy may be accomplished by O-derivatization with benzyl bromide of a subset of "B" in which $R^5$ is hydrogen. More generally, the hydroxyl group may be derivatized to produce the desired $R^4$ group when it acts as the nucleophile in nucleophilic displacement, palladium catalyzed coupling, or Mitsunobu reactions. O-derivatization may be favored over competing N-derivatization by known methods. Likewise, this transformation is useful in the preparation of "A series" compounds having a pyrimidine ring without a fused triazole ring and having $R^4$ groups which are O-linked.

Intermediates in the "A series" having an O-linked leaving group substituting the carbon between the two pyrimidine nitrogens of the triazolopyrimidine core may also be prepared from a "B series" compound in which $R^5$ is hydrogen, for example by O-trifluoromethanesulfonylation, as for example in the preparation of "A3" from a subset of "B" in which $R^5$ is hydrogen ("A3" chart). Likewise, this type of transformation is useful in the preparation of "A series" compounds having a pyrimidine ring without a fused triazole ring and having an O-linked leaving group substituting the carbon between the two pyrimidine nitrogens.

Compounds in the "B series", such as "B" in Chart 2, wherein $R^5$ is hydrogen may be prepared from "A series" compounds, such as "A31" (Chart 2), which have a leaving group substituting the carbon between the two pyrimidine nitrogens, by hydrolysis, for example with lithium hydroxide, tetrabutylammonium hydroxide, or $(H_3C)_3SiOK$.

Many compounds in the "B series" wherein $R^5$ is not hydrogen may be prepared from the analogous "B series" compound in which $R^5$ is hydrogen by N-derivatization of the ring nitrogen with $R^5$-LG by nucleophilic displacement or palladium catalyzed coupling methods, or when $R^5$ is alkyl and the like, it may also be introduced by Mitsunobu reaction with $R^5$—OH. N-derivatization may be favored over competing O-derivatization of the carbonyl oxygen by using known methods that favor N-derivatization, for example by using a base with a counterion that coordinates oxygen, such as lithium, in nucleophilic displacement reactions.

According to the retrosynthetic charts, the introduction of an R group by replacement of hydrogen is generally a two-step process that involves the intermediacy of an LG group. However, certain carbon-linked and sulfur-linked $R^1$, $R^2$, and $R^4$ groups may also be installed by replacement of hydrogen without the intermediacy of an LG group by deprotonation with a strong base followed by trapping of the resulting carbanion with an electrophilic form of R, such as R-LG.

In the above descriptions of synthetic transformations the possible reagent lists are abbreviated, and it is understood that the reagents mentioned are example reagents, not meant to be limiting. Those skilled in the art will recognize that there are many acids (hydrochloric acid, polyphosphoric acid, etc.), many bases (sodium hydride, potassium methoxide, etc.), many oxidants (hydrogen peroxide, 3-chloroperoxybenzoic acid, Dess-Martin periodinane, etc.), many hydrogenation catalysts (palladium, platinum oxide, Raney® Nickel, etc.), and so on that may be employed to synthesize the compounds of the invention. In some cases alternative reagents known to those skilled in the art will be superior to those mentioned. Alternative reagents may be found in Reagents For Organic Synthesis (Fieser and Fieser, John Wiley & Sons) and Compendium of Organic Synthetic Methods (John Wiley & Sons). These references will also provide guidance in cases where the description herein designates only a class of reagent rather than a specific reagent (for example oxidant rather than hydrogen peroxide). In some instances the descriptions herein may refer not to specific reagents or reagent classes, but rather to name reactions, for example Curtius rearrangement (a. thionyl chloride b. sodium azide c. alkanol, heat; used for conversion of carboxyl groups to alkoxycarbonylamino groups). Name reactions and their experimental details are well-known to those skilled in the art—see Organic Syntheses Based on Name Reactions and Unnamed Reactions, A. Hassner and C. Stumer, Pergamon Press, 1994.

In general, the interchange of functional groups within the various R groups may be accomplished according to the methods and procedures described in Compendium of Organic Synthetic Methods (John Wiley & Sons), Comprehensive Organic Functional Group Transformations (Editors A. R. Katritzky, O. Meth-Cohn and C. W. Rees, Pergamon Press) and Comprehensive Organic Transformations—A Guide To Functional Group Preparations (R. C. Larock, VCH Publishers, 1989). For example, a compound of Formula I having a double bond in $R^1$ may be reduced by catalytic hydrogenation to produce a compound of Formula I that is saturated in $R^1$. As another example, an intermediate in which $R^2$ is a bromophenyl group may undergo palladium catalyzed coupling with an arylboronic acid to produce an intermediate in which $R^2$ is a biphenyl. As another example, an intermediate in which $R^3$ contains a hydroxyl group may be oxidized to produce an intermediate in which $R^3$ contains an oxo group. As another example, a compound of Formula I in which $R^4$ is an amino group may be alkylated with methyl iodide to produce a compound of Formula I in which $R^4$ is a methylamino group. As another example, a compound of Formula I in which $R^4$ is hydrogen may be deprotonated and alkylated with methyl iodide to produce a compound of Formula I in which $R^4$ is a methyl group. As another example, a compound of Formula II in which $R^5$ is hydrogen may be alkylated with benzyl bromide to produce a compound of Formula II in which $R^5$ is a benzyl group. As another example, a compound of Formula I in which $R^2$ is a methylthio group may be oxidized to produce a compound of Formula I in which $R^2$ is a methylsulfonyl group. As another example, a compound of Formula I in which $R^1$ is a methoxy group may be demethylated and carbamoylated to produce a compound of Formula I in which $R^1$ is a carbamoyloxy group. As another example, a compound of Formula I in which $R^2$ is an amino group may be phenylsulfonylated to produce a compound of Formula I in which $R^2$ is a phenylsulfonylamino group. As another example, a compound of Formula I in which $R^1$ is an ethoxycarbonyl group may be hydrolyzed to the corresponding carboxylic acid and made to undergo Curtius degradation to produce a compound of Formula I in which $R^1$ is an amino group. As another example, an intermediate in which $R^2$ is a cyano group may be hydrolyzed to the corresponding carboxylic acid and coupled with aniline to produce an intermediate in which $R^2$ is a phenylcarbamoyl group.

Generally, compounds of Formula I or II and synthetic intermediates in which an R group contains an aryl moiety substituted by cyano, alkyl, alkenyl, aryl, heteroaryl, alkoxy, aryloxy or any type of amino group may be prepared from the corresponding compounds of Formula I or II and synthetic intermediates wherein the aryl moiety is substituted by halo or hydroxy, using various palladium catalyzed coupling procedures as described in Aranyos, et al., J. Am. Chem. Soc. 1999, 121, 4369-4378 and Hamann, et al., J. Am. Chem. Soc. 1998, 120, 7369-7370 and references contained therein, and in recent papers authored by Gregory C. Fu, Stephen L. Buchwald, or John F. Hartwig. These procedures are directly applicable when the aryl moiety is substituted by halo. When the aryl moiety is substituted by hydroxy, prior activation by conversion of the hydroxyl group to a trifluoromethylsulfonyloxy group, as described in the aforementioned references, is required.

It is understood that during the course of manipulating any functional group within the various R groups of compounds of Formula I or II or at any stage of their synthesis, standard protecting groups, as described in Protective Groups in Organic Synthesis ($2^{nd}$ Edition, T. W. Greene and P. G. M. Wuts, John Wiley & Sons, 1991), may be employed to avoid undesired reactions of any other functional group.

The aforementioned retrosynthetic charts follow.

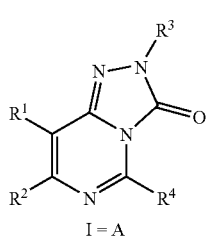

I = A

A CAN BE PREPARED FROM:

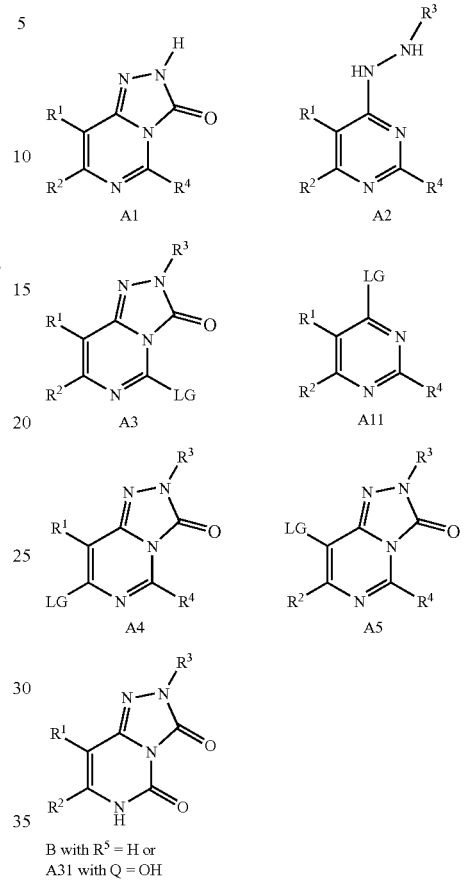

B with $R^5$ = H or
A31 with Q = OH

A1 CAN BE PREPARED FROM:

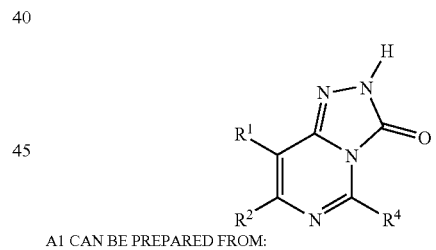

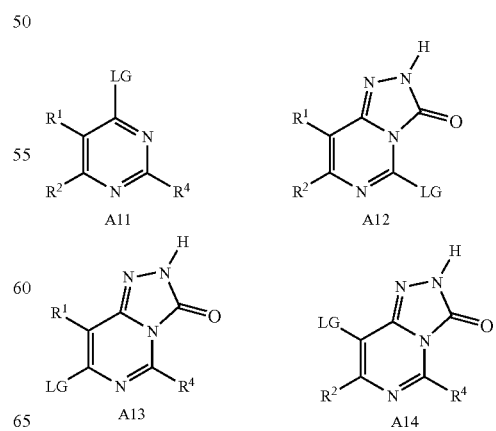

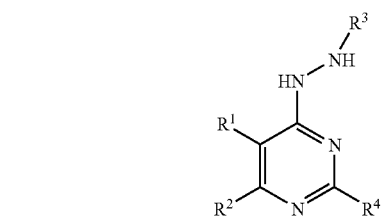
A2 CAN BE PREPARED FROM:
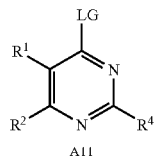
A11
A3 CAN BE PREPARED FROM:
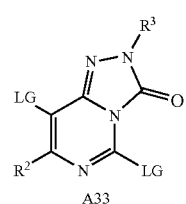 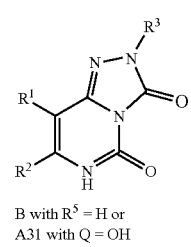
A33     B with $R^5$ = H or
            A31 with Q = OH
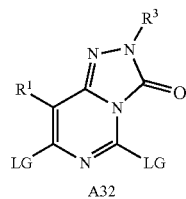 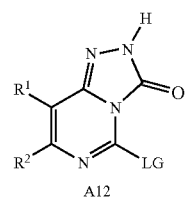
A32         A12
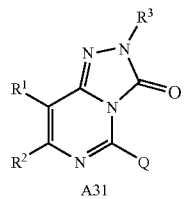 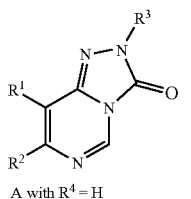
A31      A with $R^4$ = H
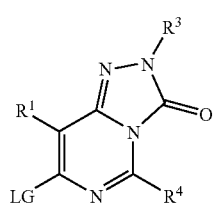
-continued
A4 CAN BE PREPARED FROM:
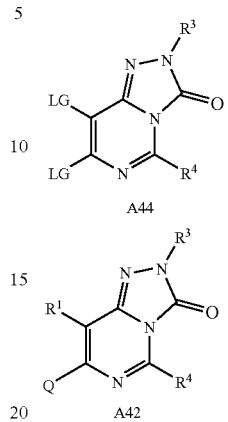 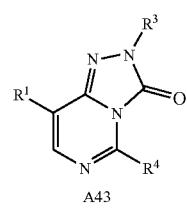
A44        A43
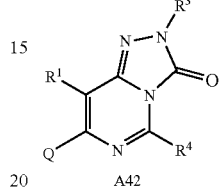 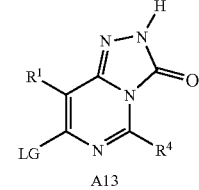
A42        A13
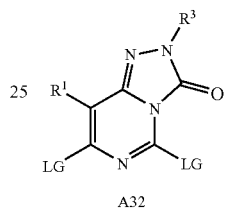 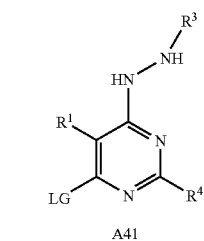
A32        A41
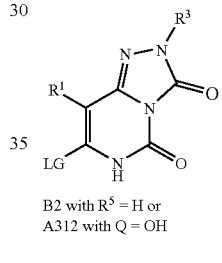 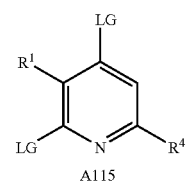
B2 with $R^5$ = H or     A115
A312 with Q = OH
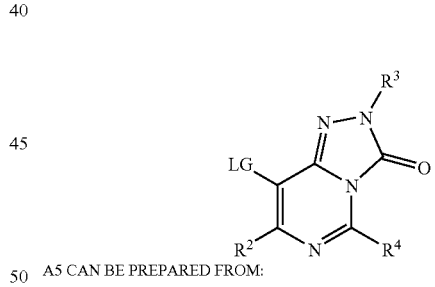
A5 CAN BE PREPARED FROM:
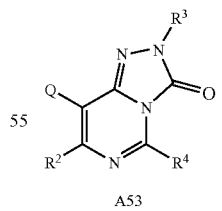 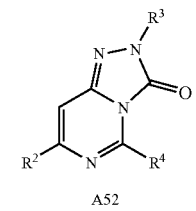
A53        A52
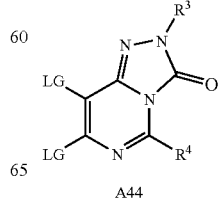 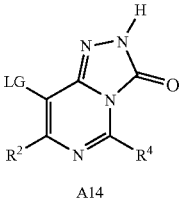
A44        A14

-continued
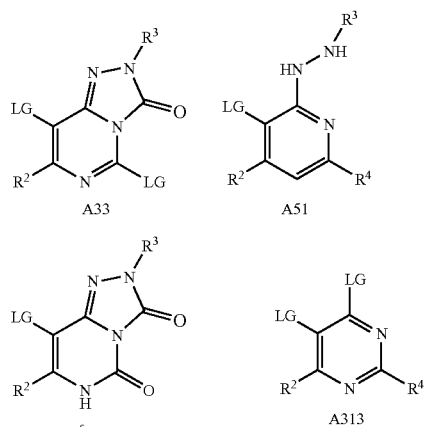
B3 with R⁵ = H or
A313 with Q = OH
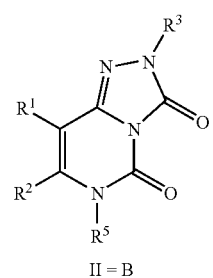
II = B
B CAN BE PREPARED FROM:
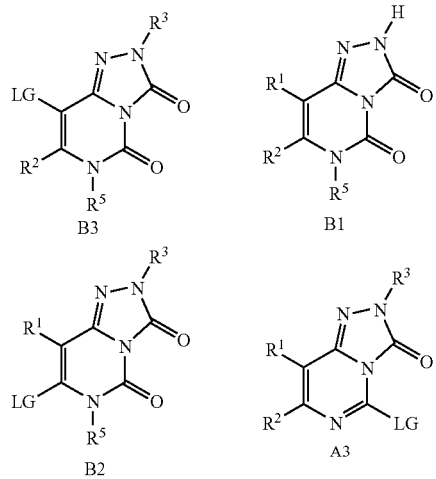
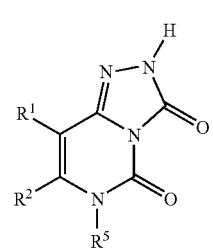
-continued
B1 CAN BE PREPARED FROM:
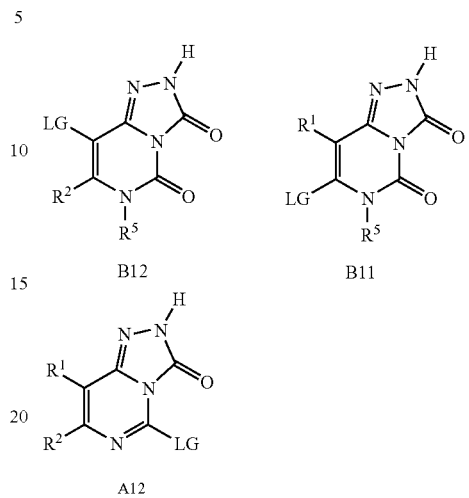
B2 CAN BE PREPARED FROM:
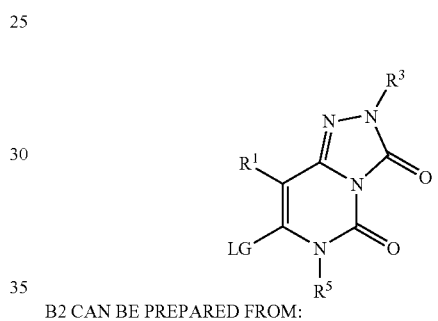
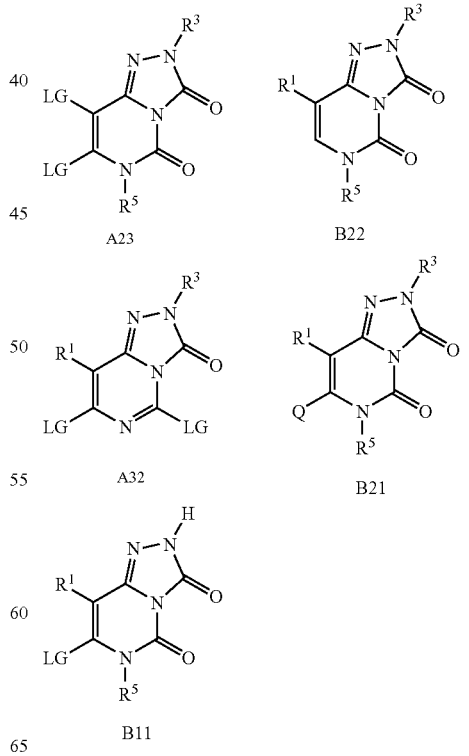

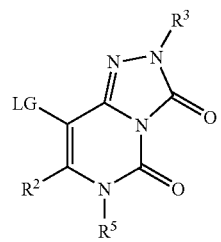

B3 CAN BE PREPARED FROM:

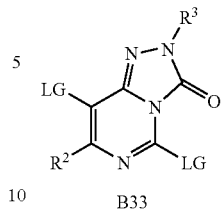

B33

The synthetic schemes below describe, in the forward synthetic direction and in greater detail, some of the more useful synthetic routes to compounds of Formulas I and II.

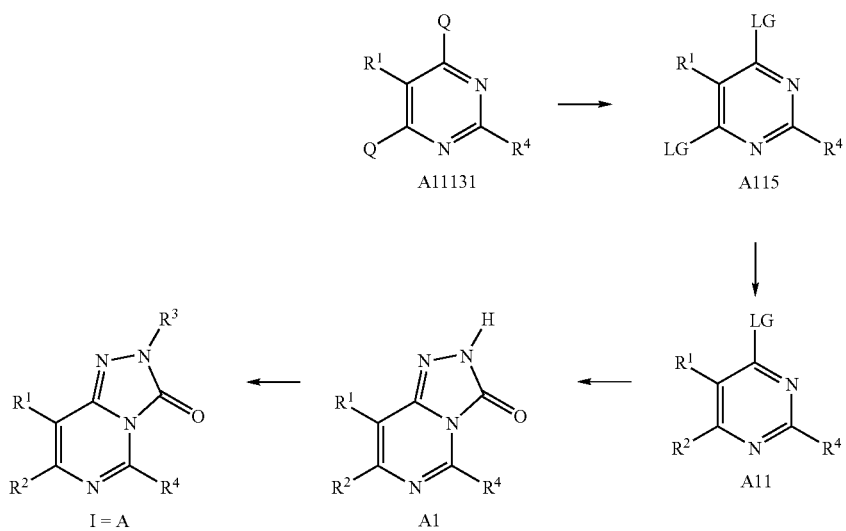

-continued

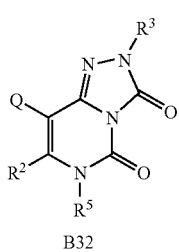

B32

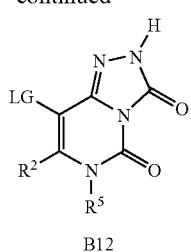

B12

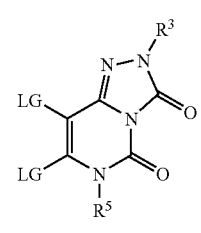

B31

B23

As shown in Scheme 2, a compound of Formula A11131, such as a 4,6-dihydroxypyrimidine, may be converted to a compound of Formula A115, such as a 4,6-dihalopyrimidine, for example, by reaction with a mixed anhydride of a hydrohalic acid, such as phosphorous oxychloride or phosphorus pentachloride or phosphorus oxybromide, optionally in a solvent, such as a chlorinated hydrocarbon, at an elevated temperature, such as 100° C., optionally in the presence of a substoichiometric amount of N,N-dimethylformamide, under an inert atmosphere, such as argon.

A compound of Formula A115, such as a 4,6-dihalopyrimidine, may be converted to a compound of Formula A11, such as a 6-aryl-4-halopyrimidine or a 6-heteroaryl-4-halopyrimidine, for example, by reaction with an $R^2$-containing organometallic reagent, such as an arylboronic acid or a heteroarylboronic acid or the pinacol ester of said boronic acids or an aryltrialkylstannane or a heteroaryltrialkylstannane, in a solvent, such as toluene or tetrahydrofuran or n-butanol or 1,4-dioxane or 1,2-dimethoxyethane or a mixture of solvents, such as tetrahydrofuran and methanol, at an elevated temperature, such as 200° C. or 120° C. or 80° C., achieved by either conventional or microwave heating, optionally in a sealed vessel to allow heating above the normal boiling point of the solvent, in the presence of a catalyst, such as a palladium catalyst, such as tetrakis(triphenylphosphine)palladium or (1,1'-bis(diphenylphosphino)ferrocene)-palladium (II) chloride dichloromethane complex or PXPd or a palladium catalyst—ligand combination, such as tris(dibenzylideneacetone)dipalladium with dicyclohexyl(2',6'-dimethoxybiphenyl-2-yl)phosphine, optionally in the presence of a base, such as anhydrous tribasic potassium phosphate or potassium carbonate or aqueous sodium carbonate or potassium carbonate solution, under an inert atmosphere, such as argon.

A compound of Formula A11, such as a 6-aryl-4-halopyrimidine, may be converted to a compound of Formula A1, such as a 7-aryl-[1,2,4]triazolo[4,3-c]pyrimidin-3(2H)-one, for example, by first nucleophilic displacement at the 4 position with hydrazine in a solvent, such as tetrahydrofuran or 1,4-dioxane or pyridine, at a temperature, such as ambient temperature or 65° C. or 120° C., under an inert atmosphere, such as argon, followed by treatment with a carbonylating agent, such as 1,1'-carbonyldiimidazole or triphosgene, in a solvent, such as tetrahydrofuran, at a temperature, such as ambient temperature or 60° C., under an inert atmosphere, such as argon.

A compound of Formula A1, such as a 7-aryl-[1,2,4]triazolo[4,3-c]pyrimidin-3(2H)-one, may be converted to a compound of Formula I, such as a 2-substituted 7-aryl-[1,2,4]triazolo[4,3-c]pyrimidin-3(2H)-one, for example, by reaction with an $R^3$-containing electrophile, $R^3$-LG, such as an optionally substituted benzyl halide or an optionally substituted heteroarylmethyl halide or an optionally substituted alkyl halide, in the presence of a base, such as potassium carbonate, in a solvent, such as N,N-dimethylformamide or acetone, at a temperature, such as ambient temperature or 55° C. or 80° C., under an inert atmosphere, such as argon; or by reaction with an $R^3$-containing alcohol, $R^3$—OH, such as an optionally substituted benzyl alcohol or an optionally substituted heteroarylmethyl alcohol or an optionally substituted alcohol, under Mitsunobu reaction conditions.

As shown in Scheme 3, a compound of Formula A113111, such as a 5-amino-4,6-dihalopyrimidine, may be converted to a compound of Formula A1331, such as a 8-amino-7-halo-[1,2,4]triazolo[4,3-c]pyrimidin-3(2H)-one, for example, by first nucleophilic displacement at the 4 position with hydrazine in a solvent, such as tetrahydrofuran or 1,4-dioxane or pyridine, at a temperature, such as ambient temperature or 65° C. or 120° C., under an inert atmosphere, such as argon, followed by treatment with a carbonylating agent, such as 1,1'-carbonyldiimidazole or triphosgene, in a solvent, such as tetrahydrofuran, at a temperature, such as ambient temperature or 60° C., under an inert atmosphere, such as argon.

A compound of Formula A1331, such as a 8-amino-7-halo-[1,2,4]triazolo[4,3-c]pyrimidin-3(2H)-one, may be converted to a compound of Formula A442, such as a 2-substituted 8-amino-7-halo-[1,2,4]triazolo[4,3-c]pyrimidin-3(2H)-one, for example, by reaction with an $R^3$-containing electrophile, $R^3$-LG, such as an optionally substituted benzyl halide or an optionally substituted heteroarylmethyl halide or an optionally substituted alkyl halide, in the presence of a base, such as potassium carbonate, in a solvent, such as N,N-dimethylformamide or acetone, at a temperature, such as ambient temperature or 55° C. or 80° C., under an inert atmosphere, such as argon; or by reaction with an $R^3$-containing alcohol, $R^3$—OH, such as an optionally substituted benzyl alcohol or an optionally substituted heteroarylmethyl alcohol or an optionally substituted alcohol, under Mitsunobu reaction conditions.

A compound of Formula A442, such as a 2-substituted 8-amino-7-halo-[1,2,4]triazolo[4,3-c]pyrimidin-3(2H)-one may be converted to a compound of Formula A44, such as a 2-substituted 7,8-dihalo-[1,2,4]triazolo[4,3-c]pyrimidin-3(2H)-one, for example, by reaction under diazotization conditions in the presence of a nucleophilic LG source, for example, by reaction with tertiary butyl nitrite and cupric

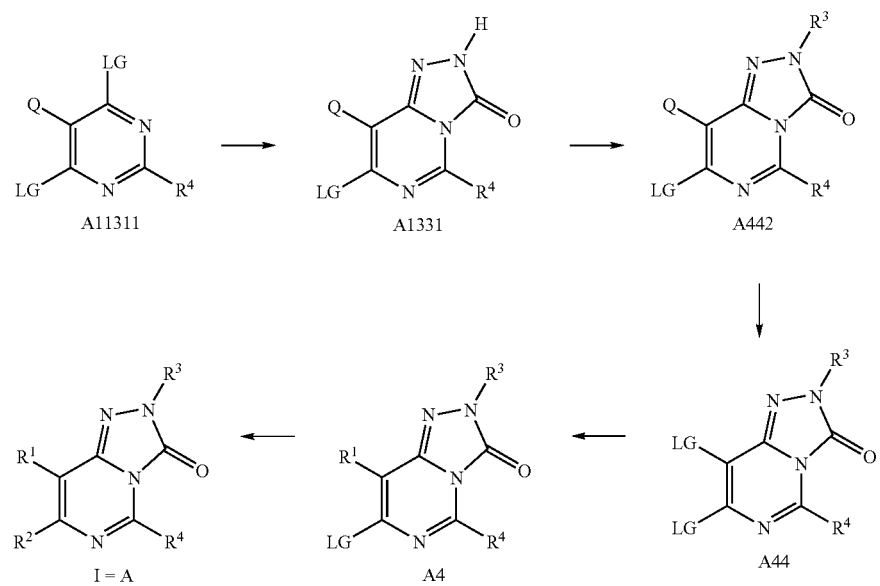

SCHEME 3 bromide in a solvent, such as acetonitrile, at a temperature, such as as ambient temperature or 65° C., under an inert atmosphere, such as argon.

A compound of Formula A44, such as a 2-substituted 7,8-dihalo-[1,2,4]triazolo[4,3-c]pyrimidin-3(2H)-one, may be converted to a compound of Formula A4, such as a 2-substituted 8-aryl-7-halo-[1,2,4]triazolo[4,3-c]pyrimidin-3(2H)-one or a 2-substituted 7-halo-8-heteroaryl-[1,2,4]triazolo[4,3-c]pyrimidin-3(2H)-one, for example, by reaction with an $R^1$-containing organometallic reagent, such as an arylboronic acid or a heteroarylboronic acid or the pinacol ester of said boronic acids or an aryltrialkylstannane or a heteroaryltrialkylstannane, in a solvent, such as toluene or tetrahydrofuran or n-butanol or 1,4-dioxane or 1,2-dimethoxyethane or a mixture of solvents, such as tetrahydrofuran and methanol, at an elevated temperature, such as 200° C. or 120° C. or 80° C., achieved by either conventional or microwave heating, optionally in a sealed vessel to allow heating above the normal boiling point of the solvent, in the presence of a catalyst, such as a palladium catalyst, such as tetrakis(triphenylphosphine)palladium or (1,1'-bis(diphenylphosphino)ferrocene)-palladium (II chloride dichloromethane complex or PXPd or a palladium catalyst—ligand combination, such as tris(dibenzylideneacetone)dipalladium with dicyclohexyl(2',6'-dimethoxybiphenyl-2-yl)phosphine, optionally in the presence of a base, such as anhydrous tribasic potassium phosphate or potassium carbonate or aqueous sodium carbonate or potassium carbonate solution, under an inert atmosphere, such as argon.

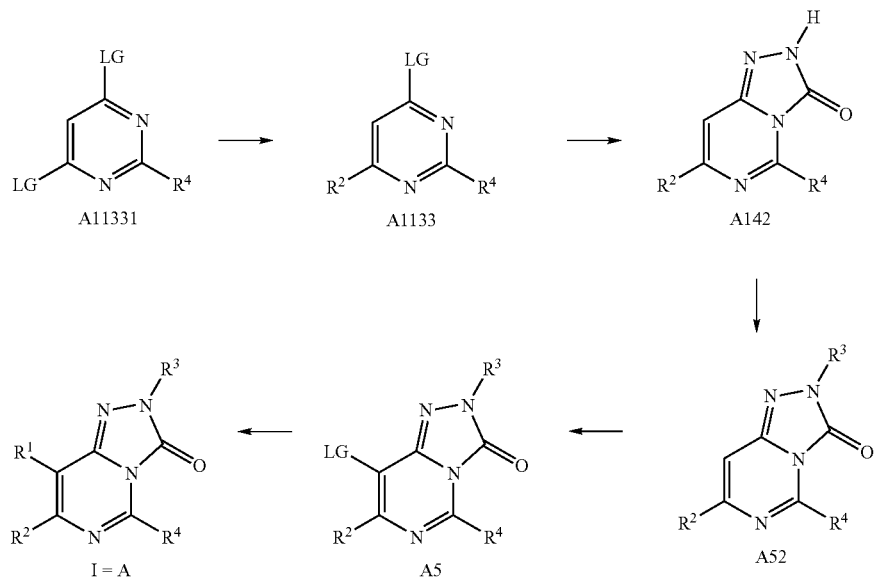

SCHEME 4 achieved by either conventional or microwave heating, optionally in a sealed vessel to allow heating above the normal boiling point of the solvent, in the presence of a catalyst, such as a palladium catalyst, such as tetrakis(triphenylphosphine)palladium or (1,1'-bis(diphenylphosphino)ferrocene)-palladium (II) chloride dichloromethane complex or PXPd or a palladium catalyst—ligand combination, such as tris(dibenzylideneacetone)dipalladium with dicyclohexyl(2',6'-dimethoxybiphenyl-2-yl)phosphine, optionally in the presence of a base, such as anhydrous tribasic potassium phosphate or potassium carbonate or aqueous sodium carbonate or potassium carbonate solution, under an inert atmosphere, such as argon.

A compound of Formula A4, such as a 2-substituted 8-aryl-7-halo-[1,2,4]triazolo[4,3-c]pyrimidin-3(2H)-one, may be converted to a compound of compound of Formula I, such as a 2-substituted 7,8-diaryl-[1,2,4]triazolo[4,3-c]pyrimidin-3(2H)-one or a 2-substituted 8-aryl-7-heteroaryl-[1,2,4]triazolo[4,3-c]pyrimidin-3(2H)-one, for example, by reaction with an $R^2$-containing organometallic reagent, such as an arylboronic acid or a heteroarylboronic acid or the pinacol ester of said boronic acids or an aryltrialkylstannane or a heteroaryltrialkylstannane, in a solvent, such as toluene or tetrahydrofuran or n-butanol or 1,4-dioxane or 1,2-dimethoxyethane or a mixture of solvents, such as tetrahydrofuran and methanol, at an elevated temperature, such as 200° C. or 120° C. or 80° C., achieved by either conventional or microwave heating, optionally in a sealed vessel to allow heating above the normal boiling point of the solvent, in the presence of a catalyst, such as a palladium catalyst, such as tetrakis(triphenylphosphine)palladium or (1,1'-bis(diphenylphosphino)ferrocene)-palladium (II) chloride dichloromethane complex or PXPd or a palladium catalyst—ligand combination, such as tris(dibenzylideneacetone)dipalladium with dicyclohexyl(2',6'-dimethoxybiphenyl-2-yl)phosphine, optionally in the presence of a base, such as anhydrous tribasic potassium phosphate or potassium carbonate or aqueous As shown in Scheme 4, a compound of Formula A11331, such as a 4,6-dihalopyrimidine, may be converted to a compound of Formula A1133, such as a 6-aryl-4-halopyrimidine or a 6-heteroaryl-4-halopyrimidine, for example, by reaction with an $R^2$-containing organometallic reagent, such as an arylboronic acid or a heteroarylboronic acid or the pinacol ester of said boronic acids or an aryltrialkylstannane or a heteroaryltrialkylstannane, in a solvent, such as toluene or tetrahydrofuran or n-butanol or 1,4-dioxane or 1,2-dimethoxyethane or a mixture of solvents, such as tetrahydrofuran and methanol, at an elevated temperature, such as 200° C. or 120° C. or 80° C. achieved by either conventional or microwave heating, optionally in a sealed vessel to allow heating above the normal boiling point of the solvent, in the presence of a catalyst, such as a palladium catalyst, such as tetrakis(triphenylphosphine)palladium or (1,1'-bis(diphenylphosphino)ferrocene)-palladium (II) chloride dichloromethane complex or PXPd or a palladium catalyst—ligand combination, such as tris(dibenzylideneacetone)dipalladium with dicyclohexyl(2',6'-dimethoxybiphenyl-2-yl)phosphine, optionally in the presence of a base, such as anhydrous tribasic potassium phosphate or potassium carbonate or aqueous sodium carbonate or potassium carbonate solution, under an inert atmosphere, such as argon.

A compound of Formula A1133, such as a 6-aryl-4-halopyrimidine, may be converted to a compound of Formula A142, such as a 7-aryl-[1,2,4]triazolo[4,3-c]pyrimidin-3(2H)-one, for example, by first nucleophilic displacement at the 4 position with hydrazine in a solvent, such as tetrahydrofuran or 1,4-dioxane or pyridine, at a temperature, such as ambient temperature or 65° C. or 120° C., under an inert atmosphere, such as argon, followed by treatment with a carbonylating agent, such as 1,1'-carbonyldiimidazole or triphosgene, in a solvent, such as tetrahydrofuran, at a temperature, such as ambient temperature or 60° C., under an inert atmosphere, such as argon.

A compound of Formula A142, such as a 7-aryl-[1,2,4]triazolo[4,3-c]pyrimidin-3(2H)-one, may be converted to a compound of Formula A52, such as a 2-substituted 7-aryl-[1,2,4]triazolo[4,3-c]pyrimidin-3(2H)-one, for example, by reaction with an $R^3$-containing electrophile, $R^3$-LG, such as an optionally substituted benzyl halide or an optionally substituted heteroarylmethyl halide or an optionally substituted alkyl halide, in the presence of a base, such as potassium carbonate, in a solvent, such as N,N-dimethylformamide or acetone, at a temperature, such as ambient temperature or 55° C. or 80° C., under an inert atmosphere, such as argon; or by reaction with an $R^3$-containing alcohol, $R^3$—OH, such as an optionally substituted benzyl alcohol or an optionally substituted heteroarylmethyl alcohol or an optionally substituted alcohol, under Mitsunobu reaction conditions.

A compound of Formula A52, such as a 2-substituted 7-aryl-[1,2,4]triazolo[4,3-c]pyrimidin-3(2H)-one, may be converted to a compound of Formula A5, such as a 2-substituted 7-aryl-8-halo-[1,2,4]triazolo[4,3-c]pyrimidin-3(2H)-one, for example, by reaction with an electrophilic source of halogen, such as molecular bromine or N,N,N-trimethyl-1-phenylmethanaminium tribromide, optionally in the presence of a base, such as calcium carbonate, in a solvent, such as dichloroethane, at a temperature, such as ambient temperature or 70° C., under an inert atmosphere, such as argon.

A compound of Formula A5, such as a 2-substituted 7-aryl-8-halo-[1,2,4]triazolo[4,3-c]pyrimidin-3(2H)-one, may be converted to a compound of compound of Formula I, such as a 2-substituted 7,8-diaryl-[1,2,4]triazolo[4,3-c]pyrimidin-3(2H)-one or a 2-substituted 7-aryl-8-heteroaryl-[1,2,4]triazolo[4,3-c]pyrimidin-3(2H)-one, for example, by reaction with an $R^1$-containing organometallic reagent, such as an arylboronic acid or a heteroarylboronic acid or the pinacol ester of said boronic acids or an aryltrialkylstannane or a heteroaryltrialkylstannane, in a solvent, such as toluene or tetrahydrofuran or n-butanol or 1,4-dioxane or 1,2-dimethoxyethane or a mixture of solvents, such as tetrahydrofuran and methanol, at an elevated temperature, such as 200° C. or 120° C. or 80° C., achieved by either conventional or microwave heating, optionally in a sealed vessel to allow heating above the normal boiling point of the solvent, in the presence of a catalyst, such as a palladium catalyst, such as tetrakis(triphenylphosphine)palladium or (1,1'-bis(diphenylphosphino)ferrocene)-palladium (II) chloride dichloromethane complex or PXPd or a palladium catalyst—ligand combination, such as tris(dibenzylideneacetone)dipalladium with dicyclohexyl(2',6'-dimethoxybiphenyl-2-yl)phosphine, optionally in the presence of a base, such as anhydrous tribasic potassium phosphate or potassium carbonate or aqueous sodium carbonate or potassium carbonate solution, under an inert atmosphere, such as argon.

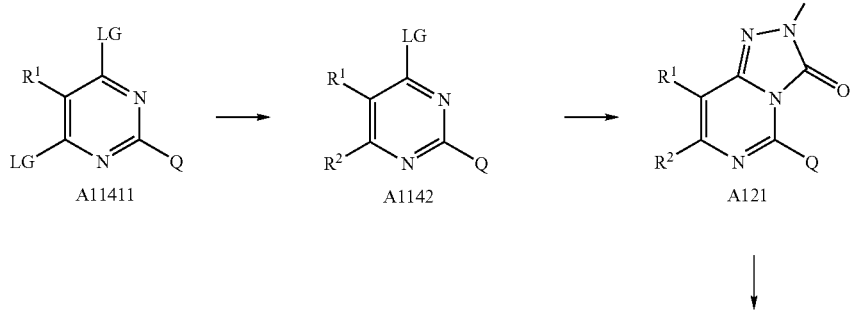

SCHEME 5

-continued

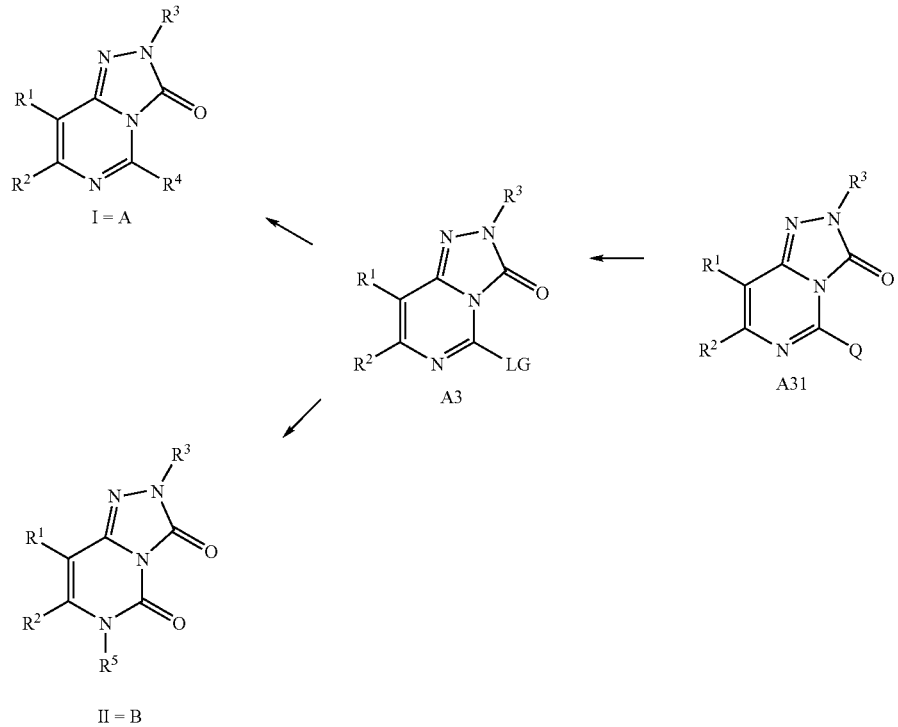

As shown in Scheme 5, a compound of Formula A11411, such as a 4,6-dihalo-2-methylthiopyrimidine, may be converted to a compound of Formula A1142, such as a 6-aryl-4-halo-2-methylthiopyrimidine or a 6-heteroaryl-4-halo-2-methylthiopyridine, for example, by reaction with an $R^2$-containing organometallic reagent, such as an arylboronic acid or a heteroarylboronic acid or the pinacol ester of said boronic acids or an aryltrialkylstannane or a heteroaryltrialkylstannane, in a solvent, such as toluene or tetrahydrofuran or n-butanol or 1,4-dioxane or 1,2-dimethoxyethane or a mixture of solvents, such as tetrahydrofuran and methanol, at an elevated temperature, such as 200° C. or 120° C. or 80° C., achieved by either conventional or microwave heating, optionally in a sealed vessel to allow heating above the normal boiling point of the solvent, in the presence of a catalyst, such as a palladium catalyst, such as tetrakis(triphenylphosphine)palladium or (1,1'-bis(diphenylphosphino)ferrocene)-palladium (II) chloride dichloromethane complex or PXPd or a palladium catalyst—ligand combination, such as tris(dibenzylideneacetone)dipalladium with dicyclohexyl(2',6'-dimethoxybiphenyl-2-yl)phosphine, optionally in the presence of a base, such as anhydrous tribasic potassium phosphate or potassium carbonate or aqueous sodium carbonate or potassium carbonate solution, under an inert atmosphere, such as argon.

A compound of Formula A1142, such as a 6-aryl-4-halo-2-methylthiopyrimidine, may be converted to a compound of Formula A121, such as a 7-aryl-5-methylthio[1,2,4]triazolo[4,3-c]pyrimidin-3(2H)-one, for example, by first nucleophilic displacement at the 4 position with hydrazine in a solvent, such as tetrahydrofuran or 1,4-dioxane or pyridine, at a temperature, such as ambient temperature or 65° C. or 120° C., under an inert atmosphere, such as argon, followed by treatment with a carbonylating agent, such as 1,1'-carbonyldiimidazole or triphosgene, in a solvent, such as tetrahydrofuran, at a temperature, such as ambient temperature or 60° C., under an inert atmosphere, such as argon.

A compound of Formula A121, such as a 7-aryl-5-methylthio[1,2,4]triazolo[4,3-c]pyrimidin-3(2H)-one, may be converted to a compound of Formula A31, such as a 2-substituted 7-aryl-5-methylthio[1,2,4]triazolo[4,3-c]pyrimidin-3(2H)-one, for example, by reaction with an $R^3$-containing electrophile, $R^3$-LG, such as an optionally substituted benzyl halide or an optionally substituted heteroarylmethyl halide or an optionally substituted alkyl halide, in the presence of a base, such as potassium carbonate, in a solvent, such as N,N-dimethylformamide or acetone, at a temperature, such as ambient temperature or 55° C. or 80° C., under an inert atmosphere, such as argon; or by reaction with an $R^3$-containing alcohol, $R^3$—OH, such as an optionally substituted benzyl alcohol or an optionally substituted heteroarylmethyl alcohol or an optionally substituted alcohol, under Mitsunobu reaction conditions.

A compound of Formula A31, such as a 2-substituted 7-aryl-5-methylthio[1,2,4]triazolo[4,3-c]pyrimidin-3(2H)-one, may be converted to a compound of Formula I, such as a 2-substituted 7-aryl-5-methoxy[1,2,4]triazolo[4,3-c]pyrimidin-3(2H)-one or a compound of Formula II, such as a 2-substituted 7-aryl-5-hydroxy[1,2,4]triazolo[4,3-c]pyrimidin-3(2H)-one, through the intermediacy of a compound of Formula A3, such as a 2-substituted 7-aryl-5-methylsulfonyl[1,2,4]triazolo[4,3-c]pyrimidin-3(2H)-one, for example, by reaction with an oxidizing reagent, such as 3-chloroperoxybenzoic acid, in a solvent, such as tetrahydrofuran, at a temperature, such as ambient temperature, under an inert atmosphere, such as argon, followed by reaction with a nucleophilic $R^4$ source, such as methanol, in a solvent, such as tetrahydrofuran, at a temperature, such as ambient temperature or 55° C., under an inert atmosphere, such as argon, to produce a compound of Formula I, or followed by reaction with water in a solvent, such as tetrahydrofuran, at a temperature, such as ambient temperature or 55° C., under an inert atmosphere, such as argon, to produce a compound of Formula II.

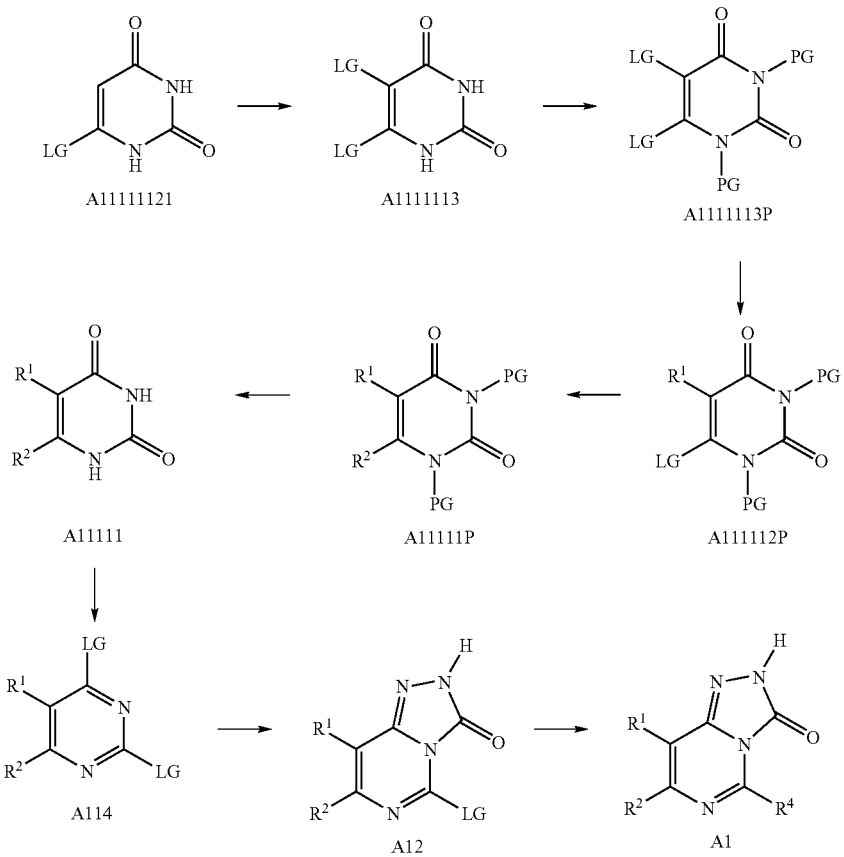

SCHEME 6

As shown in Scheme 6 compound of Formula A11111121, such as a 6-halopyrimidine-2,4(1H,3H)-dione, may be converted to a compound of Formula A1111113, such as a 5,6-dihalopyrimidine-2,4(1H,3H)-dione, for example, by reaction with an electrophilic source of halogen, such as molecular bromine or N,N,N-trimethyl-1-phenylmethanaminium tribromide, in a solvent, such as water or dichloroethane, at a temperature, such as ambient temperature or 100° C., under an inert atmosphere, such as argon.

A compound of Formula A1111113, such as a 5,6-dihalopyrimidine-2,4(1H,3H)-dione, may be converted to a protected compound of Formula A1111113P, such as a 1,3-dibenzyl-5,6-dihalopyrimidine-2,4(1H,3H)-dione, for example, by reaction with protecting reagent, such as a benzyl halide, in the presence of a base, such as potassium carbonate, in a solvent, such as N,N-dimethylformamide or acetone, at a temperature, such as ambient temperature or 55° C. or 80° C., under an inert atmosphere, such as argon.

A compound of Formula A1111113P, such as a 1,3-dibenzyl-5,6-dihalopyrimidine-2,4(1H,3H)-dione, may be converted to a compound of Formula A111112P, such as a 1,3-dibenzyl-5-aryl-6-halopyrimidine-2,4(1H,3H)-dione or a 1,3-dibenzyl-5-heteroaryl-6-halopyrimidine-2,4(1H,3H)-dione, for example, by reaction with an R¹-containing organometallic reagent, such as an arylboronic acid or a heteroarylboronic acid or the pinacol ester of said boronic acids or an aryltrialkylstannane or a heteroaryltrialkylstannane, in a solvent, such as toluene or tetrahydrofuran or n-butanol or 1,4-dioxane or 1,2-dimethoxyethane or a mixture of solvents, such as tetrahydrofuran and methanol, at an elevated temperature, such as 200° C. or 120° C. or 80° C., achieved by either conventional or microwave heating, optionally in a sealed vessel to allow heating above the normal boiling point of the solvent, in the presence of a catalyst, such as a palladium catalyst, such as tetrakis(triphenylphosphine)palladium or (1,1'-bis(diphenylphosphino)ferrocene)-palladium (II) chloride dichloromethane complex or PXPd or a palladium catalyst—ligand combination, such as tris(dibenzylideneacetone)dipalladium with dicyclohexyl(2',6'-dimethoxybiphenyl-2-yl)phosphine, optionally in the presence of a base, such as anhydrous tribasic potassium phosphate or potassium carbonate or aqueous sodium carbonate or potassium carbonate solution, under an inert atmosphere, such as argon.

A compound of Formula A111112P, such as a 1,3-dibenzyl-5-aryl-6-halopyrimidine-2,4(1H,3H)-dione, may be converted to a compound of Formula A11111P, such as a 1,3-dibenzyl-5,6-diarylpyrimidine-2,4(1H,3H)-dione or a 1,3-dibenzyl-5-aryl-6-heteroarylpyrimidine-2,4(1H,3H)-dione, for example, by reaction with an R²-containing organometallic reagent, such as an arylboronic acid or a heteroarylboronic acid or the pinacol ester of said boronic acids or an aryltrialkylstannane or a heteroaryltrialkylstannane, in a solvent, such as toluene or tetrahydrofuran or n-butanol or 1,4-dioxane or 1,2-dimethoxyethane or a mixture of solvents, such as tetrahydrofuran and methanol, at an elevated temperature, such as 200° C. or 120° C. or 80° C., achieved by either conventional or microwave heating, optionally in a sealed vessel to allow heating above the normal boiling point of the solvent, in the presence of a catalyst, such as a palladium catalyst, such as tetrakis(triphenylphosphine)palladium or (1,1'-bis(diphenylphosphino)ferrocene)-palladium (II) chloride dichloromethane complex or PXPd or a palladium catalyst—ligand combination, such as tris(dibenzylideneacetone)dipalladium with dicyclohexyl(2',6'-dimethoxybiphenyl-2-yl)phosphine, optionally in the presence of a base, such as anhydrous tribasic potassium phosphate or potassium carbonate or aqueous sodium carbonate or potassium carbonate solution, under an inert atmosphere, such as argon.

A compound of Formula A11111P, such as a 1,3-dibenzyl-5,6-diarylpyrimidine-2,4(1H,3H)-dione, may be converted to a deprotected compound of Formula A11111, such as a 5,6-diarylpyrimidine-2,4(1H,3H)-dione, for example, by reaction with deprotecting reagent, such as a aluminum chloride, in a solvent, such as toluene, at a temperature, such as 85° C., under an inert atmosphere, such as argon, followed by an aqueous workup.

A compound of Formula A1111, such as a 5,6-diarylpyrimidine-2,4(1H,3H)-dione, may be converted to a compound of Formula A114, such as a 5,6-diaryl-2,4-dihalopyrimidine, for example, by reaction with a mixed anhydride of a hydrohalic acid, such as phosphorous oxychloride or phosphorus pentachloride or phosphorus oxybromide, optionally in a solvent, such as a chlorinated hydrocarbon, at an elevated temperature, such as 100° C., optionally in the presence of a substoichiometric amount of N,N-dimethylformamide, under an inert atmosphere, such as argon.

A compound of Formula A114, such as a 5,6-diaryl-2,4-dihalopyrimidine, may be converted to a compound of Formula A12, such as a 7,8-diaryl-5-halo[1,2,4]triazolo[4,3-c]pyrimidin-3(2H)-one, for example, by first nucleophilic displacement at the 4 position with hydrazine in a solvent, such as tetrahydrofuran or 1,4-dioxane or pyridine, at a temperature, such as ambient temperature or 65° C. or 120° C., under an inert atmosphere, such as argon, followed by treatment with a carbonylating agent, such as 1,1'-carbonyldiimidazole or triphosgene, in a solvent, such as tetrahydrofuran, at a temperature, such as ambient temperature or 60° C., under an inert atmosphere, such as argon.

A compound of Formula A12, such as a 7,8-diaryl-5-halo[1,2,4]triazolo[4,3-c]pyrimidin-3(2H)-one, may be converted to a compound of Formula A1, such as a 7,8-diaryl-5-amino[1,2,4]triazolo[4,3-c]pyrimidin-3(2H)-one or a 7,8-diaryl-5-alkyl[1,2,4]triazolo[4,3-c]pyrimidin-3(2H)-one, for example, by reaction with a nucleophilic reagent, such as an amine or an alkyl zinc reagent, respectively, in a solvent, such as ethanol or tetrahydrofuran, at a temperature, such as ambient temperature or 60° C., optionally in the presence of a catalyst, such as a palladium catalyst, such as tetrakis(triphenylphosphine)palladium, under an inert atmosphere, such as argon.

A compound of Formula A1, may be converted to a compound of Formula I as described in Scheme 2

In the preceding synthetic schemes, reagents $R^3$-LG and $R^3$—OH were utilized to install the $R^3$ group of compounds of Formulas I and II. The following synthetic schemes focus on some of the more useful synthetic routes to reagents $R^3$-LG, such as substituted benzyl halides and substituted heteroarylmethyl halides, and to the corresponding $R^3$—OH compounds. See, respectively, P3 annd P4 below.

SCHEME 7

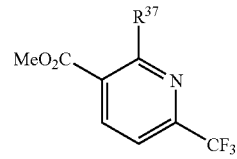

P1

The synthesis of a compound of Formula P1 (Scheme 7), such as methyl 2-cyclopropyl-6-(trifluoromethyl)nicotinate, wherein $R^{37}$ is a group as defined for $R^{11}$, especially an alkyl group that may be optionally substituted with 1 to 3 $R^{12}$, may be accomplished according to E. Okada, et al., Heterocycles, volume 46, pp. 129-132, 1997 by reaction of (Z)-4-amino-1,1,1-trifluorobut-3-en-2-one with a methyl 3-($R^{37}$-substituted)-3-oxopropanoate, such as methyl 3-cyclopropyl-3-oxopropanoate, in a solvent, such as toluene, at an elevated temperature, such as 80° C., in the presence of an acid, such as trifluoroacetic acid, under an inert atmosphere, such as argon.

SCHEME 8

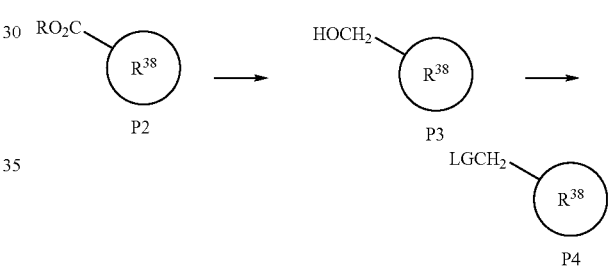

As shown in Scheme 8, a compound of Formula P2, such as P1, a methyl 2-($R^{37}$-substituted)-6-(trifluoromethyl)nicotinate, or another ring-substituted pyridinecarboxylate ester or ring-substituted benzenecarboxylate ester, wherein $R^{38}$ is an aryl or heteroaryl group as defined for $R^{10}$ that may be optionally substituted with 1 to 3 $R^{11}$, may be converted to a compound of Formula P3, such as a ring-substituted pyridinemethanol or ring-substituted benzenemethanol, for example, by reaction with a reducing agent, such as lithium aluminum hydride or sodium borohydride in a solvent, such as diethyl ether or tetrahydrofuran or an alcohol, such as methanol, when the reducing agent is sodium borohydride, at a temperature, such as room temperature or 0° C. or −78° C., the latter especially when the reducing agent is lithium aluminum hydride, under an inert atmosphere, such as argon.

A compound of Formula P3, such as a ring-substituted pyridinemethanol or ring-substituted benzenemethanol, wherein $R^{38}$ is an aryl or heteroaryl group as defined for $R^{10}$ that may be optionally substituted with 1 to 3 $R^{11}$, may be converted to a compound of Formula P4, such as a ring-substituted (halomethyl)pyridine or ring-substituted (halomethyl)benzene, for example, by reaction with a reagent, such as thionyl chloride, optionally in the presence of N,N-dimethylformamide, or 48% aqueous hydrobromic acid or a combination of reagents, such as carbon tetrabromide and triphenylphosphine, optionally in a solvent, such as dichloromethane, at a temperature, such as room temperature or 0° C. or 80° C., under an inert atmosphere, such as argon. Alternatively, a compound of Formula P3, such as a ring-substituted pyridinemethanol or ring-substituted benzenemethanol may be converted to a compound of Formula P4, such as a ring-substituted (methanesulfonyloxymethyl)pyridine or ring-substituted (trifluoromethylsulfonyloxymethyl) benzene, for example, by reaction with a sulfonyl chloride reagent under standard conditions as described in the art.

SCHEME 9

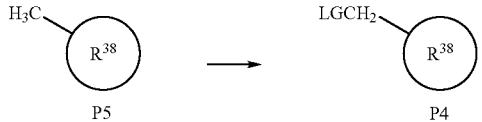

As shown in Scheme 9, a compound of Formula P5, such as a ring-substituted methylpyridine or ring-substituted methylbenzene, wherein $R^{38}$ is an aryl or heteroaryl group as defined for $R^{10}$ that may be optionally substituted with 1 to 3 $R^{11}$, may be converted to a compound of Formula P4, such as a ring-substituted (halomethyl)pyridine or ring-substituted (halomethyl)benzene, for example, by reaction with a radical halogenating reagent, such as N-chlorosuccinimide or N-bromosuccinimide or molecular bromine, optionally in the presence of a radical initiator such as benzoyl peroxide, in a solvent, such as carbon tetrachloride, at a temperature, such as room temperature or 80° C., under an inert atmosphere, such as argon.

SCHEME 10

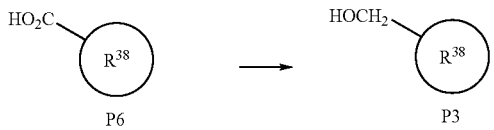

As shown in Scheme 10, a compound of Formula P6, such as a ring-substituted pyridinecarboxylic acid or ring-substituted benzenecarboxylic acid, wherein $R^{38}$ is an aryl or heteroaryl group as defined for $R^{10}$ that may be optionally substituted with 1 to 3 $R^{11}$, may be converted to a compound of Formula P3, such as a ring-substituted pyridinemethanol or ring-substituted benzenemethanol, for example, by reaction with a reducing agent, such as borane, in a solvent, such as tetrahydrofuran, at a temperature, such as room temperature or 0° C. or 70° C., under an inert atmosphere, such as argon.

SCHEME 11

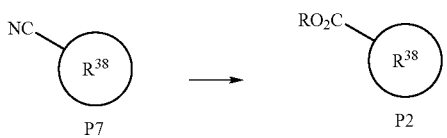

As shown in Scheme 11, a compound of Formula P7, such as a ring-substituted pyridinenitrile or ring-substituted benzonitrile, wherein $R^{38}$ is an aryl or heteroaryl group as defined for $R^{10}$ that may be optionally substituted with 1 to 3 $R^{11}$, may be converted to a compound of Formula P2, such as a ring-substituted pyridinecarboxylate ester or ring-substituted benzenecarboxylate ester, for example, by reaction with an alcohol, such as methanol or ethanol, and an aqueous mineral acid, such as concentrated aqueous hydrochloric acid, optionally with concentrated sulfuric acid, at a temperature, such as 100° C., under an inert atmosphere, such as argon.

EXAMPLES

The following examples serve to better illustrate, but not limit, some of the preferred embodiments of the invention.

General

The following methods were used in the working Examples, except where noted otherwise.

Reverse phase preparative HPLC employed a 5 μm octadecyl sulfate (C-18) column eluted with a linear solvent gradient of solvents A and B. In most cases, and unless noted otherwise, solvent A was 10% methanol in water, and solvent B was 90% methanol in water. In some of these cases both solvents A and B contained either 0.1% of trifluoroacetic acid or 10 mM ammonium acetate, as noted (no notation indicates no additive). The solvent gradient employed with methanol-water based solvents began with 20% or more of solvent B and ended with 100% of solvent B.

Reverse phase analytical HPLC was performed on Shimadzu LC10AS systems employing a 5 μm C-18 4.6×50 mm column eluted with a linear solvent gradient, starting with 0% of solvent B and finishing with 100% of solvent B over 4 min, with 1 min hold time at 100% B and at a flow rate of 4 mL/min with UV detection at 220 nm. In most cases, and unless noted otherwise, solvent A was 10% methanol in water, and solvent B was 90% methanol in water, each containing 0.2% phosphoric acid.

Analytical HPLC/MS was performed, in most cases, on Shimadzu LC10AS systems coupled with Waters ZMD mass spectrometers. The HPLC system employed a PHENOMEX LUNA or WATERS SUNFIRE C-18 4.6×50 mm column eluted with solvent A (0.1% trifluoroacetic acid, 90% water, 10% methanol) and solvent B (0.1% trifluoroacetic acid, 90% methanol, 10% water) through a linear gradient of 0% to 100% solvent B over 4 min, with 1 min hold time at 100% B and at a flow rate of 4 mL/min with UV detection at 220 nm. In some cases, 10 mM ammonium acetate rather than 0.1% trifluoroacetic acid was the solvent additive, as noted (no notation indicates the use of 0.1% trifluoroacetic acid). Diagnostic HPLC/MS m/z values, for instance for [M+H]+, are generally given for only the lowest m/z or main peak in cases where isotope patterns appear. In these cases, it is understood that rest of the isotope pattern peaks are present and confirm the assigned structure.

NMR spectra were obtained with Bruker or Jeol Fourier transform spectrometers operating at frequencies as follows. $^1$H NMR: 400 MHz (Bruker or Jeol) or 500 MHz (Jeol). $^{13}$C NMR: 100 MHz (Bruker or Jeol). $^1$H NMR spectra are reported in the format: chemical shift (multiplicity, coupling constants, number of hydrogens). Chemical shifts are specified in ppm downfield of a tetramethylsilane internal standard (δ units, tetramethylsilane=0 ppm) and/or referenced to solvent peaks, which in $^1$H NMR spectra appear at 2.49 ppm for $CD_2HSOCD_3$, 3.30 ppm for $CD_2HOD$, and 7.24 ppm for $CHCl_3$, and which in $^{13}$C NMR spectra appear at 39.7 ppm for $CD_3SOCD_3$, 49.0 ppm for $CD_3OD$, and 77.0 ppm for $CDCl_3$. All $^{13}$C NMR spectra were proton decoupled.

Example 1

Preparation of 7-(4-chlorophenyl)-8-phenyl-2-((6-(trifluoromethyl)pyridin-3-yl)methyl)-[1,2,4]triazolo[4,3-c]pyrimidin-3(2H)-one

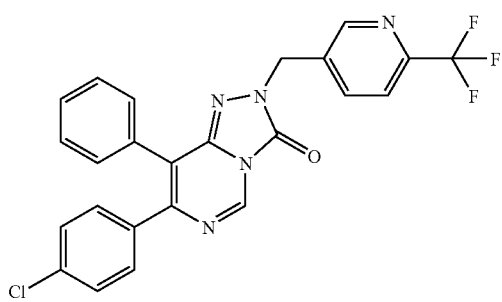

A. Preparation of 5-phenylpyrimidine-4,6-diol

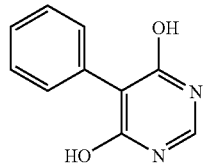

Sodium metal (0.92 g, 40 mmol) was dissolved by stirring in ethanol (30 mL) at room temperature under argon over 40 min. To the resulting solution at room temperature was added 2-phenylmalonamide (3.56 g, 20 mmol) and ethyl formate (1.9 mL, 24 mmol). The resulting suspension was heated at 50° C. under argon 16 h. After cooling the reaction mixture to room temperature, water (100 mL) was added and the mixture was stirred for 1 h. Solid was removed by filtration. The filtrate was acidified to pH~4 with 1 M aqueous HCl. The resulting precipitate was collected by filtration and further washed with water (20 mL×2), then Et$_2$O (10 mL×2). After drying under vacuum for 3 h, the title compound (2.6 g) was obtained as a light yellow solid. HPLC/MS: retention time=0.76 min, [M+H]$^+$=189.

B. Preparation of 4,6-dichloro-5-phenylpyrimidine

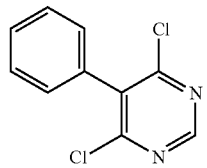

A suspension of 5-phenylpyrimidine-4,6-diol (2.6 g, 13.8 mmol) in POCl$_3$ (20 mL) was heated at 100° C. under argon. A brown solution was observed after 15 min. HPLC/MS analysis after 2 h indicated that the reaction was completed. After the solvent was mostly removed under reduced pressure, ice (100 g) was added to the residue and the resulting mixture was stirred for 1 h. The product was collected by filtration and further washed with water (10 mL×3), and then dried under vacuum.

The title compound (2.3 g) was obtained as a white solid. HPLC/MS: retention time 3.25 min, [M+H]$^{30}$ =225

C. Preparation of 4-chloro-6-(4-chlorophenyl)-5-phenylpyrimidine

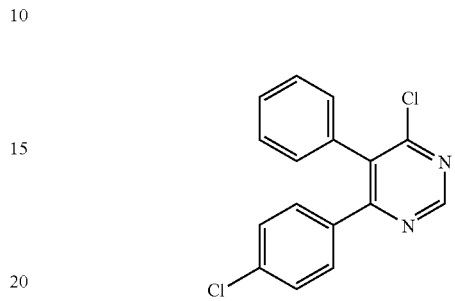

To a mixture of 4,6-dichloro-5-phenylpyrimidine (675 mg, 3.0 mmol), 4-chlorophenylboronic acid (704 mg, 4.5 mmol) and tetrakis(triphenylphosphine)palladium (173 mg, 0.15 mmol) in toluene (10 mL) at room temperature under argon was added aqueous Na$_2$CO$_3$ solution (2 M, 3 mL, 6 mmol). The resulting reaction mixture was stirred at 100° C. under argon for 5 h, after which time analysis by HPLC/MS indicated that the the reaction was complete. After cooling the reaction mixture to room temperature, water (15 mL) was added. The resulting mixture was extracted with EtOAc (2×25 mL). The combined organic layers were washed with saturated aqueous NaCl, then dried over Na$_2$SO$_4$, filtered and concentrated under reduced pressure. The residue was purified by silica gel column chromatography eluted with ethyl acetate-hexanes to obtain 571 mg of the title compound as a white solid. HPLC/MS: retention time=3.85 min, [M+H]$^{30}$ =301.

D. Preparation of 1-(6-(4-chlorophenyl)-5-phenylpyrimidin-4-yl)hydrazine

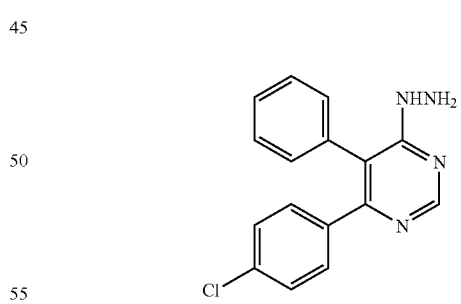

To a stirred solution of 4-chloro-6-(4-chlorophenyl)-5-phenylpyrimidine (301 mg, 1.0 mmol) in THF (5 mL) at room temperature under argon was added H$_2$NNH$_2$ (160 mg, 5.0 mmol). The reaction mixture was heated at 60° C. under argon for 2 h. Analysis by HPLC/MS indicated that the reaction was complete. The solvent was evaporated and the residue was coevaporated with toluene (2×5 mL) and THF (5 mL), then dried under vacuum. The crude title compound was used directly in the next step. HPLC/MS: retention time=1.89 min, [M+H]$^{30}$ =297.

E. Preparation of 7-(4-chlorophenyl)-8-phenyl-[1,2,4]triazolo[4,3-c]pyrimidin-3(2H)-one and/or trichloromethyl 2-(6-(4-chlorophenyl)-5-phenylpyrimidin-4-yl)hydrazinecarboxylate.

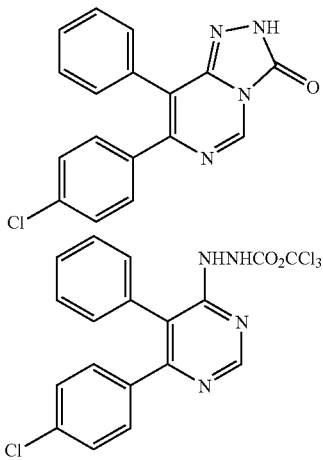

To a stirred solution of triphosgene (890 mg, 3.0 mmol) in THF (5 mL) at room temperature under argon was added a suspension of 1-(6-(4-chlorophenyl)-5-phenylpyrimidin-4-yl)hydrazine (300 mg, 1.0 mmol) in THF (5 mL). The reaction mixture was stirred overnight. Analysis by HPLC/MS indicated that no starting material remained. The reaction mixture was cooled to 0° C. in an ice bath and ice water (100 mL) was added. After stirring for 30 min, the solid precipitate was collected and further washed with water (3×5 mL), then methanol (2×3 mL). The title compound(s) (179 mg) was obtained as an off-white solid. HPLC/MS: retention time=3.40 min, $[M+H]^{30}$ =323.

F. Preparation of 7-(4-chlorophenyl)-8-phenyl-2-((6-(trifluoromethyl)pyridin-3-yl)methyl)-[1,2,4]triazolo[4,3-c]pyrimidin-3(2H)-one

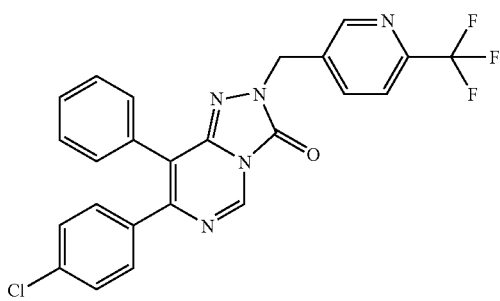

To a stirred solution of 7-(4-chlorophenyl)-8-phenyl-[1,2,4]triazolo[4,3-c]pyrimidin-3(2H)-one and/or trichloromethyl 2-(6-(4-chlorophenyl)-5-phenylpyrimidin-4-yl)hydrazinecarboxylate (32.2 mg, 0.10 mmol) in DMF (2 mL) at room temperature under argon was added 5-(chloromethyl)-2-(trifluoromethyl)pyridine (29.4 mg, 0.15 mmol), followed by $K_2CO_3$ (27.6 mg, 0.20 mmol). The resulting mixture was heated at 60° C. for 1 h. The crude product was purified by silica gel column chromatography eluted with ethyl acetate-hexanes, then lyophilized from 1,4-dioxane, to obtain the title compound (18.3 mg) as an off-white lyophilate. HPLC/MS: retention time=3.90 min, $[M+H]^{30}$ =482. $^1$H NMR (CDCl$_3$): δ 8.80 (d, J=1.5 Hz, 1H), 8.70 (s, 1H), 7.94 (dd, J=7.9, 1.5 Hz, 1H), 7.69 (d, J=7.9 Hz, 2H), 7.28-7.47 (m, 7H), 7.20 (d, J=7.2 Hz, 2H), 5.22 (s, 2H). N-alkylation, rather than O-alkylation, was demonstrated by the presence of a $^{13}$C NMR resonance at 46.8 ppm.

Example 2

Preparation of 2-(4-(isoxazol-5-yl)benzyl)-7-(4-chlorophenyl)-8-phenyl-[1,2,4]triazolo[4,3-c]pyrimidin-3(2H)-one

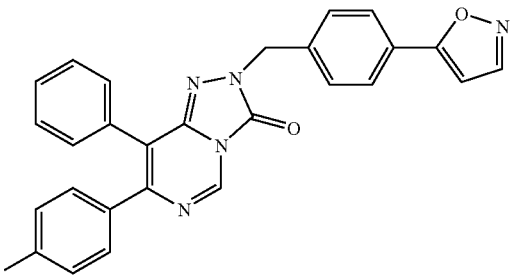

To a stirred solution of 7-(4-chlorophenyl)-8-phenyl-[1,2,4]triazolo[4,3-c]pyrimidin-3(2H)-one and/or trichloromethyl 2-(6-(4-chlorophenyl)-5-phenylpyrimidin-4-yl)hydrazinecarboxylate (16.0 mg, 0.05 mmol) in acetone (5 mL) at room temperature under argon was added 5-(4-(bromomethyl)phenyl)isoxazole (23.8 mg, 0.10 mmol), followed by $K_2CO_3$ (13.8 mg, 0.10 mmol). The resulting mixture was heated at 60° C. for 17 h. Insoluble material was filtered and rinsed with $CH_2Cl_2$. The filtrate was concentrated under reduced pressure and purified by reverse phase preparative HPLC (without TFA). Further purification was performed by silica gel column chromatography eluting with EtOAc-hexanes. Pure product was lyophilized from 1,4-dioxane to obtain the title compound (3.5 mg) as an off-white lyophilate. HPLC/MS: retention time=3.88 min, $[M+H]^{30}$ =480. $^1$H NMR (CDCl$_3$): δ 8.71 (s, 1H), 8.28 (d, J=1.2 Hz, 1H), 7.81 (d, J=7.3 Hz, 2H), 7.45 (d, J=7.3 Hz, 2H), 7.26-7.42 (m, 7H), 7.18 (d, J=7.2 Hz, 2H), 6.51 (d, J=1.2 Hz, 1H), 5.18 (s, 2H).

Example 3

Preparation of 2-(4-(trifluoromethyl)benzyl)-7-(4-chlorophenyl)-8-phenyl-[1,2,4]triazolo[4,3-c]pyrimidin-3(2H)-one

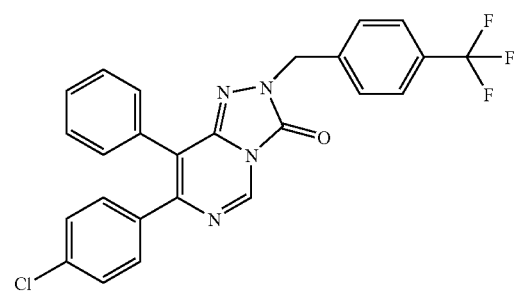

To a stirred solution of 7-(4-chlorophenyl)-8-phenyl-[1,2,4]triazolo[4,3-c]pyrimidin-3(2H)-one and/or trichloromethyl 2-(6-(4-chlorophenyl)-5-phenylpyrimidin-4-yl)hydrazinecarboxylate (16.0 mg, 0.05 mmol) in acetone (5 mL) at room temperature under argon was added 1-(bromomethyl)-4-(trifluoromethyl)benzene (23.9 mg, 0.10 mmol), followed by K$_2$CO$_3$ (13.8 mg, 0.10 mmol). The resulting mixture was heated at 60° C. for 24 h. Insoluble material was filtered and rinsed with CH$_2$Cl$_2$. The filtrate was concentrated under reduced pressure and purified by reverse phase preparative HPLC (without TFA). Further purification was performed by silica gel column chromatography eluting with EtOAc-hexanes. Pure product was lyophilized from 1,4-dioxane to obtain the title compound (5.0 mg) as an off-white lyophilate. HPLC/MS: retention time=4.18 min. [M+H]$^{30}$ =481. $^1$H NMR (CDCl$_3$): δ 8.70 (s, 1H), 7.65 (d, J=7.3 Hz, 2H), 7.55 (d, J=7.3 Hz, 2H), 7.23-7.46 (m, 7H), 7.20 (d, J=7.2 Hz, 2H), 5.18 (s, 2H).

Example 4

Preparation of 7,8-bis(4-chlorophenyl)-2-((6-(trifluoromethyl)pyridin-3-yl)methyl)-[1,2,4]triazolo[4,3-c]pyrimidin-3(2H)-one

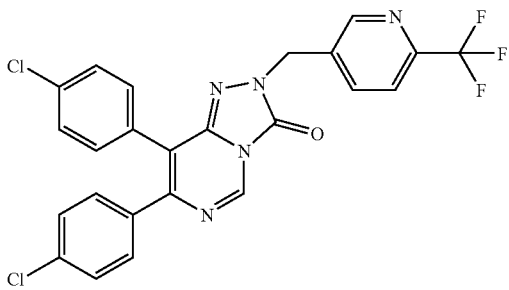

A. Preparation of 8-amino-7-chloro-[1,2,4]triazolo[4,3-c]pyrimidin-3(2H)-one

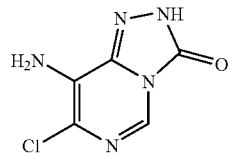

To a solution of 5-amino-4,6-dichloropyrimidine (1.64 g, 10 mmol) in THF (10 mL) at room temperature under argon was added H$_2$NNH$_2$ (0.96 g mg, 30 mmol). The resulting reaction mixture was stirred at room temperature under argon for 50 h. HPLC analysis indicated disappearance of the starting material. Water (100 mL) was added to the reaction mixture. The solid precipitate was collected by filtration and was washed with water (10 mL×3). The resulting solid was dissolved in a mixture of 20 mL of 1 M aqueous HCl and 10 mL of 1,4-dioxane. Triphosgene (7.6 g, 25.7 mmol) was then added. After the reaction mixture had stirred at room temperature under argon for 3 h, analysis by HPLC/MS indicated that the reaction was complete. Water (50 mL) was added to the reaction mixture. The solid precipitate was collected by filtration and was washed with water (5 mL×3). After the resulting solid was dried under vacuum, the title compound (1.41 g) was obtained as a tan solid. HPLC/MS: retention time=0.93 min, [M+H]$^{30}$ =186. See also C. Temple, Jr., et al., J. Org. Chem., volume 33, pp. 530-533, 1968.

B. Preparation of 8-amino-7-chloro-2-((6-(trifluoromethyl)pyridin-3-yl)methyl)-[1,2,4]triazolo[4,3-c]pyrimidin-3(2H)-one

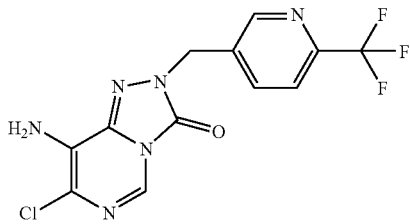

To a stirred solution of 8-amino-7-chloro-[1,2,4]triazolo[4,3-c]pyrimidin-3(2H)-one (1.41 g, 7.6 mmol) in DMF (10 mL) at room temperature under argon was added 5-(chloromethyl)-2-(trifluoromethyl)pyridine (1.78 g, 9.1 mmol), followed by K$_2$CO$_3$ (2.1 g, 15.2 mmol). The resulting mixture was stirred at room temperature for 5 h. Analysis by HPLC/MS indicated that the reaction was complete. Water (50 mL) was added to the reaction mixture. The solid precipitate was collected by filtration and was washed with water (10 mL×3). After the resulting solid was dried under vacuum, the title compound (2.4 g) was obtained as an off-white solid. HPLC/MS: retention time 2.43 min, [M+H]$^{30}$ =345. $^1$H NMR (CDCl$_3$): δ 8.81 (s, 1H), 8.12 (s, 1H), 7.92 (d, J=7.0 Hz, 1H), 7.69 (d, J=7.0 Hz, 1H), 5.21 (s, 2H), 4.42 (s, 2H). N-alkylation, rather than O-alkylation, was demonstrated by the presence of a $^{13}$C NMR resonance at 46.9 ppm.

C. Preparation of 8-bromo-7-chloro-2-((6-(trifluoromethyl)pyridin-3-yl)methyl-[1,2,4]triazolo[4,3-c]pyrimidin-3(2H)-one

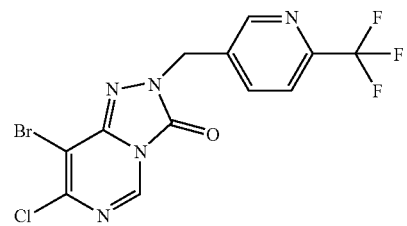

To a stirred mixture of t-BuONO (206 mg, 2.0 mmol) and CuBr$_2$ (335 mg, 1.5 mmol) in acetonitrile (10 mL) at 65° C. under argon was added 8-amino-7-chloro-2-((6-(trifluoromethyl)pyridin-3-yl)methyl)-[1,2,4]triazolo[4,3-c]pyrimidin-3(2H)-one (344 mg, 1.0 mmol) as a solid over 2 min. The resulting mixture was heated at 65° C. for 30 min. Analysis by HPLC/MS indicated that the reaction was complete. After the reaction mixture was cooled to room temperature, 10% aqueous NaHSO$_3$ solution (15 mL) was added. The resulting mixture was extracted with EtOAc (20 mL×3). The combined organic phases were washed with saturated aqueous NaHCO$_3$ (20 mL), then saturated aqueous NaCl (20 mL), then dried (Na$_2$SO$_4$), filtered, and concentrated under reduced pressure. The crude product was purified by silica gel column chromatography eluted with ethyl acetate-hexanes to obtain the title compound (193 mg) as a tan solid. HPLC/MS: retention time=2.97 min, [M+H]+ =408. $^1$H NMR (CDCl$_3$): δ 8.83 (s, 1H), 8.51 (s, 1H), 7.95 (d, J=8.4 Hz, 1H), 7.70 (d, J=8.4 Hz, 1H), 5.25 (s, 2H).

D. Preparation of 7,8-bis(4-chlorophenyl)-2-((6-(trifluoromethyl)pyridin-3-yl)methyl)-[1,2,4]triazolo[4,3-c]pyrimidin-3(2H)-one

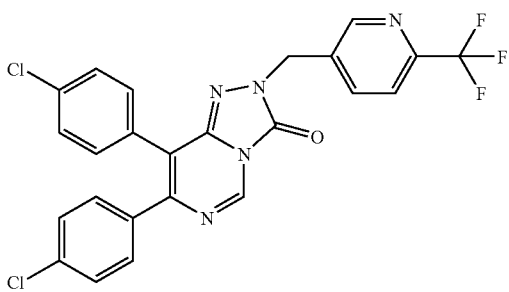

To a solution of 8-bromo-7-chloro-2-((6-(trifluoromethyl)pyridin-3-yl)methyl)-[1,2,4]triazolo[4,3-c]pyrimidin-3(2H)-one (81.3 mg, 0.20 mmol) in toluene (3 mL) at room temperature under argon was added 4-chlorophenylboronic acid (46.8 mg, 0.30 mmol), tetrakis(triphenylphosphine)palladium (46 mg, 0.040 mmol), and aqueous Na$_2$CO$_3$ solution (2.0 M, 0.20 mL, 0.40 mmol). The resulting suspension was stirred and heated at 100° C. under argon for 22 h. Analysis by HPLC/MS indicated that starting material had been consumed. After the reaction mixture was cooled to room temperature, water (10 mL) and EtOAc (15 mL) were added. The layers were separated. The organic layer was dried (Na$_2$SO$_4$), filtered, and concentrated under reduced pressure. The crude product was purified by silica gel column chromatography eluted with ethyl acetate-hexanes to obtain the title compound (7.6 mg) as an off-white solid. HPLC/MS: retention time=4.10 min, [M+H]+ =516.

Example 5

Preparation of 7-(4-chlorophenyl)-8-(pyridin-4-yl)-2-((6-(trifluoromethyl)pyridin-3-yl)methyl)-[1,2,4]triazolo[4,3-c]pyrimidin-3(2H)-one

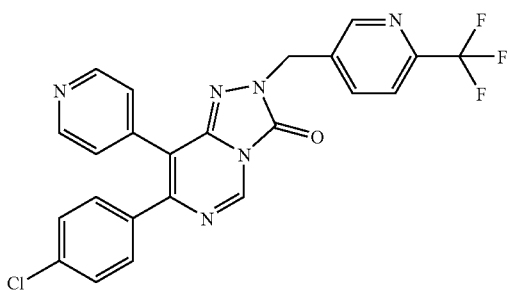

A. Preparation of 4-chloro-6-(4-chlorophenyl)pyrimidine

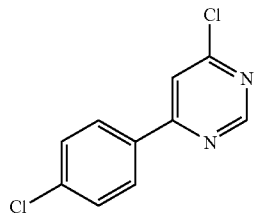

To a mixture of 4,6-dichloropyrimidine (1.49 g, 10.0 mmol), 4-chlorophenylboronic acid (1.72 g, 11.0 mmol) and tetrakis(triphenylphosphine)palladium (1.2 g, 1.0 mmol) in toluene (20 mL) at room temperature under argon was added aqueous Na$_2$CO$_3$ solution (2 M, 10 mL, 20 mmol). The resulting reaction mixture was stirred at 100° C. under argon for 6 h, after which time analysis by HPLC/MS indicated that the reaction was complete. After cooling the reaction mixture to room temperature, water (50 mL) was added. The resulting mixture was extracted with EtOAc (50 mL). The organic layer was washed with saturated aqueous NaCl, then dried over Na$_2$SO$_4$, filtered and concentrated under reduced pressure. The residue was purified by trituration with MeOH (15 mL) to obtain 1.31 g of the title compound as a white solid (purity was about 80% by HPLC analysis). HPLC/MS: retention time=3.65 min, [M+H]+ =225.

B. Preparation of 4-(4-chlorophenyl)-6-hydrazinylpyrimidine

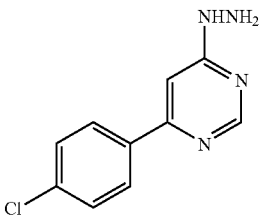

To a stirred solution of 4-chloro-6-(4-chlorophenyl)pyrimidine (1.25 g, 5.6 mmol) in THF (10 mL) at room temperature under argon was added H$_2$NNH$_2$ (538 mg, 16.8 mmol). The reaction mixture was heated at 60° C. under argon for 2 h. Analysis by HPLC/MS indicated that the reaction was complete. About three fourths of the solvent was evaporated and Et$_2$O (5 mL) was added to the resulting suspension. After stirring at room temperature for 20 min, solid was collected by filtration and further washed with Et$_2$O (15 mL), then dried under vacuum to obtain 831 mg of the title compound as a white solid. HPLC/MS: retention time=1.88 min, [M+H]+ =221.

C. Preparation of 7-(4-chlorophenyl)-[1,2,4]triazolo[4,3-c]pyrimidin-3(2H)-one

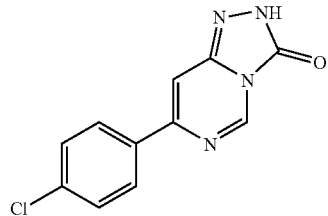

To a stirred solution of triphosgene (2.86 g, 9.66 mmol) in THF (10 mL) at room temperature under argon was added a suspension of 4-(4-chlorophenyl)-6-hydrazinylpyrimidine (825 mg, 3.22 mmol) in THF (10 mL). The reaction mixture was stirred overnight. Analysis by HPLC/MS indicated that no starting material remained. Solvent was removed under reduced pressure and water (50 mL) was added. After stirring for 30 min, the solid precipitate was collected and further washed with water (3×10 mL), then methanol (3×5 mL). The title compound (793 mg) was obtained as an off-white solid. HPLC/MS: retention time=2.74 min, $[M+H]^{30}$ =247.

D. Preparation of 7-(4-chlorophenyl)-2-((6-(trifluoromethyl)pyridin-3-yl)methyl)-[1,2,4]triazolo[4,3-c]pyrimidin-3(2H)-one

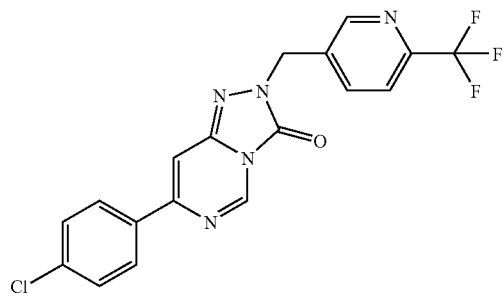

To a stirred suspension of 7-(4-chlorophenyl)-[1,2,4]triazolo[4,3-c]pyrimidin-3(2H)-one (738 mg, 3.0 mmol) in DMF (5 mL) at room temperature under argon was added 5-(chloromethyl)-2-(trifluoromethyl)pyridine (647 mg, 3.3 mmol), followed by $K_2CO_3$ (828 mg, 6.0 mmol). The resulting mixture was heated at 60° C. for 48 h, after which time analysis by HPLC/MS indicated that the reaction was complete. After cooling the reaction mixture to room temperature, water (50 mL) was added. The resulting mixture was extracted with EtOAc (2×25 mL). The combined organic layers were washed with saturated aqueous NaCl, then dried over $Na_2SO_4$, filtered and evaporated under reduced pressure. The resulting residue was triturated with chloroform (3×20 mL) and filtered. The filtrate was concentrated under reduced pressure and purified by column chromatography eluted with ethyl acetate-dichloromethane to obtain 206 mg of the title compound as a solid. HPLC/MS (methanol-water with 10 mM $NH_4OAc$): retention time=3.58 min, $[M+H]^{30}$ =406.

E. Preparation of 8-bromo-7-(4-chlorophenyl)-2-((6-(trifluoromethyl)pyridin-3-yl)methyl)-[1,2,4]triazolo[4,3-c]pyrimidin-3(2H)-one

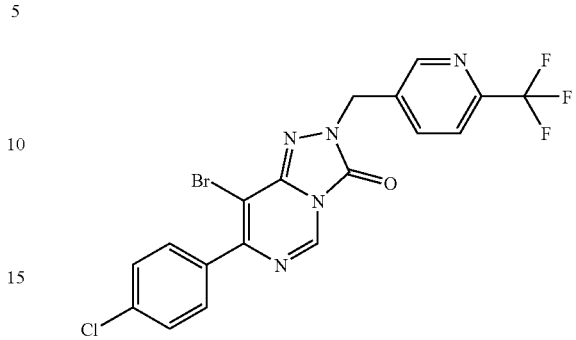

To a solution of 7-(4-chlorophenyl)-2-((6-(trifluoromethyl)pyridin-3-yl)methyl)-[1,2,4]triazolo[4,3-c]pyrimidin-3(2H)-one (40.5 mg, 0.10 mmol) in dichloroethane (5 mL) at room temperature under argon was added calcium carbonate (10.0 mg, 0.10 mmol) and N,N,N-trimethyl-1-phenylmethanaminium tribromide (39.0 mg, 0.10 mmol). The resulting suspension was stirred and heated at 70° C. under argon for 2 h. Analysis by HPLC/MS indicated that most of the starting material had been consumed. After the reaction mixture was cooled to room temperature, the product was purified by silica gel column chromatography eluted with ethyl acetate-dichloromethane. This provided the title compound (43.6 mg) as a solid. HPLC/MS (methanol-water with 10 mM $NH_4OAc$): retention time=3.67 min, $[M+H]^+$486.

F. Preparation of 7-(4-chlorophenyl)-8-(pyridin-4-yl)-2-((6-(trifluoromethyl)pyridin-3-yl)methyl)-[1,2,4]triazolo[4,3-c]pyrimidin-3(2H)-one

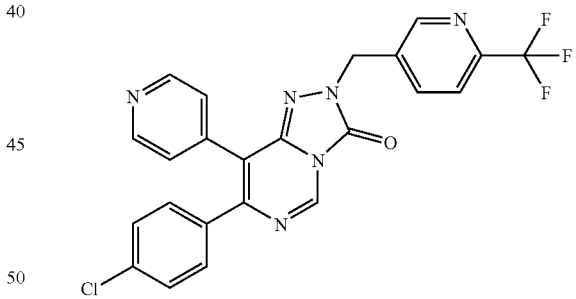

A suspension of 8-bromo-7-(4-chlorophenyl)-2-((6-(trifluoromethyl)pyridin-3-yl)methyl)-[1,2,4]triazolo[4,3-c]pyrimidin-3(2H)-one (24 mg, 0.05 mmol), pyridine-4-boronic acid (51 mg, 0.25 mmol), $K_3PO_4$ (53 mg, 0.25 mmol), and Pd(dppf)$Cl_2 \cdot CH_2Cl_2$ (16 mg, 0.02 mmol) in THF (0.5 mL) at room temperature was degassed by bubbling with argon for 1 min. This was then stirred and heated at 100° C. in a sealed vessel for 3 h. Analysis by HPLC/MS indicated that starting material had been consumed. After the reaction mixture was cooled to room temperature, the solvent was removed under reduced pressure. The product was purified by silica gel column chromatography eluted with ethyl acetate-hexanes. This provided the title compound (5.3 mg) as a yellow solid. HPLC/MS (methanol-water with 10 mM $NH_4OAc$): retention time=3.38 min, $[M+H]^{30}$ =483.

Example 6

Preparation of 7-(4-chlorophenyl)-8-(4-(hydroxymethyl)phenyl)-2-((6-(trifluoromethyl)pyridin-3-yl)methyl)-[1,2,4]triazolo[4,3-c]pyrimidin-3(2H)-one

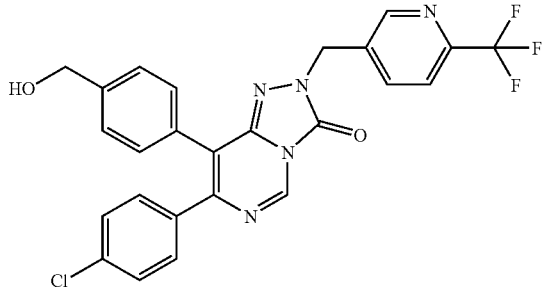

A suspension of 8-bromo-7-(4-chlorophenyl)-2-((6-(trifluoromethyl)pyridin-3-yl)methyl)-[1,2,4]triazolo[4,3-c]pyrimidin-3(2H)-one (48 mg, 0.10 mmol), 4-(hydroxymethyl)phenylboronic acid (46 mg, 0.30 mmol), $K_3PO_4$ (63 mg, 0.30 mmol), and Pd(dppf)Cl$_2$·CH$_2$Cl$_2$ (20 mg, 0.025 mmol) in THF (1 mL) at room temperature was degassed by bubbling with argon for 1 min. This was then stirred and heated at 100° C. in a sealed vessel for 3 h. Analysis by HPLC/MS indicated that starting material had been consumed. After the reaction mixture was cooled to room temperature, the solvent was removed under reduced pressure. The crude product was purified by silica gel column chromatography eluted with ethyl acetate-hexanes. This provided the title compound (6.7 mg) as a light yellow solid. HPLC/MS (methanol-water with 10 mM NH$_4$OAc): retention time=3.53 min, [M+H]$^{30}$=512.

Example 7

Preparation of 7-(4-chlorophenyl)-5-methyl-8-(pyridin-4-yl)-2-((6-(trifluoromethyl)pyridin-3-yl)methyl)-[1,2,4]triazolo[4,3-c]pyrimidin-3(2H)-one

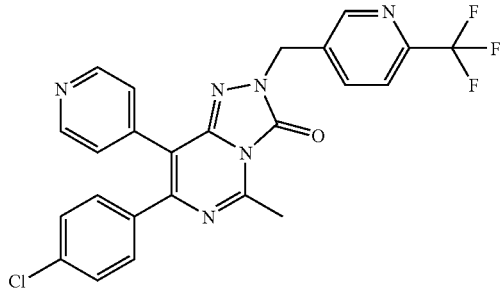

A. Preparation of 4-chloro-6-hydrazinyl-2-methylpyrimidine

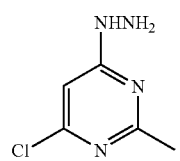

To a stirred solution of 4,6-dichloro-2-methylpyrimidine (1.63 g, 10.0 mmol) in THF (25 mL) at room temperature under argon was added H$_2$NNH$_2$ (0.64 g, 20.0 mmol). The reaction mixture was stirred at room temperature under argon overnight. Analysis by HPLC/MS indicated that the reaction was complete. The solvent was evaporated, and the residue was coevaporated with toluene (2×5 mL) then THF (5 mL), and then dried under vacuum. The crude title compound was used directly in the next step. HPLC/MS: retention time=0.77 min.

B. Preparation of 7-chloro-5-methyl-2-((6-(trifluoromethyl)pyridin-3-yl)methyl)-[1,2,4]triazolo[4,3-c]pyrimidin-3(2H)-one

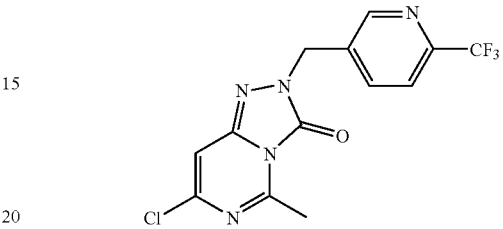

To a stirred solution of triphosgene (2.86 g, 9.66 mmol) in THF (10 mL) at room temperature under argon was added a suspension of 4-chloro-6-hydrazinyl-2-methylpyrimidine (10.0 mmol) in THF (15 mL). The reaction mixture was stirred overnight. Analysis by HPLC/MS indicated that no starting material remained. Solvent was removed under reduced pressure. DMF (5 mL) was added to the residue, followed by K$_2$CO$_3$ (2.76 g, 20.0 mmol) and 5-(chloromethyl)-2-(trifluoromethyl)pyridine (2.34 g, 12.0 mmol). The resulting mixture was heated at 60° C. for 2 h, after which time analysis by HPLC/MS indicated that the reaction was complete. After cooling the reaction mixture to room temperature, water (20 mL) was added. The resulting mixture was extracted with EtOAc (2×20 mL). The combined organic layers were washed with saturated aqueous NaCl (20 mL), then dried over Na$_2$SO$_4$, filtered and concentrated under reduced pressure. The residue was purified by column chromatography eluted with ethyl acetate-dichloromethane to obtain 2.1 g of the title compound a solid. HPLC/MS: retention time=2.82 min, [M+H]$^{30}$=344.

C. Preparation of 7-(4-chlorophenyl)-5-methyl-2-((6-(trifluoromethyl)pyridin-3-yl)methyl)-[1,2,4]triazolo[4,3-c]pyrimidin-3(2H)-one

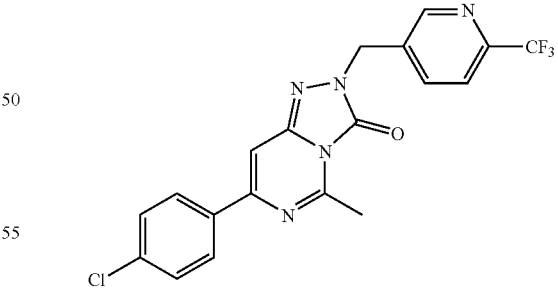

To a stirred solution of 7-chloro-5-methyl-2-((6-(trifluoromethyl)pyridin-3-yl)methyl)-[1,2,4]triazolo[4,3-c]pyrimidin-3(2H)-one (2.0 g, 5.8 mmol), 4-chlorophenylboronic acid (1.2 g, 7.58 mmol), and tetrakis(triphenylphosphine)palladium (0.67 g, 0.58 mmol) in toluene (25 mL) at room temperature under argon was added aqueous Na$_2$CO$_3$ solution (2 M, 5.8 mL, 11.6 mmol). The resulting reaction mixture was stirred at 100° C. under argon overnight, after which time analysis by HPLC/MS indicated that the reaction was complete. After cooling the reaction mixture to room temperature, water (50 mL) was added. The resulting mixture was extracted with EtOAc (50 mL). The organic layer was washed with saturated aqueous NaCl, then dried over $Na_2SO_4$, filtered and concentrated under reduced pressure. The residue was purified by triturating with MeOH (15 mL) to obtain 1.95 g of the title compound as an off-white solid. HPLC/MS: retention time=3.85 min, $[M+H]^{30}$ =420.

D. Preparation of 8-bromo-7-(4-chlorophenyl)-5-methyl-2-((6-(trifluoromethyl)pyridin-3-yl)methyl)-[1,2,4]triazolo[4,3-c]pyrimidin-3(2H)-one

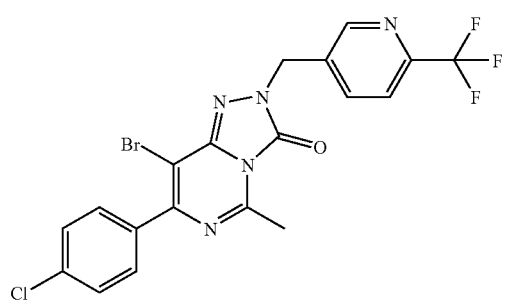

To a solution of 7-(4-chlorophenyl)-5-methyl-2-((6-(trifluoromethyl)pyridin-3-yl)methyl)-[1,2,4]triazolo[4,3-c]pyrimidin-3(2H)-one (210 mg, 0.50 mmol) in dichloromethane (10 mL) and methanol (10 mL) at room temperature under argon was added calcium carbonate (50.0 mg, 0.50 mmol) and N,N,N-trimethyl-1-phenylmethanaminium tribromide (195 mg, 0.50 mmol). The resulting suspension was stirred and heated at 60° C. under argon for 1 h. Analysis by HPLC/MS indicated that the starting material had been consumed. The solvents were removed under reduced pressure, and water (25 mL) was added. After stirring at room temperature for 30 min, the solid product was collected by filtration and further washed with water (2×10 mL). After drying, the title compound (273 mg) was obtained as an off-white solid. HPLC/MS: retention time=3.84 min, $[M+H]^{30}$ =500.

E. Preparation of 7-(4-chlorophenyl)-5-methyl-8-(pyridin-4-yl)-2-((6-(trifluoromethyl)pyridin-3-yl)methyl)-[1,2,4]triazolo[4,3-c]pyrimidin-3(2H)-one

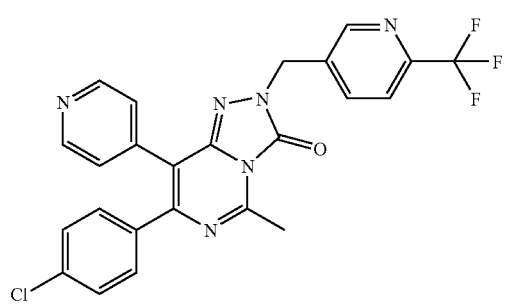

A suspension of 8-bromo-7-(4-chlorophenyl)-5-methyl-2-((6-(trifluoromethyl)pyridin-3-yl)methyl)-[1,2,4]triazolo[4,3-c]pyrimidin-3(2H)-one (50 mg, 0.10 mmol), pyridine-4-boronic acid (62 mg, 0.30 mmol), $K_3PO_4$ (64 mg, 0.30 mmol), and $Pd(dppf)Cl_2 \cdot CH_2Cl_2$ (16 mg, 0.02 mmol) in THF (1 mL) at room temperature was degassed by bubbling with argon for 2 min. This was then stirred and heated at 100° C. in a sealed vessel for 6 h. Analysis by HPLC/MS indicated that the starting material had been consumed. After the reaction mixture was cooled to room temperature, the solvent was removed under reduced pressure. The crude product was purified by silica gel column chromatography eluted with ethyl acetate-hexanes to obtain the title compound (22.6 mg) as a yellow solid. HPLC/MS (methanol-water with 10 mM $NH_4OAc$): retention time=3.61 min, $[M+H]^{30}$ =497.

Example 8

Preparation of 7-(4-chlorophenyl)-5-(methylthio)-8-phenyl-2-((6-(trifluoromethyl)pyridin-3-yl)methyl)-[1,2,4]triazolo[4,3-c]pyrimidin-3(2H)-one

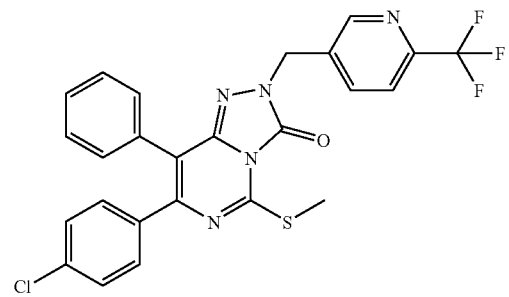

A. Preparation of 4-chloro-6-(4-chlorophenyl)-2-(methylthio)-5-phenylpyrimidine

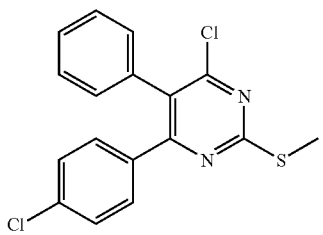

To a mixture of 4,6-dichloro-2-(methylthio)-5-phenylpyrimidine (2.71 g, 10.0 mmol), 4-chlorophenylboronic acid (1.72 g, 11.0 mmol) and tetrakis(triphenylphosphine)palladium (578 mg, 0.50 mmol) in toluene (25 mL) at room temperature under argon was added aqueous $Na_2CO_3$ solution (2 M, 10 mL, 20.0 mmol). The resulting reaction mixture was stirred at 100° C. under argon for 6 h, after which time analysis by HPLC/MS indicated that the reaction was complete. After cooling the reaction mixture to room temperature, water (50 mL) was added. The resulting mixture was extracted with EtOAc (2×25 mL). The combined organic layers were washed with saturated aqueous NaCl, then dried over $Na_2SO_4$, filtered and concentrated under reduced pressure. The residue was purified by reverse phase preparative HPLC to obtain 1.22 g of the title compound as a white solid. HPLC/MS: retention time=4.32 min, $[M+H]^{30}$ =347.

B. Preparation of 4-(4-chlorophenyl)-6-hydrazinyl-2-(methylthio)-5-phenylpyrimidine

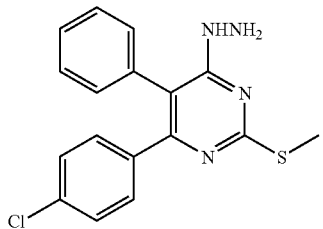

To a stirred solution of 4-chloro-6-(4-chlorophenyl)-2-(methylthio)-5-phenylpyrimidine (1.22 g, 3.52 mmol) in THF (15 mL) at room temperature under argon was added H$_2$NNH$_2$ (340 mg, 10.5 mmol). The reaction mixture was heated at 60° C. under argon for 2 h. Analysis by HPLC/MS indicated that the reaction was complete. The solvent was evaporated, and the resulting residue was coevaporated with toluene (2×5 mL) and then dichloromethane (2×10 mL), then dried under vacuum. The crude title compound was used directly in the next step. HPLC/MS: retention time=2.73 min, [M+H]$^{30}$ =343.

C. Preparation of 7-(4-chlorophenyl)-5-(methylthio)-8-phenyl-[1,2,4]triazolo[4,3-c]pyrimidin-3(2H)-one

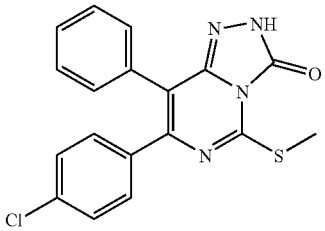

To a stirred solution of triphosgene (2.08 g, 7.04 mmol) in THF (10 mL) at room temperature under argon was added a suspension of 4-(4-chlorophenyl)-6-hydrazinyl-2-(methylthio)-5-phenylpyrimidine (3.52 mmol) in THF (5 mL). The reaction mixture was stirred overnight. Analysis by HPLC/MS indicated that no starting material remained. The reaction mixture was cooled to 0° C. in an ice bath and ice water (50 mL) was added. After stirring for 30 min, the solid precipitate was collected and further washed with water (50 mL). After drying, the title compound (1.25 g) was obtained as an off-white solid. HPLC/MS: retention time=3.51 min, [M+H]$^{30}$ =369.

D. Preparation of 7-(4-chlorophenyl)-5-(methylthio)-8-phenyl-2-((6-(trifluoromethyl)pyridin-3-yl)methyl)-[1,2,4]triazolo[4,3-c]pyrimidin-3(2H)-one

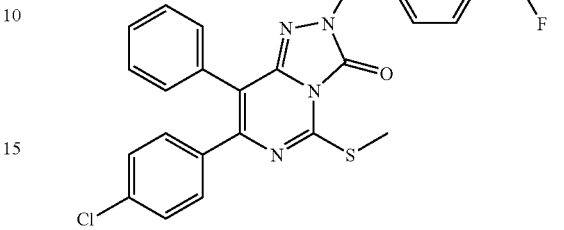

To a stirred solution of 7-(4-chlorophenyl)-5-(methylthio)-8-phenyl-[1,2,4]triazolo[4,3-c]pyrimidin-3(2H)-one (100 mg, 0.27 mmol) in DMF (2 mL) at room temperature under argon was added 5-(chloromethyl)-2-(trifluoromethyl)pyridine (64.4 mg, 0.33 mmol), followed by K$_2$CO$_3$ (74.5 mg, 0.54 mmol). The resulting mixture was stirred at room temperature for 5 h. The crude product was purified by silica gel column chromatography eluted with ethyl acetate—hexanes, then lyophilized from 1,4-dioxane, to obtain the title compound (107.5 mg) as an off-white lyophilate. HPLC/MS: retention time=4.24 min, [M+H]$^{30}$ =528.

Example 9

Preparation of 7-(4-chlorophenyl)-5-(methylthio)-8-phenyl-2-(4-(trifluoromethyl)benzyl)-[1,2,4]triazolo[4,3-c]pyrimidin-3(2H)-one

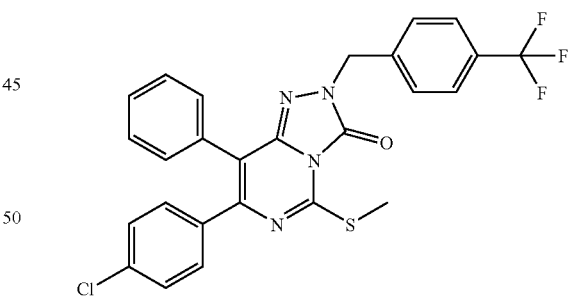

To a stirred solution of 7-(4-chlorophenyl)-5-(methylthio)-8-phenyl-[1,2,4]triazolo[4,3-c]pyrimidin-3(2H)-one (100 mg, 0.27 mmol) in DMF (2 mL) at room temperature under argon was added 4-trifluoromethylbenzyl bromide (77.7 mg, 0.33 mmol), followed by K$_2$CO$_3$ (74.5 mg, 0.54 mmol). The resulting mixture was stirred at room temperature for 5 h. Insoluble material was filtered off and the filtrate was purified by silica gel column chromatography eluted with ethyl acetate-hexanes, then lyophilized from 1,4-dioxane, to obtain the title compound (112 mg) as an off-white lyophilate. HPLC/MS: retention time=4.50 min, [M+H]$^{30}$ =527.

Examples 10 and 11

Preparation of 7-(4-chlorophenyl)-5-hydroxy-8-phenyl-2-((6-(trifluoromethyl)pyridin-3-yl)methyl)-[1,2,4]triazolo[4,3-c]pyrimidin-3(2H)-one and 7-(4-chlorophenyl)-5-methoxy-8-phenyl-2-((6-(trifluoromethyl)pyridin-3-yl)methyl)-[1,2,4]triazolo[4,3-c]pyrimidin-3(2H)-one.

Examples 12 and 13

Preparation of 7-(4-chlorophenyl)-5-hydroxy-8-phenyl-2-(4-(trifluoromethyl)benzyl)-[1,2,4]triazolo[4,3-c]pyrimidin-3(2H)-one and 7-(4-chlorophenyl)-5-methoxy-8-phenyl-2-(4-(trifluoromethyl)benzyl)-[1,2,4]triazolo[4,3-c]pyrimidin-3(2H)-one.

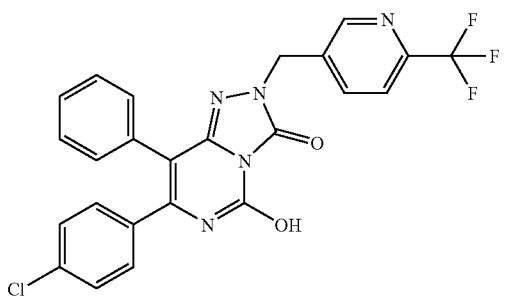

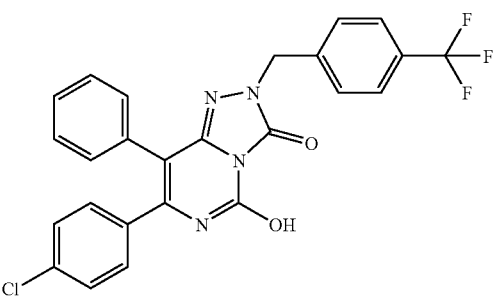

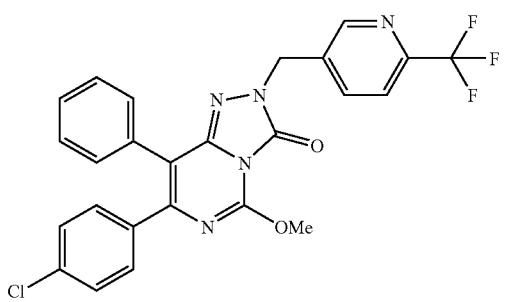

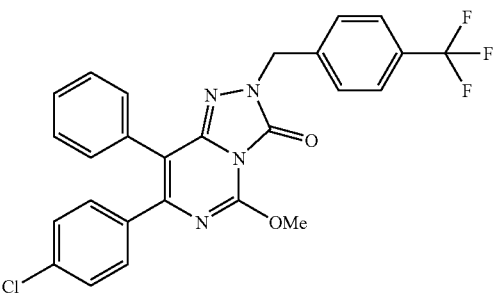

To a stirred solution of 7-(4-chlorophenyl)-5-(methylthio)-8-phenyl-2-((6-(trifluoromethyl)pyridin-3-yl)methyl)-[1,2,4]triazolo[4,3-c]pyrimidin-3(2H)-one (16 mg, 0.03 mmol) in THF (1 mL) at room temperature under argon was added mCPBA (20 mg, 0.09 mmol). The resulting mixture was stirred at room temperature for 1 h. Analysis by HPLC/MS indicated that no starting material remained. Next, NaHSO$_3$ (20 mg) was added to the reaction mixture. After stirring for 1 h, methanol (0.5 mL) was added to the reaction mixture. The reaction mixture was stirred at 50° C. for 2 h, and then the solvents were removed under reduced pressure. The residue was purified by reverse phase preparative HPLC to obtain the title compounds (7.3 mg and 6.5 mg, respectively) as off-white solids. HPLC/MS: retention times=3.61 and 4.02 min, respectively; [M+H]$^{30}$ =498 and 512, respectively.

To a stirred solution of 7-(4-chlorophenyl)-5-(methylthio)-8-phenyl-2-(4-(trifluoromethyl)benzyl)-[1,2,4]triazolo[4,3-c]pyrimidin-3(2H)-one (25 mg, 0.048 mmol) in THF (1 mL) at room temperature under argon was added mCPBA (32 mg, 0.143 mmol). The resulting mixture was stirred at room temperature for 1 h. Analysis by HPLC/MS indicated that no starting material remained. Next, solid NaHSO$_3$ (25 mg) was added to the reaction mixture. After stirring for 1 h, methanol (0.9 mL) and water (0.1 mL) were added to the reaction mixture. The mixture was stirred at room temperature overnight, and then the solvents were removed under reduced pressure. The residue was purified by reverse phase preparative HPLC to obtain the title compounds (12.4 mg and 2.4 mg, respectively) as off-white solids. HPLC/MS: retention times=3.90 and 4.25 min, respectively; [M+H]$^{30}$ =497 and 511, respectively.

Example 14

Preparation of 1-(7,8-bis(4-chlorophenyl)-2-ethyl-3-oxo-2,3-dihydro-[1,2,4]triazolo[4,3-c]pyrimidin-5-yl)-3-(ethylamino)azetidine-3-carboxamide

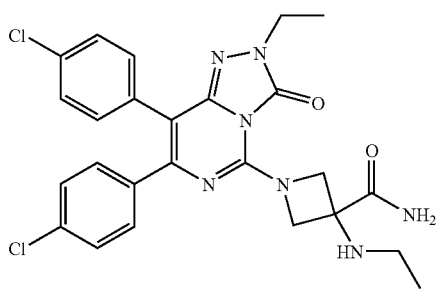

A. Preparation of 5-bromo-6-chloropyrimidine-2,4(1H,3H)-dione

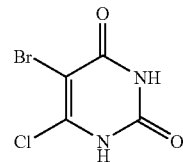

To a stirring and refluxing solution of 6-chloropyrimidine-2,4(1H,3H)-dione (10.0 g, 68.25 mmol) in water (100 mL) was added bromine (4 mL, 79.84 mmol)) over 10 min. The colorless precipitate that formed was collected by filtration, washed with water (50 mL×2), and dried in a vacuum oven at 50° C. overnight, to obtain 9.4 g of the title compound as a white solid. HPLC/MS: retention time=1.05 min, $[M+H]^{30}$ =225.

B. Preparation of 1,3-dibenzyl-5-bromo-6-chloropyrimidine-2,4(1H,3H)-dione

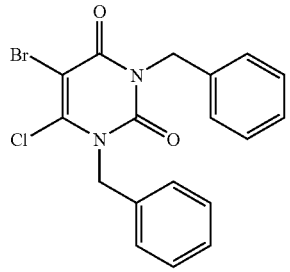

To a stirring solution of 5-bromo-6-chloropyrimidine-2,4(1H,3H)-dione (9.4 g, 41.7 mmol) in DMF (100 mL) at room temperature under argon was added $K_2CO_3$ (12.7 g, 91.8 mmol), followed by benzyl bromide (10.5 mL, 88.3 mmol). The reaction mixture was stirred at 75° C. for 1.5 h. After the reaction mixture was cooled to room temperature, water (100 mL) and EtOAc (150 mL) were added. The layers were separated. The organic layer was washed with water (50 mL×2), followed by saturated aqueous NaCl (50 mL), then dried ($MgSO_4$) and concentrated at reduced pressure to obtain crude product. This crude product was passed through a bed of silica gel eluted with $CH_2Cl_2$ to obtain 16.5 g of the title compound as a white solid. HPLC/MS: retention time=3.818 min, $[M+H]^{30}$ =405.

C. Preparation of 1,3-dibenzyl-5,6-bis(4-chlorophenyl)pyrimidine-2,4(1H,3H)-dione

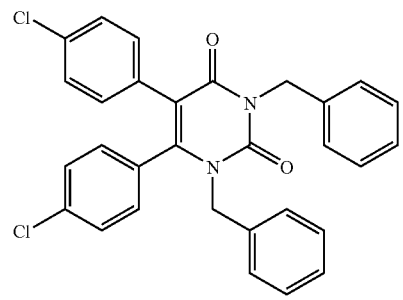

To a solution of 1,3-dibenzyl-5-bromo-6-chloropyrimidine-2,4(1H,3H)-dione (6.0 g, 14.8 mmol) in toluene (50 mL) at room temperature under argon was added 4-chlorophenylboronic acid (7.0 g, 44.77 mmol), tetrakis(triphenylphosphine)palladium (1.03 g, 0.89 mmol), and a solution of $Na_2CO_3$ (4.7 g, 44.34 mmol) in water (10 ml). The resulting suspension was stirred at reflux under argon for 6 h. After the reaction mixture was cooled to room temperature, water (50 mL) and EtOAc (75 mL) were added. The layers were separated. The organic layer was dried ($MgSO_4$), filtered, and concentrated under reduced pressure. The crude product was purified by silica gel column chromatography eluted 15% ethyl acetate-hexanes to obtain 7.2 g of the title compound as a white solid. HPLC/MS (MeOH-water with 10 mM $NH_4OAc$): retention time=4.241 min, $[M+H]^{30}$ =513.

D. Preparation of 5,6-bis(4-chlorophenyl)pyrimidine-2,4(1H,3H)-dione

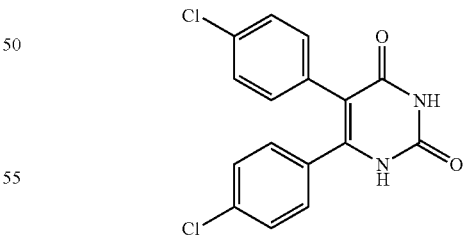

To a solution of 1,3-dibenzyl-5,6-bis(4-chlorophenyl)pyrimidine-2,4(1H,3H)-dione (7.2 g, 14.0 mmol) in toluene (70 mL) was added $AlCl_3$ (4.7 g, 35.2 mmol) under argon. The reaction mixture was stirred in an oil bath preheated at 85° C. for 2 h. The reaction mixture was cooled to room temperature and then poured onto crushed ice (100 g). The precipitate formed was collected by filtration, washed with water (30 mL×2) then ether (40 mL), and dried in a vacuum oven at 40° C. to obtain 4.2 g of the title compound as a brown solid. HPLC/MS (MeOH-water with 10 mM NH₄OAc): retention time=3.433 min, [M+H]³⁰ =333.

E. Preparation of 2,4-dichloro-5,6-bis(4-chlorophenyl)pyrimidine

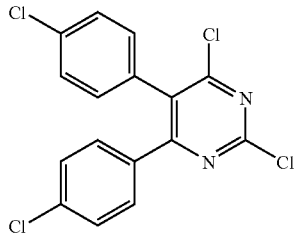

A mixture of 5,6-bis(4-chlorophenyl)pyrimidine-2,4(1H, 3H)-dione (2.8 g, 8.4 mmol) and POCl₃ (15 mL) was stirred at reflux for 3 h. The reaction mixture was cooled to room temperature, and excess POCl₃ was removed under reduced pressure on a rotary evaporator to obtain a gum. This gum was cooled in an ice bath and water (20 mL) was added. The pH of this mixture was adjusted to pH 6 with aqueous NaHCO₃ solution. The resulting mixture was extracted with EtOAc (2×25 mL). The combined organic extracts were washed with water and saturated aqueous NaCl, then dried (MgSO₄), filtered, and concentrated under reduced pressure. The crude product was purified by silica gel column chromatography eluted with 15% ethyl acetate-hexanes to obtain 2.75 g of the title compound as a white solid. HPLC/MS: retention time=4.366 min, [M+H]³⁰ =369.

F. Preparation of 2-chloro-4,5-bis(4-chlorophenyl)-6-hydrazinylpyrimidine

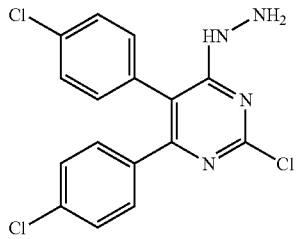

2,4-Dichloro-5,6-bis(4-chlorophenyl)pyrimidine (1.8 g, 4.86 mmol) was dissolved in pyridine (5 mL) and hydrazine monohydrate (0.26 mL, 5.36 mmol) was added. The reaction mixture was stirred at room temperature for 30 min. The reaction mixture was then diluted with water (10 mL) and extracted with EtOAc (10 mL×2). The combined organic extracts were washed with water, followed by saturated aqueous NaCl, dried (MgSO₄), and concentrated at reduced pressure to obtain 1.7 g of the title compound, as a mixture with its regioisomer, as a yellow solid. HPLC/MS: title compound retention time=3.261 min, [M+H]³⁰ =365; regioisomer retention time 3.385 min.

G. Preparation of 5-chloro-7,8-bis(4-chlorophenyl)-[1,2,4]triazolo[4,3-c]pyrimidin-3(2H)-one

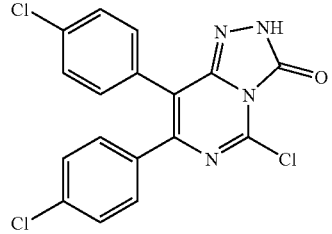

To a solution of a mixture of 2-chloro-4,5-bis(4-chlorophenyl)-6-hydrazinylpyrimidine and its regioisomer prepared above (900 mg, 2.46 mmol) in THF (10 mL) at room temperature under argon was added triphosgene (1.46 g, 4.91 mmol). The reaction mixture was stirred at room temperature overnight. The reaction mixture was cooled in an ice bath and carefully quenched with water (10 mL) and then extracted with EtOAc (15 mL×2). The combined organic extracts were washed with water and then saturated aqueous NaCl. The organic layer was dried (MgSO₄), filtered, and concentrated under reduced pressure. The crude product was purified by silica gel column chromatography eluted with 20% ethyl acetate-hexanes to obtain 400 mg of the title compound as a yellow solid. HPLC/MS: retention time=3.923 min, [M+H]⁺ =391; ¹H NMR (DMSO-d₆, 500 MHz): δ 12.68 (s, 1H), 7.39 (d, J=8.25 Hz, 2H), 7.31 (d, J=8.25 Hz, 2H), 7.23 (d, J=8.8 Hz, 2H), 7.21 (d, J=8.8 Hz, 2H). Regioisomeric product derived from starting material regioisomeric impurity: HPLC/MS: retention time=3.545 min.

H. Preparation of 1-(7,8-bis(4-chlorophenyl)-3-oxo-2,3-dihydro-[1,2,4]triazolo[4,3-c]pyrimidin-5-yl)-3-(ethylamino)azetidine-3-carboxamide

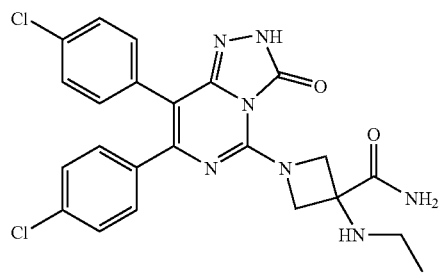

To a stirred suspension of 3-(ethylamino)azetidine-3-carboxamide (25 mg, 0.17 mmol) in EtOH (1.0 mL) at room temperature under argon was added N,N-diisopropylethylamine (60 mg, 0.46 mmol). The reaction mixture was stirred at room temperature for 10 min to obtain a clear solution to which was added 5-chloro-7,8-bis(4-chlorophenyl)-[1,2,4]triazolo[4,3-c]pyrimidin-3(2H)-one (60 mg, 0.15 mmol). The reaction mixture was stirred at 60° C. in a pre-heated oil bath for 5 min. The reaction mixture was then concentrated under reduced pressure, and the residue was dissolved in CH₂Cl₂ (5 mL). The resulting mixture was washed with water (2 mL×2), dried (MgSO₄), and concentrated under reduced pressure to obtain the crude product. This crude product was purified by I. Preparation of 1-(7,8-bis(4-chlorophenyl)-2-ethyl-3-oxo-2,3-dihydro-[1,2,4]triazolo[4,3-c]pyrimidin-5-yl)-3-(ethylamino)azetidine-3-carboxamide

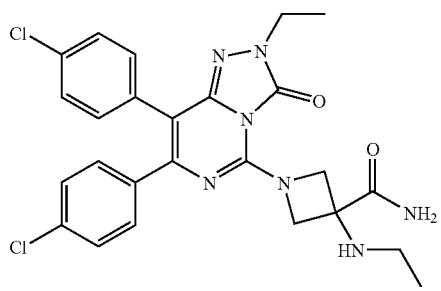

To a solution of 1-(7,8-bis(4-chlorophenyl)-3-oxo-2,3-dihydro-[1,2,4]triazolo[4,3-c]pyrimidin-5-yl)-3-(ethylamino)azetidine-3-carboxamide (25 mg, 0.05 mmol) in DMF (0.5 mL) at room temperature under argon was added $K_2CO_3$ (10 mg, 0.07 mmol), followed by iodoethane (10 mg, 0.064 mmol). The reaction mixture was stirred at 60° C. in a preheated oil bath for 30 min. After the reaction mixture was cooled to room temperature, water (5 mL) and EtOAc (5 mL) were added. The layers were separated. The organic layer was dried ($MgSO_4$), filtered, and concentrated under reduced pressure. The crude product thus obtained was purified by preparative reverse phase HPLC (without TFA) to obtain 21.5 mg of the title compound as a white solid. HPLC/MS: retention time=3.465 min, $[M+H]^{30}$ =526.

Example 15

Preparation of 1-(7,8-bis(4-chlorophenyl)-2-methyl-3-oxo-2,3-dihydro-[1,2,4]triazolo[4,3-c]pyrimidin-5-yl)-3-(ethylamino)azetidine-3-carboxamide

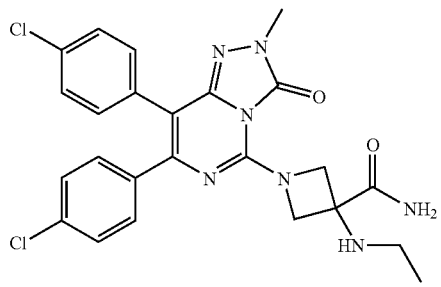

The title compound was prepared by coupling 1-(7,8-bis(4-chlorophenyl)-3-oxo-2,3-dihydro-[1,2,4]triazolo[4,3-c]pyrimidin-5-yl)-3-(ethylamino)azetidine-3-carboxamide with iodomethane in a manner analogous to that in which 1-(7,8-bis(4-chlorophenyl)-2-ethyl-3-oxo-2,3-dihydro-[1,2,4]triazolo[4,3-c]pyrimidin-5-yl)-3-(ethylamino)azetidine-3-carboxamide was prepared. HPLC/MS: retention time 3.318 min, $[M+H]^{30}$ =512.

Example 16

Preparation of 1-(7,8-bis(4-chlorophenyl)-2-methyl-3-oxo-2,3-dihydro-[1,2,4]triazolo[4,3-c]pyrimidin-5-yl)-3-(ethyl(methyl)amino)azetidine-3-carboxamide

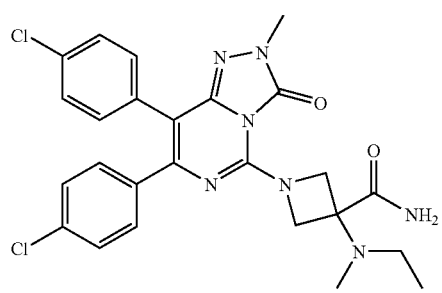

The title compound was isolated as a side-product of the preparation of 1-(7,8-bis(4-chlorophenyl)-2-methyl-3-oxo-2,3-dihydro-[1,2,4]triazolo[4,3-c]pyrimidin-5-yl)-3-(ethylamino)azetidine-3-carboxamide. HPLC/MS: retention time=3.435 min, $[M+H]^{30}$ =526.

Example 17

Preparation of 1-(7,8-bis(4-chlorophenyl)-3-oxo-2-(4-(trifluoromethyl)benzyl)-2,3-dihydro-[1,2,4]triazolo[4,3-c]pyrimidin-5-yl)-3-(ethylamino)azetidine-3-carboxamide

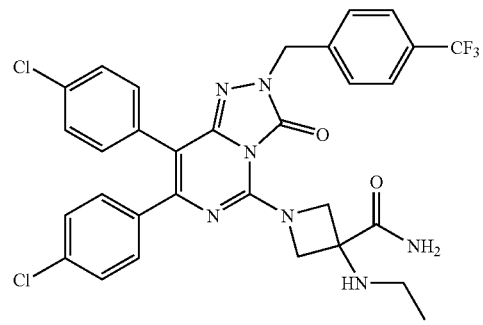

The title compound was prepared by coupling 1-(7,8-bis(4-chlorophenyl)-3-oxo-2,3-dihydro-[1,2,4]triazolo[4,3-c]pyrimidin-5-yl)-3-(ethylamino)azetidine-3-carboxamide with 4-trifluoromethylbenzyl bromide in a manner analogous to that in which 1-(7,8-bis(4-chlorophenyl)-2-ethyl-3-oxo-2,3-dihydro-[1,2,4]triazolo[4,3-c]pyrimidin-5-yl)-3-(ethylamino)azetidine-3-carboxamide was prepared. HPLC/MS: retention time=3.866 min, $[M+H]^{30}$ =656.

Example 18

Preparation of 1-(7,8-bis(4-chlorophenyl)-3-oxo-2-(4-(trifluoromethyl)benzyl)-2,3-dihydro-[1,2,4]triazolo[4,3-c]pyrimidin-5-yl)-4-(ethylamino)piperidine-4-carboxamide

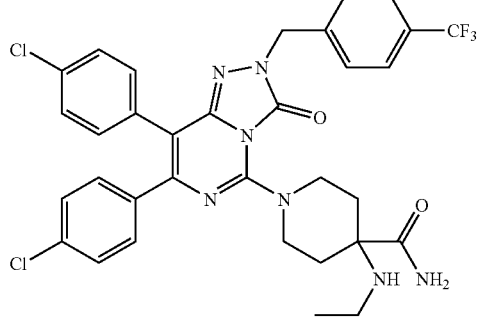

The title compound was prepared in two steps from 5-chloro-7,8-bis(4-chlorophenyl)-[1,2,4]triazolo[4,3-c]pyrimidin-3(2H)-one by nucleophilic displacement of chloride with the requisite amine, followed by alkylation with 4-trifluoromethylbenzyl bromide, in a manner analogous to that in which 1-(7,8-bis(4-chlorophenyl)-2-ethyl-3-oxo-2,3-dihydro-[1,2,4]triazolo[4,3-c]pyrimidin-5-yl)-3-(ethylamino)azetidine-3-carboxamide was prepared. HPLC/MS: retention time=3.961 min, $[M+H]^{30}$ =684.

Example 19

Preparation of 7,8-bis(4-chlorophenyl)-5-(morpholin-1-yl)-2-(4-(trifluoromethyl)benzyl)-[1,2,4]triazolo[4,3-c]pyrimidin-3(2H)-one

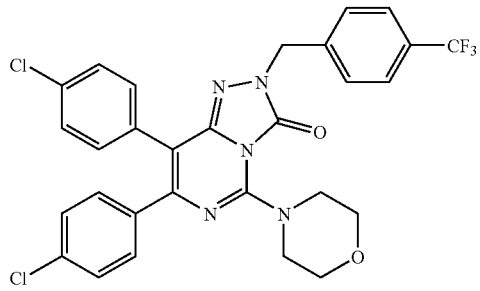

The title compound was prepared in two steps from 5-chloro-7,8-bis(4-chlorophenyl)-[1,2,4]triazolo[4,3-c]pyrimidin-3(2H)-one by nucleophilic displacement of chloride with the requisite amine, followed by alkylation with 4-trifluoromethylbenzyl bromide, in a manner analogous to that in which 1-(7,8-bis(4-chlorophenyl)-2-ethyl-3-oxo-2,3-dihydro-[1,2,4]triazolo[4,3-c]pyrimidin-5-yl)-3-(ethylamino)azetidine-3-carboxamide was prepared. HPLC/MS: retention time=4.67 min, $[M+H]^{30}$ =600.

Example 20

Preparation of 7,8-bis(4-chlorophenyl)-5-(4-methylpiperazin-1-yl)-2-(4-(trifluoromethyl)benzyl)-[1,2,4]triazolo[4,3-c]pyrimidin-3(2H)-one

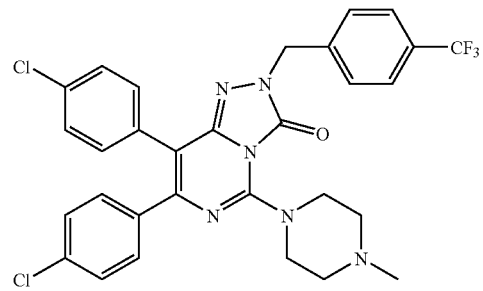

The title compound was prepared in two steps from 5-chloro-7,8-bis(4-chlorophenyl)-[1,2,4]triazolo[4,3-c]pyrimidin-3(2H)-one by nucleophilic displacement of chloride with the requisite amine, followed by alkylation with 4-trifluoromethylbenzyl bromide, in a manner analogous to that in which 1-(7,8-bis(4-chlorophenyl)-2-ethyl-3-oxo-2,3-dihydro-[1,2,4]triazolo[4,3-c]pyrimidin-5-yl)-3-(ethylamino)azetidine-3-carboxamide was prepared. HPLC/MS: retention time=3.90 min, $[M+H]^{30}$ =613.

Example 21

Preparation of 7,8-bis(4-chlorophenyl)-2-ethyl-5-morpholino-[1,2,4]triazolo[4,3-c]pyrimidin-3(2H)-one

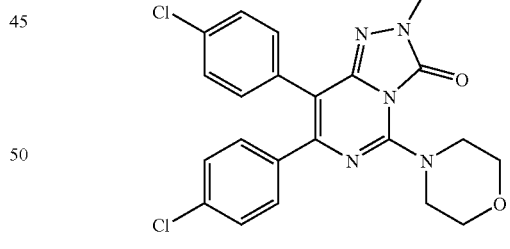

The title compound was prepared in two steps from 5-chloro-7,8-bis(4-chlorophenyl)-[1,2,4]triazolo[4,3-c]pyrimidin-3(2H)-one by nucleophilic displacement of chloride with the requisite amine, followed by alkylation with iodoethane, in a manner analogous to that in which 1-(7,8-bis(4-chlorophenyl)-2-ethyl-3-oxo-2,3-dihydro-[1,2,4]triazolo[4,3-c]pyrimidin-5-yl)-3-(ethylamino)azetidine-3-carboxamide was prepared. HPLC/MS: retention time=4.306 min, $[M+H]^{30}$ =470.

Example 22

Preparation of 7,8-bis(4-chlorophenyl)-2-ethyl-5-(4-(trifluoromethyl)benzylamino)-[1,2,4]triazolo[4,3-c]pyrimidin-3(2H)-one

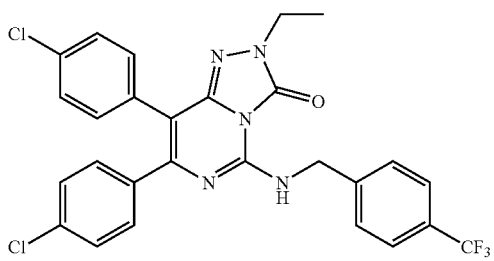

The title compound was prepared in two steps from 5-chloro-7,8-bis(4-chlorophenyl)-[1,2,4]triazolo[4,3-c]pyrimidin-3(2H)-one by nucleophilic displacement of chloride with the requisite amine, followed by alkylation with iodoethane, in a manner analogous to that in which 1-(7,8-bis(4-chlorophenyl)-2-ethyl-3-oxo-2,3-dihydro-[1,2,4]triazolo[4,3-c]pyrimidin-5-yl)-3-(ethylamino)azetidine-3-carboxamide was prepared. HPLC retention time=4.91 min; HPLC/MS: $[M+H]^{30}$=558.

Example 23

Preparation of 7,8-bis(4-chlorophenyl)-2-methyl-5-(4-(trifluoromethyl)benzylamino)-[1,2,4]triazolo[4,3-c]pyrimidin-3(2H)-one

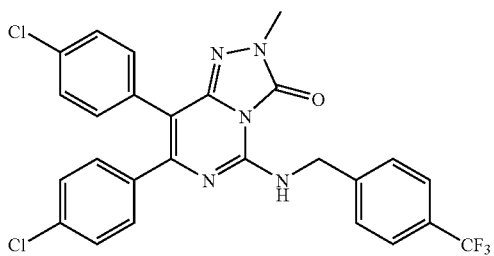

The title compound was prepared in two steps from 5-chloro-7,8-bis(4-chlorophenyl)-[1,2,4]triazolo[4,3-c]pyrimidin-3(2H)-one by nucleophilic displacement of chloride with the requisite amine, followed by alkylation with iodomethane, in a manner analogous to that in which 1-(7,8-bis(4-chlorophenyl)-2-ethyl-3-oxo-2,3-dihydro-[1,2,4]triazolo[4,3-c]pyrimidin-5-yl)-3-(ethylamino)azetidine-3-carboxamide was prepared. HPLC retention time=4.718 min; HPLC/MS: $[M+H]^{30}$=544.

Example 24

Preparation of 7,8-bis(4-chlorophenyl)-2-methyl-5-((6-(trifluoromethyl)pyridin-3-yl)methylamino)-[1,2,4]triazolo[4,3-c]pyrimidin-3(2H)-one

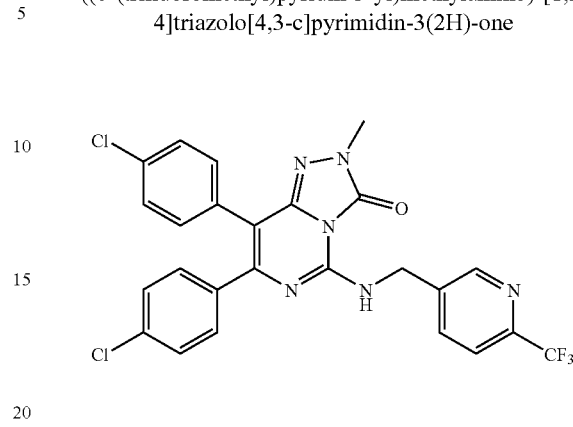

The title compound was prepared in two steps from 5-chloro-7,8-bis(4-chlorophenyl)-[1,2,4]triazolo[4,3-c]pyrimidin-3(2H)-one by nucleophilic displacement of chloride with the requisite amine, followed by alkylation with iodomethane, in a manner analogous to that in which 1-(7,8-bis(4-chlorophenyl)-2-ethyl-3-oxo-2,3-dihydro-[1,2,4]triazolo[4,3-c]pyrimidin-5-yl)-3-(ethylamino)azetidine-3-carboxamide was prepared. HPLC/MS: retention time=4.293 min, $[M+H]^{30}$=545.

Example 25

Preparation of 7,8-bis(4-chlorophenyl)-2-ethyl-5-((6-(trifluoromethyl)pyridin-3-yl)methylamino)-[1,2,4]triazolo[4,3-c]pyrimidin-3(2H)-one

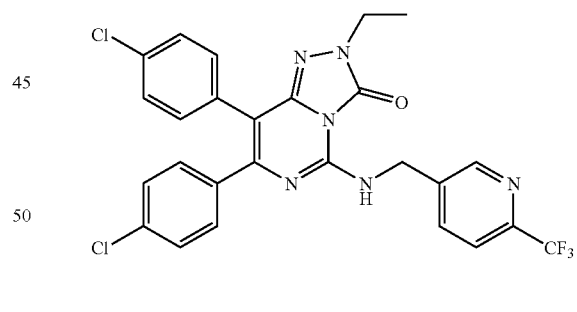

The title compound was prepared in two steps from 5-chloro-7,8-bis(4-chlorophenyl)-[1,2,4]triazolo[4,3-c]pyrimidin-3(2H)-one by nucleophilic displacement of chloride with the requisite amine, followed by alkylation with iodoethane, in a manner analogous to that in which 1-(7,8-bis(4-chlorophenyl)-2-ethyl-3-oxo-2,3-dihydro-[1,2,4]triazolo[4,3-c]pyrimidin-5-yl)-3-(ethylamino)azetidine-3-carboxamide was prepared. HPLC/MS: retention time=4.401 min, $[M+H]^{30}$=559.

Example 26

Preparation of 7,8-bis(4-chlorophenyl)-2-ethyl-5-(pyridin-2-ylmethylamino)-[1,2,4]triazolo[4,3-c]pyrimidin-3(2H)-one

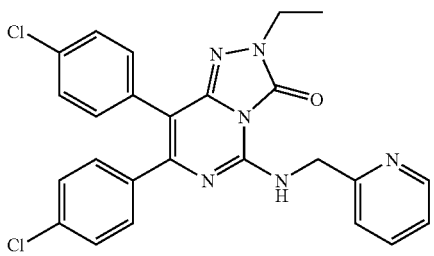

The title compound was prepared in two steps from 5-chloro-7,8-bis(4-chlorophenyl)-[1,2,4]triazolo[4,3-c]pyrimidin-3(2H)-one by nucleophilic displacement of chloride with the requisite amine, followed by alkylation with iodoethane, in a manner analogous to that in which 1-(7,8-bis(4-chlorophenyl)-2-ethyl-3-oxo-2,3-dihydro-[1,2,4]triazolo[4,3-c]pyrimidin-5-yl)-3-(ethylamino)azetidine-3-carboxamide was prepared. HPLC/MS: retention time=3.623 min, $[M+H]^{30}$ =491.

Example 27

Preparation of 7,8-bis(4-chlorophenyl)-2-ethyl-5-(pyridin-3-ylamino)-[1,2,4]triazolo[4,3-c]pyrimidin-3(2H)-one

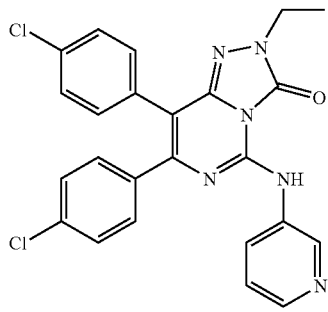

The title compound was prepared in two steps from 5-chloro-7,8-bis(4-chlorophenyl)-[1,2,4]triazolo[4,3-c]pyrimidin-3(2H)-one by nucleophilic displacement of chloride with the requisite amine, followed by alkylation with iodoethane, in a manner analogous to that in which 1-(7,8-bis(4-chlorophenyl)-2-ethyl-3-oxo-2,3-dihydro-[1,2,4]triazolo[4,3-c]pyrimidin-5-yl)-3-(ethylamino)azetidine-3-carboxamide was prepared. HPLC/MS: retention time=3.780 min, $[M+H]^{30}$ =477.

Example 28

Preparation of 7,8-bis(4-chlorophenyl)-5-((1-methylpiperidin-4-yl)methylamino)-2-(3,3,3-trifluoropropyl)-[1,2,4]triazolo[4,3-c]pyrimidin-3(2H)-one

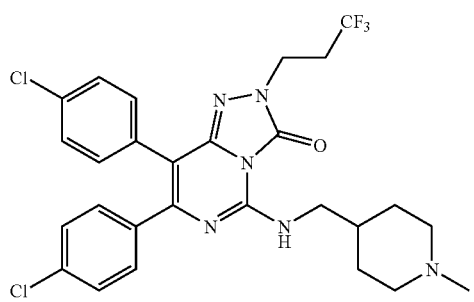

The title compound was prepared in two steps from 5-chloro-7,8-bis(4-chlorophenyl)-[1,2,4]triazolo[4,3-c]pyrimidin-3(2H)-one by nucleophilic displacement of chloride with the requisite amine, followed by alkylation with the 1-bromo-3-trifluoropropane, in a manner analogous to that in which 1-(7,8-bis(4-chlorophenyl)-2-ethyl-3-oxo-2,3-dihydro-[1,2,4]triazolo[4,3-c]pyrimidin-5-yl)-3-(ethylamino)azetidine-3-carboxamide was prepared. HPLC/MS: retention time=3.663 min, $[M+H]^{30}$ =579.

Example 29

Preparation of (S)-tert-butyl 3-((7,8-bis(4-chlorophenyl)-2-ethyl-3-oxo-2,3-dihydro-[1,2,4]triazolo[4,3-c]pyrimidin-5-ylamino)methyl)pyrrolidine-1-carboxylate

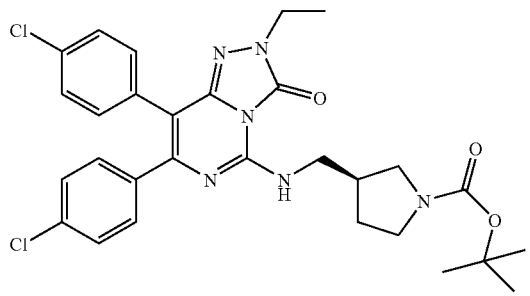

The title compound was prepared in two steps from 5-chloro-7,8-bis(4-chlorophenyl)-[1,2,4]triazolo[4,3-c]pyrimidin-3(2H)-one by nucleophilic displacement of chloride with the requisite amine, followed by alkylation with iodoethane, in a manner analogous to that in which 1-(7,8-bis(4-chlorophenyl)-2-ethyl-3-oxo-2,3-dihydro-[1,2,4]triazolo[4,3-c]pyrimidin-5-yl)-3-(ethylamino)azetidine-3-carboxamide was prepared. HPLC/MS: retention time=4.655 min, $[M+H]^{30}$ =583.

Example 30

Preparation of (S)-tert-butyl 3-((7,8-bis(4-chlorophenyl)-2-methyl-3-oxo-2,3-dihydro-[1,2,4]triazolo[4,3-c]pyrimidin-5-ylamino)methyl)pyrrolidine-1-carboxylate

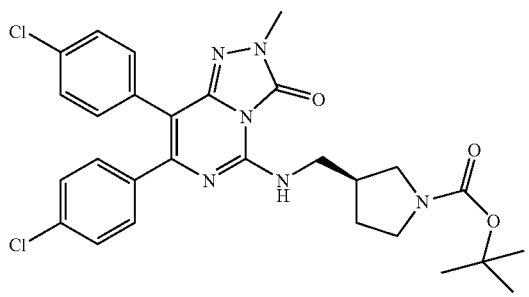

The title compound was prepared in two steps from 5-chloro-7,8-bis(4-chlorophenyl)-[1,2,4]triazolo[4,3-c]pyrimidin-3(2H)-one by nucleophilic displacement of chloride with the requisite amine, followed by alkylation with iodomethane, in a manner analogous to that in which 1-(7,8-bis(4-chlorophenyl)-2-ethyl-3-oxo-2,3-dihydro-[1,2,4]triazolo[4,3-c]pyrimidin-5-yl)-3-(ethylamino)azetidine-3-carboxamide was prepared. HPLC/MS: retention time=4.60 min, $[M+H]^{30}$=569.

Example 31

Preparation of (R)-7,8-bis(4-chlorophenyl)-2-methyl-5-(pyrrolidin-3-ylmethylamino)-[1,2,4]triazolo[4,3-c]pyrimidin-3(2H)-one

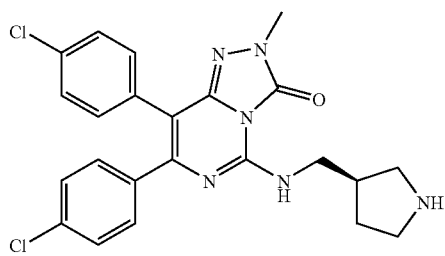

A solution of (S)-tert-butyl 3-((7,8-bis(4-chlorophenyl)-2-methyl-3-oxo-2,3-dihydro-[1,2,4]triazolo[4,3-c]pyrimidin-5-ylamino)methyl)pyrrolidine-1-carboxylate (85 mg, 0.15 mmol) in a mixture of TFA (0.1 mL) and CH$_2$Cl$_2$ (0.5 mL) was stirred at room temperature until HPLC/MS indicated complete conversion to the title compound. The reaction mixture was then partitioned between EtOAc and saturated aqueous sodium bicarbonate solution. The organic phase was separated, dried, and evaporated. The residue was purified by preparative reverse phase HPLC (without TFA) to obtain the title compound as a pale yellow solid. HPLC/MS: retention time 3.475 min, $[M+H]^{30}$=469.

Example 32

Preparation of ethyl 1-(7,8-bis(4-chlorophenyl)-2-ethyl-3-oxo-2,3-dihydro-[1,2,4]triazolo[4,3-c]pyrimidin-5-yl)azetidine-3-carboxylate

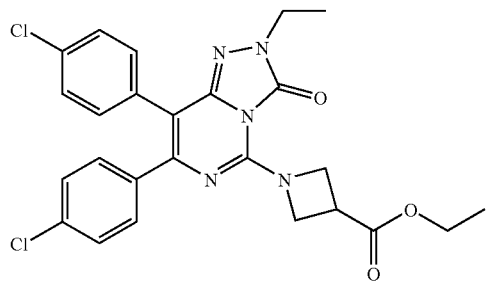

The title compound was prepared in two steps from 5-chloro-7,8-bis(4-chlorophenyl)-[1,2,4]triazolo[4,3-c]pyrimidin-3 (2H)-one by nucleophilic displacement of chloride with the requisite amine, followed by alkylation with iodoethane, in a manner analogous to that in which 1-(7,8-bis(4-chlorophenyl)-2-ethyl-3-oxo-2,3-dihydro-[1,2,4]triazolo[4,3-c]pyrimidin-5-yl)-3-(ethylamino)azetidine-3-carboxamide was prepared. HPLC/MS: retention time=4.440 min, $[M+H]^{30}$=512.

Example 33

Preparation of 5-(azetidin-1-yl)-7,8-bis(4-chlorophenyl)-2-ethyl-[1,2,4]triazolo[4,3-c]pyrimidin-3(2H)-one

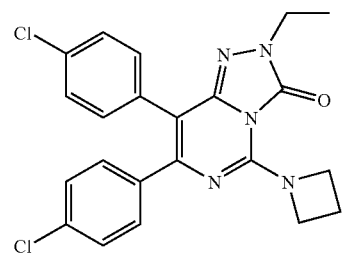

The title compound was prepared in two steps from 5-chloro-7,8-bis(4-chlorophenyl)-[1,2,4]triazolo[4,3-c]pyrimidin-3 (2H)-one by nucleophilic displacement of chloride with the requisite amine, followed by alkylation with iodoethane, in a manner analogous to that in which 1-(7,8-bis(4-chlorophenyl)-2-ethyl-3-oxo-2,3-dihydro-[1,2,4]triazolo[4,3-c]pyrimidin-5-yl)-3-(ethylamino)azetidine-3-carboxamide was prepared. HPLC/MS: retention time=4.423 min, $[M+H]^{30}$=440.

Example 34

Preparation of 5-(azetidin-1-yl)-7,8-bis(4-chlorophenyl)-2-((6-(trifluoromethyl)pyridin-3-yl)methyl)-[1,2,4]triazolo[4,3-c]pyrimidin-3(2H)-one

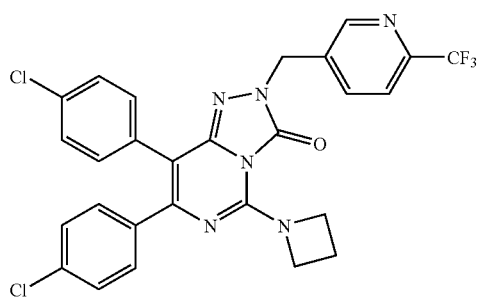

The title compound was prepared in two steps from 5-chloro-7,8-bis(4-chlorophenyl)-[1,2,4]triazolo[4,3-c]pyrimidin-3(2H)-one by nucleophilic displacement of chloride with the requisite amine, followed by alkylation with 5-(chloromethyl)-2-(trifluoromethyl)pyridine, in a manner analogous to that in which 1-(7,8-bis(4-chlorophenyl)-2-ethyl-3-oxo-2,3-dihydro-[1,2,4]triazolo[4,3-c]pyrimidin-5-yl)-3-(ethylamino)azetidine-3-carboxamide was prepared. HPLC/MS: retention time=4.483 min, $[M+H]^{30}$ =571.

Example 35

Preparation of 5-(azetidin-1-yl)-7,8-bis(4-chlorophenyl)-2-(3,3,3-trifluoropropyl)-[1,2,4]triazolo[4,3-c]pyrimidin-3(2H)-one

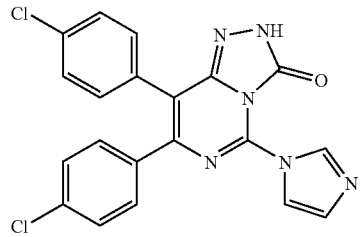

The title compound was prepared in two steps from 5-chloro-7,8-bis(4-chlorophenyl)-[1,2,4]triazolo[4,3-c]pyrimidin-3(2H)-one by nucleophilic displacement of chloride with the requisite amine, followed by alkylation with 1-bromo-3-trifluoropropane, in a manner analogous to that in which 1-(7,8-bis(4-chlorophenyl)-2-ethyl-3-oxo-2,3-dihydro-[1,2,4]triazolo[4,3-c]pyrimidin-5-yl)-3-(ethylamino)azetidine-3-carboxamide was prepared. HPLC/MS: retention time=4.481 min, $[M+H]^{30}$ =508.

Example 36

Preparation of 7,8-bis(4-chlorophenyl)-2-ethyl-5-(3-hydroxyazetidin-1-yl)-[1,2,4]triazolo[4,3-c]pyrimidin-3(2H)-one

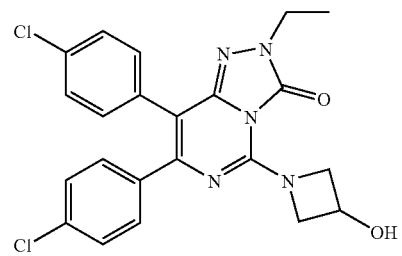

The title compound was prepared in two steps from 5-chloro-7,8-bis(4-chlorophenyl)-[1,2,4]triazolo[4,3-c]pyrimidin-3(2H)-one by nucleophilic displacement of chloride with the requisite amine, followed by alkylation with iodoethane, in a manner analogous to that in which 1-(7,8-bis(4-chlorophenyl)-2-ethyl-3-oxo-2,3-dihydro-[1,2,4]triazolo[4,3-c]pyrimidin-5-yl)-3-(ethylamino)azetidine-3-carboxamide was prepared. HPLC/MS: retention time=4.173 min, $[M+H]^{30}$ =456.

Example 37

Preparation of 7,8-bis(4-chlorophenyl)-5-methyl-2-(4-(trifluoromethyl)benzyl)-[1,2,4]triazolo[4,3-c]pyrimidin-3(2H)-one

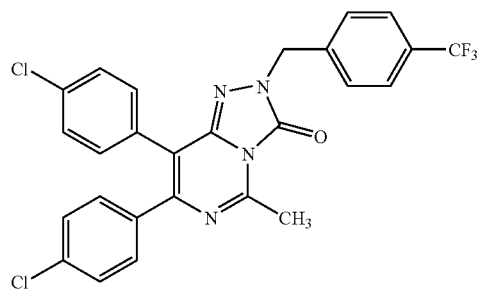

A. Preparation of 7,8-bis(4-chlorophenyl)-5-methyl-[1,2,4]triazolo[4,3-c]pyrimidin-3(2H)-one

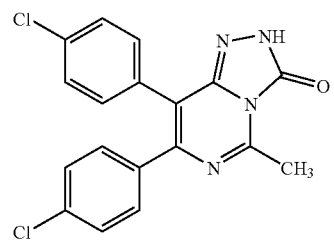

To a stirred solution of 5-chloro-7,8-bis(4-chlorophenyl)-[1,2,4]triazolo[4,3-c]pyrimidin-3(2H)-one (50 mg, 0.128 mmol) and tetrakis(triphenylphosphine)palladium (7 mg, 0.006 mmol) in THF (0.5 mL) at room temperature under argon was added 2.0 M methylzinc chloride solution in THF (0.25 mL, 0.5 mmol). The reaction mixture was stirred at reflux for 1.5 h. The reaction mixture was cooled in an ice bath and quenched with saturated aqueous NH$_4$Cl. EtOAc (5 mL) and water (5 mL) were added and the layers were separated. The organic layer was dried (MgSO$_4$), filtered, and concentrated under reduced pressure. The crude product was purified by silica gel column chromatography eluted with 40% EtOAc-hexanes to obtain 40 mg of the title compound as a white solid. HPLC/MS: retention time=3.883 min, [M+H]$^{30}$ =371.

B. Preparation of 7,8-bis(4-chlorophenyl)-5-methyl-2-(4-(trifluoromethyl)benzyl)-[1,2,4]triazolo[4,3-c]pyrimidin-3(2H)-one

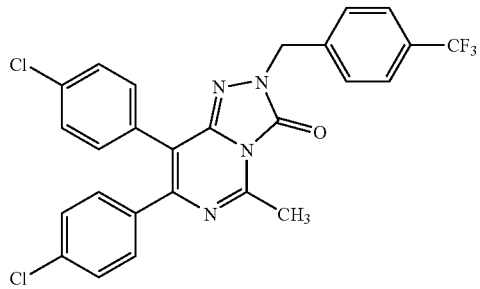

The title compound was prepared by coupling 7,8-bis(4-chlorophenyl)-5-methyl-[1,2,4]triazolo[4,3-c]pyrimidin-3(2H)-one with 4-trifluoromethylbenzyl bromide in a manner analogous to that in which 1-(7,8-bis(4-chlorophenyl)-3-oxo-2-(4-(trifluoromethyl)benzyl)-2,3-dihydro-[1,2,4]triazolo[4,3-c]pyrimidin-5-yl)-3-(ethylamino)azetidine-3-carboxamide was prepared. HPLC/MS: retention time=4.485 min, [M+H]$^{30}$ =529.

Example 38

Preparation of 7,8-bis(4-chlorophenyl)-5-methyl-2-((6-(trifluoromethyl)pyridin-3-yl)methyl)-[1,2,4]triazolo[4,3-c]pyrimidin-3(2H)-one

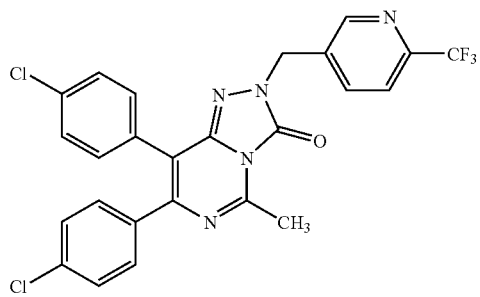

The title compound was prepared by coupling 7,8-bis(4-chlorophenyl)-5-methyl-[1,2,4]triazolo[4,3-c]pyrimidin-3(2H)-one with 5-(chloromethyl)-2-(trifluoromethyl)pyridine in a manner analogous to that in which 7,8-bis(4-chlorophenyl)-5-methyl-2-(4-(trifluoromethyl)benzyl)-[1,2,4]triazolo[4,3-c]pyrimidin-3(2H)-one was prepared. HPLC/MS: retention time=4.188 min, [M+H]$^{30}$ =530.

Example 39

Preparation of 7,8-bis(4-chlorophenyl)-2-ethyl-5-(4-methoxybenzyl)-[1,2,4]triazolo[4,3-c]pyrimidin-3(2H)-one

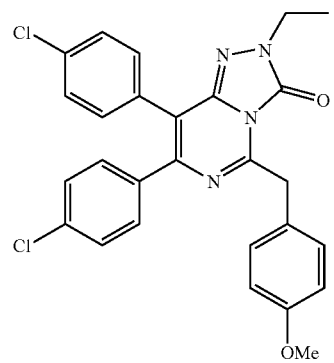

The title compound was prepared in two steps from 5-chloro-7,8-bis(4-chlorophenyl)-[1,2,4]triazolo[4,3-c]pyrimidin-3(2H)-one by nucleophilic displacement of chloride with 4-methoxybenzylzinc chloride, followed by alkylation with iodoethane, in a manner analogous to that in which 7,8-bis(4-chlorophenyl)-5-methyl-2-(4-(trifluoromethyl)benzyl)-[1,2,4]triazolo[4,3-c]pyrimidin-3(2H)-one was prepared. HPLC/MS: retention time=4.571 min, [M+H]$^{30}$ =505.

Example 40

Preparation of 7,8-bis(4-chlorophenyl)-2-((6-(trifluoromethyl)pyridin-3-yl)methyl)-[1,2,4]triazolo[4,3-c]pyrimidine-3,5(2H,6H)-dione

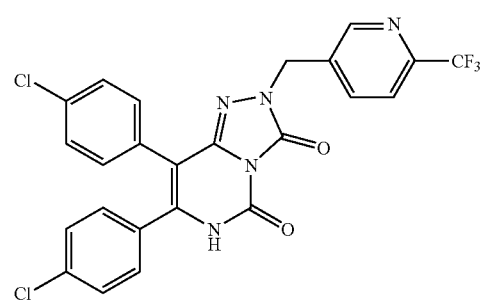

A. Preparation of 7,8-bis(4-chlorophenyl)-5-(1H-imidazol-1-yl)-[1,2,4]triazolo[4,3-c]pyrimidin-3(2H)-one

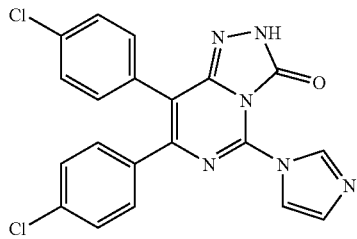

To a stirred solution of 1,1'-carbonyldiimidazole (80 mg, 0.49 mmol) in THF (1 mL) at room temperature under argon was added 2-chloro-4,5-bis(4-chlorophenyl)-6-hydrazinylpyrimidine (60 mg, 0.16 mmol). The reaction mixture was stirred at room temperature for 10 min. The reaction mixture was diluted with EtOAc (5 mL) and water (5 mL). The layers were separated. The organic layer was dried (MgSO$_4$), filtered, and concentrated at reduced pressure to obtain 60 mg of the title compound as a yellow solid. HPLC/MS: retention time=3.218 min, [M+H]$^{30}$ =423.

B. Preparation of 7,8-bis(4-chlorophenyl)-2-((6-(trifluoromethyl)pyridin-3-yl)methyl)-[1,2,4]triazolo[4,3-c]pyrimidine-3,5(2H,6H)-dione

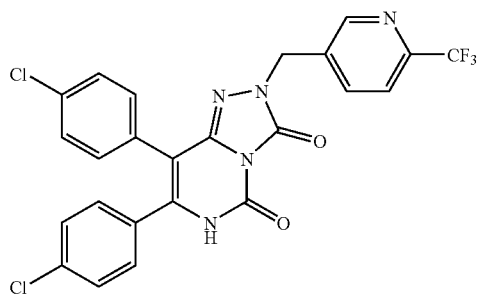

To a solution of 7,8-bis(4-chlorophenyl)-5-(1H-imidazol-1-yl)-[1,2,4]triazolo[4,3-c]pyrimidin-3(2H)-one (60 mg, 0.14 mmol) in DMF (0.5 mL) at room temperature under argon was added K$_2$CO$_3$ (25 mg, 0.18 mmol), followed by 5-(chloromethyl)-2-(trifluoromethyl)pyridine (28 mg, 0.14 mmol). The reaction mixture was stirred at 50° C. in a pre-heated oil bath for 30 min. After the reaction mixture was cooled to room temperature, water (5 mL) and EtOAc (5 mL) were added. The layers were separated. The organic layer was dried (MgSO$_4$), filtered, and concentrated under reduced pressure. The crude product thus obtained was purified by preparative reverse phase HPLC (without TFA) to obtain 22.5 mg of the title compound as a white solid. HPLC/MS: retention time=3.871 min, [M+H]$^{30}$ =532.

Example 41

Preparation of 5-amino-7,8-bis(4-chlorophenyl)-2-((6-(trifluoromethyl)pyridin-3-yl)methyl)-[1,2,4]triazolo[4,3-c]pyrimidin-3(2H)-one

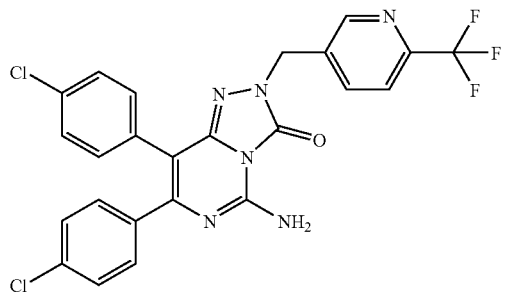

A. Preparation of 5-amino-7,8-bis(4-chlorophenyl)-[1,2,4]triazolo[4,3-c]pyrimidin-3(2H)-one

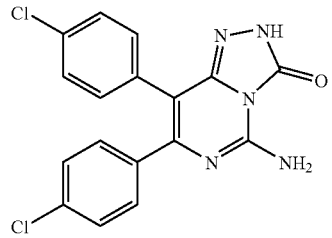

To a stirring solution of 5-chloro-7,8-bis(4-chlorophenyl)-[1,2,4]triazolo[4,3-c]pyrimidin-3(2H)-one (120 mg, 0.31 mmol) in 3 mL THF, was added ammonium hydroxide (28% in water, 0.12 mL, 1.8 mmol). The reaction mixture was stirred at room temperature for 3 h and then concentrated under reduced pressure. The resulting crude title compound was used in the next step without further purification. HPLC/MS: retention time=3.60 min, [M+H]$^{30}$ =372.

B. Preparation of 5-amino-7,8-bis(4-chlorophenyl)-2-((6-(trifluoromethyl)pyridin-3-yl)methyl)[1,2,4]triazolo[4,3-c]pyrimidin-3(2H)-one

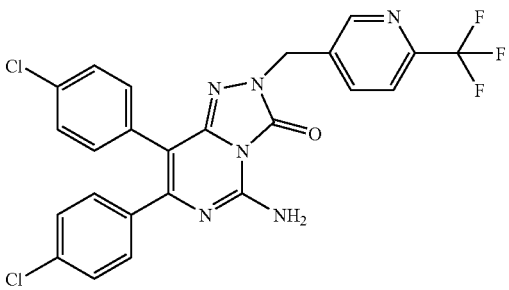

To a mixture of crude 5-amino-7,8-bis(4-chlorophenyl)-[1,2,4]triazolo[4,3-c]pyrimidin-3(2H)-one (26 mg, 0.07 mmol), DMF (0.5 mL), and potassium carbonate (45 mg, 0.32 mmol) was added 5-chloromethyl-2-(trifluoromethyl)pyridine (21.2 mg, 0.11 mmol). The resulting reaction mixture was stirred at 50° C. for 80 min. The reaction mixture was purified by preparative reverse phase HPLC without prior workup to obtain 25 mg of the title compound as a light yellow solid. HPLC/MS: retention time=4.14 min, [M+H]$^{30}$ =531.

Example 42

Preparation of 5-(methylamino)-7,8-bis(4-chlorophenyl)-2-((6-(trifluoromethyl)pyridin-3-yl)methyl)-[1,2,4]triazolo[4,3-c]pyrimidin-3(21)-one

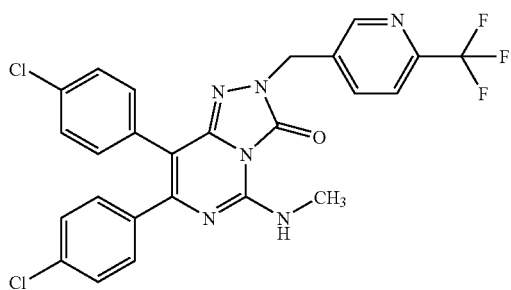

A. Preparation of 5-(methylamino)-7,8-bis(4-chlorophenyl)-[1,2,4]triazolo[4,3-c]pyrimidin-3(2H)-one

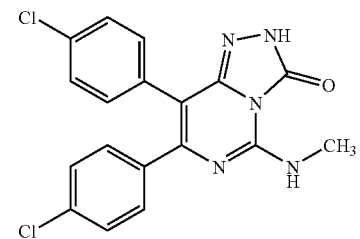

To a stirring solution of 5-chloro-7,8-bis(4-chlorophenyl)-[1,2,4]triazolo[4,3-c]pyrimidin-3(2H)-one (36 mg, 0.09 mmol) in 1 mL THF was added methylamine (2 M in THF, 0.13 mL, 0.26 mmol), followed by N,N-diisopropylethylamine (12 mg, 0.09 mmol). The reaction mixture was stirred at room temperature for 5 h and then concentrated under reduced pressure. The resulting crude title compound was used in the next step without further purification. HPLC/MS: retention time=4.06 min, [M+H]$^{30}$ =386.

B. Preparation of 5-(methylamino)-7,8-bis(4-chlorophenyl)-2-((6-(trifluoromethyl)pyridin-3-yl)methyl)-[1,2,4]triazolo[4,3-c]pyrimidin-3(2H)-one

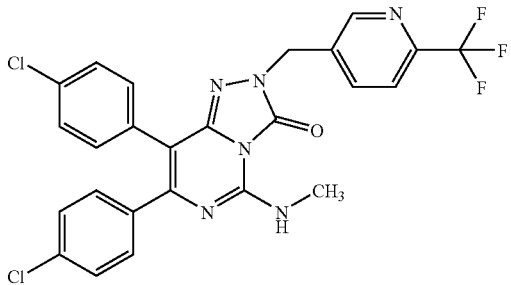

To a mixture of crude 5-(methylamino)-7,8-bis(4-chlorophenyl)-[1,2,4]triazolo[4,3-c]pyrimidin-3(2H)-one, DMF (0.5 mL), and potassium carbonate (38 mg, 0.28 mmol) was added 5-chloromethyl-2-(trifluoromethyl)pyridine (18 mg, 0.09 mmol). The resulting reaction mixture was stirred at 70° C. for 1 h. The reaction mixture was then diluted with EtOAc, washed with water and saturated aqueous NaCl, dried (Na$_2$SO$_4$), and concentrated at reduced pressure. The residue was purified by preparative reverse phase HPLC to obtain 25 mg (51% over two steps) of the title compound as a light yellow solid. HPLC/MS: retention time=4.40 min, [M+H]$^{30}$ =545.

Example 43

Preparation of 7,8-bis(4-chlorophenyl)-5-(isopropylamino)-2-methyl-[1,2,4]triazolo[4,3-c]pyrimidin-3(2H)-one

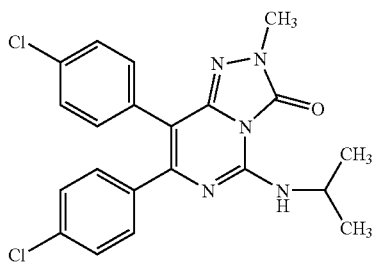

A. Preparation of 7,8-bis(4-chlorophenyl)-5-(isopropylamino)-[1,2,4]triazolo[4,3-c]pyrimidin-3(2H)-one

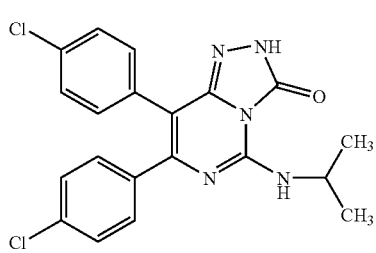

To a stirring solution of 5-chloro-7,8-bis(4-chlorophenyl)-[1,2,4]triazolo[4,3-c]pyrimidin-3(2H)-one (39 mg, 0.10 mmol) in 1 mL THF, was added isopropylamine (18 mg, 0.30 mmol). The reaction mixture was stirred at room temperature for 1 h and then concentrated under reduced pressure. The resulting crude title compound was used in the next step without further purification.

B. Preparation of 7,8-bis(4-chlorophenyl)-5-(isopropylamino)-2-methyl-[1,2,4]triazolo[4,3-c]pyrimidin-3(2H)-one

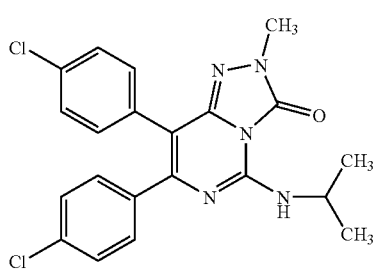

To a mixture of crude 7,8-bis(4-chlorophenyl)-5-(isopropylamino)-[1,2,4]triazolo[4,3-c]pyrimidin-3(2H)-one, DMF (0.7 mL), and potassium carbonate (21 mg, 0.15 mmol) was added methyl iodide (213 mg, 1.5 mmol). The resulting reaction mixture was stirred at room temperature for 3 h. The reaction mixture was then diluted with EtOAc, washed with water and saturated aqueous NaCl, dried ($Na_2SO_4$), and concentrated at reduced pressure. The residue was purified by preparative reverse phase HPLC to obtain 14 mg (65% over two steps) of the title compound as a light yellow solid. HPLC/MS: retention time=4.54 min, [M+H]$^{30}$ =428.

The following are preparations of additional intermediates useful in the synthesis of the compounds of Formulas I and II.

Preparation of Intermediate 4-chloro-6-(4-chlorophenyl)-5-(pyridin-4-yl)pyrimidine

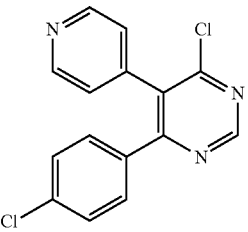

A. Preparation of 4,6-dimethoxypyrimidine

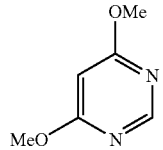

To a suspension of 4,6-dichloropyrimidine (6.5 g, 43.9 mmol) in methanol (30 mL) at room temperature under argon was added NaOMe (7.1 g, 132 mmol) over 5 min. The resulting suspension was heated at 65° C. under argon for 24 h. Analysis by HPLC/MS indicated that the reaction was complete. Most of the solvent was removed under reduced pressure, then 1 M aqueous HCl (50 mL) and $CH_2Cl_2$ (50 mL) were added to the residue. The layers were separated and the organic phase was washed with saturated aqueous NaCl (30 mL), then dried ($Na_2SO_4$), filtered and evaporated. The crude product was purified by silica gel column chromatography eluted with ethyl acetate-hexanes to obtain the title compound (5.76 g) as a low melting solid. See also Synthesis 1998, page 36.

B. Preparation of 5-bromo-4,6-dimethoxypyrimidine

To the solution of 4,6-dimethoxypyrimidine (5 g, 35.7 mmol) in HOAc (20 mL) at room temperature under argon was added $Ac_2O$ (4.6 g, 44.6 mmol). The resulting solution was heated at 100° C. for 10 min and then NBS (7.9 g, 44.6 mmol) was added. Heating was continued at 100° C. for 5 h. Analysis by HPLC/MS indicated that the reaction was complete. After the reaction mixture was cooled to room temperature, water (50 mL) was added. The resulting precipitate was collected by filtration and further washed with water (15 mL×3), then dried under vacuum. The title compound (7.5 g) was obtained as a white solid. ¹H NMR (CDCl₃): δ 4.05 (s, 6H), 8.32 (s, 1H). ¹³C NMR (CDCl₃): δ 55.2, 89.0, 154.9, 166.8.

C. Preparation of 4,6-dimethoxy-5-(pyridin-4-yl)pyrimidine

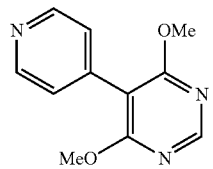

A mixture of 5-bromo-4,6-dimethoxypyrimidine (2.18 g, 10 mmol), pyridine-4-boronic acid (1.85 g, 15 mmol), K₂CO₃ (2.76 g, 20 mmol), and PXPd (539 mg, 1.0 mmol) in ethanol/THF (1:1, 25 mL) under argon was heated at 70° C. for 3 h. Analysis by HPLC/MS indicated that the reaction was complete. After the reaction mixture was cooled to room temperature, the solvent mixture was removed under reduced pressure. The residue was dissolved in EtOAc (30 mL) and washed with saturated aqueous NaCl (20 mL), then dried over Na₂SO₄, filtered and evaporated under reduced pressure. The crude product was purified by silica gel column chromatography eluted with ethyl acetate-hexanes to obtain the title compound (1.79 g) as a white solid. ¹H NMR (CDCl₃): δ 3.97 (s, 6H), 7.36 (d, 2H), 8.47 (s, 1H), 8.64 (d, 2H).

D. Preparation of 4,6-dichloro-5-(pyridin-4-yl)pyrimidine

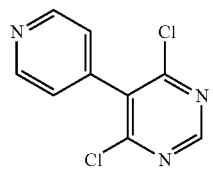

To a stirred solution of 4,6-dimethoxy-5-(pyridin-4-yl)pyrimidine (1.79 g, 8.25 mmol) in CH₂Cl₂ (5 mL) at 0° C. under argon was added BBr₃ (1 M solution in CH₂Cl₂, 25 mL, 25 mmol) over 5 min. The reaction mixture was allowed to warm to room temperature gradually while stirring was continued for 28 h. Analysis by HPLC/MS indicated that the reaction was complete. The solvent was evaporated and the residue was coevaporated with toluene (2×5 mL), then dried under vacuum. To this, POCl₃ (20 mL) was added. The resulting suspension was heated at 100° C. under argon for 20 h. Analysis by HPLC/MS indicated that the reaction was complete. The solvent was largely removed under reduced pressure, and ice (50 g) was added to the residue. The resulting mixture was stirred for 1 h. The product was collected by filtration and washed with water (10 mL×3), then dried under vacuum. The crude product was purified by silica gel column chromatography eluted with ethyl acetate-hexanes to obtain the title compound (1.07 g) as a white solid. ¹H NMR (CDCl₃): δ 7.28 (d, 2H), 8.81 (d, 2H), 8.85 (s, 1H).

E. Preparation of 4-chloro-6-(4-chlorophenyl)-5-(pyridin-4-yl)pyrimidine

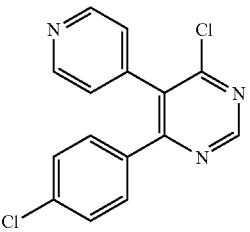

To a mixture of 4,6-dichloro-5-(pyridin-4-yl)pyrimidine (1.07 g, 4.8 mmol), 4-chlorophenylboronic acid (740 mg, 4.8 mmol) and tetrakis(triphenylphosphine)palladium (550 mg, 0.48 mmol) in toluene (10 mL) at room temperature under argon was added aqueous Na₂CO₃ solution (2 M, 5 mL, 10 mmol). The resulting mixture was stirred at 100° C. under argon for 15 h. Analysis by HPLC/MS indicated that the reaction was complete. After the reaction mixture was cooled to room temperature, water (25 mL) was added. The resulting mixture was extracted with EtOAc (2×25 mL). The combined organic layers were dried over Na₂SO₄, filtered and concentrated under reduced pressure. The residue was purified by silica gel column chromatography eluted with ethyl acetate-hexanes to obtain the title compound (1.12 g, HPLC purity about 92%) as a white solid. ¹H NMR (CDCl₃): δ7.18 (d, 2H), 7.2-7.3 (m, 4H), 8.66 (d, 2H), 9.07 (s, 1H).

The following are preparations of reagents R³-LG and R³—OH useful in the synthesis of the working Examples above, the contemplated Examples below, and/or other compounds of Formulas I and II.

Preparation of Reagent 3-(chloromethyl)-2-methyl-6-(trifluoromethyl)pyridine

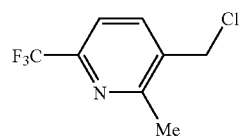

A. Preparation of (Z)-4-amino-1,1,1-trifluorobut-3-en-2-one

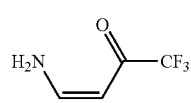

M. Hojo, et al., Tetrahedron Lett., volume 30, pp. 6173-6176, 1989 and M. Buback, et al., Chem. Ber., volume 122, pp. 1179-1186, 1989 provide procedures for this exact transformation. To a solution of 4-ethoxy-1,1,1-trifluorobut-3-en-2-one (technical grade, 50 g, 0.3 mol) in 300 mL of acetonitrile stirring at room temperature under argon was added concentrated aqueous ammonium hydroxide solution (28% ammonia in water, 21.6 g, 0.36 mol) over 2 min. The resulting mixture was stirred at room temperature under argon for 14 h. Solvent was removed under reduced pressure to afford 40.1 g of compound the title compound as a yellow oil at about 85-90% purity according to $^1$H NMR. This (Z)-4-amino-1,1,1-trifluorobut-3-en-2-one was used in the next step as is, although it is possible to purify it by distillation (see reference).

B. Preparation of methyl 2-methyl-6-(trifluoromethyl)nicotinate

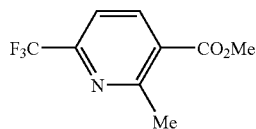

E. Okada, et al., Heterocycles, volume 46, pp. 129-132, 1997 provides a procedure for this exact transformation. A solution of crude (Z)-4-amino-1,1,1-trifluorobut-3-en-2-one (20.7 g, 85-90% purity, about 18.2 g net, 0.13 mol), methyl acetoacetate (20.9 g, 0.18 mol), and TFA (20.6 g, 0.18 mol) in 150 mL toluene under argon was heated at 80° C. for 16 h. HPLC/MS analysis indicated that the reaction was complete. Solvent was evaporated under vacuum. The resulting residue was dissolved in 200 mL EtOAc and washed with 10% aqueous sodium carbonate solution (100 mL), then saturated aqueous NaCl (100 mL). The organic phase was dried over anhydrous sodium sulfate and filtered. The filtrate was concentrated under vacuum to obtain 33.7 g of brown oil, which was purified by silica gel column chromatography eluting with (hexanes-EtOAc, 3:1) to provide the title compound (23.3 g, 82% yield) as light yellow oil. HPLC/MS: retention time=2.9 min, [M+H]$^{30}$=220.

C. Preparation of (2-methyl-6-(trifluoromethyl)pyridin-3-yl)methanol

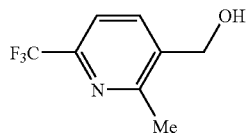

To the solution of methyl 2-methyl-6-(trifluoromethyl)nicotinate (8.8 g, 40 mmol) in 40 mL dry THF at 0° C. under argon was added 1.0 M lithium aluminum hydride in THF solution (40 mL, 40 mmol) drop-wise over 15 min. The reaction mixture was allowed to warm to room temperature over 1 h. HPLC/MS analysis indicated that the reaction was complete. Rochelle's salt, 10% aqueous solution (20 mL) was carefully added to the stirring reaction mixture over a period of 10 min. After 1 h of subsequent stirring, 50 mL EtOAc and water were added. The layers were separated. The organic phase was dried over anhydrous sodium sulfate and filtered. The filtrate was concentrated to obtain 7.5 g of the title compound as a colorless oil, which was greater than 98% pure. HPLC/MS: retention time=2.1 min, [M+H]$^{30}$=192.

D. Preparation of 3-(chloromethyl)-2-methyl-6-(trifluoromethyl)pyridine

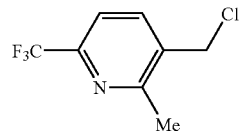

To a solution of (2-methyl-6-(trifluoromethyl)pyridin-3-yl)methanol (14.5 g, 71 mmol) in 100 mL CH$_2$Cl$_2$ at room temperature under argon was added SOCl$_2$ (16.8 g, 142 mmol), followed by about 1.5 mL DMF, which was added to re-dissolve the rapidly formed, precipitating hydrochloride salt of the starting material. The resulting reaction mixture was stirred for 16 h. HPLC/MS analysis indicated that the reaction was complete. Solvent was evaporated under vacuum. The resulting residue was dissolved in 200 mL Et$_2$O, and the resulting solution was washed with 10% aqueous sodium carbonate solution (100 mL), then saturated aqueous NaCl (100 mL). The organic phase was dried over anhydrous sodium sulfate and filtered. The filtrate was concentrated under vacuum to obtain 13.7 g of the title compound as a tan oil, which was greater than 98% pure. HPLC/MS: retention time=2.9 min, [M+H]$^{30}$=210.

Preparation of Reagent 3-(bromomethyl)-2-methyl-6-(trifluoromethyl)pyridine

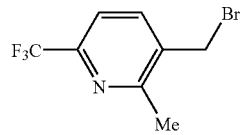

A mixture of (2-methyl-6-(trifluoromethyl)pyridin-3-yl)methanol (1.677 g, 8.77 mmol, 76% pure) in 48% aq. HBr (10 mL) was heated to reflux (oil bath temperature, 135° C.) for 24 h. The volatile components of the resulting biphasic mixture were distilled under vacuum to remove most of the hydrogen bromide (sodium hydroxide trap). The residue was partitioned between 2:1 EtOAc/THF and water (at pH 3) and the organic phase was dried (MgSO$_4$), filtered and evaporated. The solid residue was re-evaporated after addition of dichloromethane/hexanes to obtain the title compound as a tan solid, 1.19 g, 71% yield (based on the purity of the starting material). HPLC/MS: retention time=2.15 min, [M+H]$^{30}$=254.

Preparation of Reagent 3-(chloromethyl)-2-ethyl-6-(trifluoromethyl)pyridine

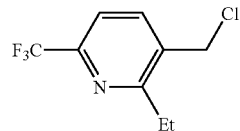

The title compound was prepared from (Z)-4-amino-1,1,1-trifluorobut-3-en-2-one and methyl 3-oxopentanoate analogously to the way 3-(chloromethyl)-2-methyl-6-(trifluoromethyl)pyridine was prepared from (Z)-4-amino-1,1,1-trifluorobut-3-en-2-one and methyl acetoacetate in three steps: 1. TFA-mediated cyclocondensation to methyl 2-ethyl-6-(trifluoromethyl)nicotinate (HPLC/MS: retention time=3.2 min, [M+H]$^{30}$ =234); 2. reduction with lithium aluminum hydride to (2-ethyl-6-(trifluoromethyl)pyridin-3-yl)methanol (HPLC/MS: retention time=2.4 min, [M+H]$^{+}$=206); and 3. reaction with SOCl$_2$ to afford the title compound (HPLC/MS: retention time=3.3 min, [M+H]$^{30}$ =224).

Preparation of Reagent 3-(chloromethyl)-2-cyclopropyl-6-(trifluoromethyl)pyridine

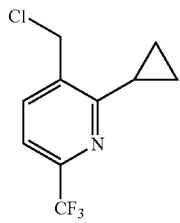

A. Preparation of methyl 2-cyclopropyl-6-(trifluoromethyl)nicotinate

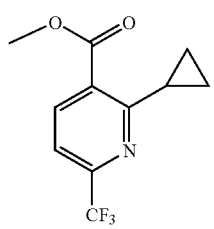

To a stirring solution of (Z)-4-amino-1,1,1-trifluorobut-3-en-2-one (3 g, 21.58 mmol) and methyl 3-cyclopropyl-3-oxopropanoate (3.7 g, 26.03 mmol) in toluene (20 mL) at room temperature under argon was added TFA (2.96 g, 25.92 mmol). The reaction mixture was stirred at reflux for 10 h. The reaction mixture was then cooled to room temperature and concentrated under vacuum to obtain a gum. EtOAc (50 mL) and 15% aqueous sodium carbonate solution (50 mL) were added, and the resulting mixture was stirred at room temperature for 10 min. The organic layer was separated, washed with saturated aqueous NaCl, dried (MgSO$_4$), filtered and concentrated to obtain crude product as a yellow oil. This crude product was purified by automated silica gel chromatography (eluted with ethyl acetate-hexanes) to isolate 1 g of the title compound as a pale yellow oil. HPLC/MS: retention time=3.618 min, [M+H]$^{+}$=246.

B. Preparation of (2-cyclopropyl-6-(trifluoromethyl)pyridin-3-yl)methanol

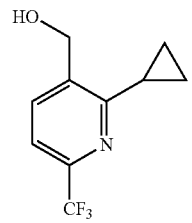

To a solution of methyl 2-cyclopropyl-6-(trifluoromethyl)nicotinate (1 g, 4.08 mmol) in THF (6 mL) at 0° C. under argon was added 1.0 M lithium aluminum hydride in THF solution (6 mL, 6.0 mmol). The reaction mixture was stirred at 0° C. for 15 min. EtOAc (20 mL) was added to the reaction mixture, which was then stirred at room temperature for 30 min. A 10% aqueous potassium sodium tartrate solution (20 mL) was added to the reaction mixture and stirring was continued for another 30 min. The organic layer was separated, washed with saturated aqueous NaCl, dried (MgSO$_4$), filtered and concentrated to obtain 890 mg of the title compound as a pale yellow oil. HPLC/MS: retention time=3.055 min, [M+H]$^{+}$=218.

C. Preparation of 3-(chloromethyl)-2-cyclopropyl-6-(trifluoromethyl)pyridine

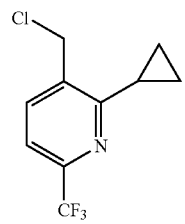

To a stirring solution of (2-cyclopropyl-6-(trifluoromethyl)pyridin-3-yl)methanol (890 mg, 4.1 mmol) in dichloromethane (10 mL) at room temperature under argon was added thionyl chloride (730 mg, 6.1 mmol) followed by 3 drops of DMF. The reaction mixture was stirred at room temperature for 15 h. The reaction mixture was then concentrated under vacuum to obtain a light brown oil. This oil was diluted with EtOAc (20 mL) and washed with 10% aqueous Na$_2$CO$_3$ solution (20 mL). The organic layer was separated, washed with saturated aqueous NaCl, dried (MgSO$_4$), filtered and concentrated to obtain 900 mg of the title compound as a light brown oil. HPLC/MS: retention time=3.66 min, [M+H]$^{+}$=236.

Preparation of Reagent 3-(chloromethyl)-2-methoxy-6-(trifluoromethyl)pyridine

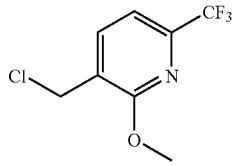

A. Preparation of methyl 2-methoxy-6-(trifluoromethyl)nicotinate

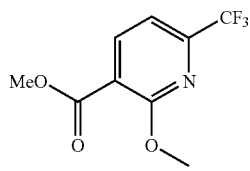

To a stirring solution of 2-hydroxy-6-(trifluoromethyl)nicotinic acid (2.07 g, 10 mmol) in anhydrous DMF (15 mL) at room temperature was added iodomethane (3.1 mL, 50 mmol), followed by anhydrous $K_2CO_3$ (4.15 g, 30 mmol). The resulting suspension was stirred at 70° C. for 2 h. Analysis by HPLC/MS indicated the starting acid had been consumed. After cooling to room temperature, the reaction mixture was diluted with water and extracted with EtOAc (50 mL×3). The combined EtOAc extracts were washed with saturated aqueous NaCl, dried ($Na_2SO_4$), filtered, and concentrated under reduced pressure. The crude product was purified using a silica gel cartridge (40 g) eluted with a gradient of ethyl acetate (0-100%) in hexanes to afford 950 mg (40%) of the title compound. HPLC/MS: retention time=3.17 min, $[M+H]^+$=236.3.

B. Preparation of 2-methoxy-6-(trifluoromethyl)pyridin-3-yl)methanol

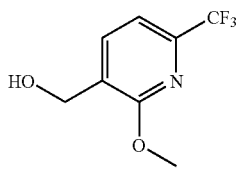

To a stirring solution of methyl 2-methoxy-6-(trifluoromethyl)nicotinate (950 mg, 4.04 mmol) in anhydrous THF (5 mL) cooled at 0° C. was slowly added 1.0 M LAH solution in toluene (4.9 mL, 4.90 mmol) over 5 min. The reaction mixture was stirred at room temperature for 16 h, then quenched carefully by addition of water (1 mL), followed by 10% aqueous KOH (1 mL) and water (1 mL). The resulting mixture was stirred at room temperature for 30 min. The obtained white gummy residue was triturated with ether (40 mL), then the ether layer was decanted. Trituration with ether was repeated three more times. The combined ether extracts were concentrated under reduced pressure. The crude product was purified using a silica gel cartridge (40 g) eluted with a gradient of ether (0-10%) in dichloromethane to afford 800 mg (96%) of the title compound as a colorless oil. HPLC/MS: retention time=2.84 min, $[M+H]^+$=208.3.

C. Preparation of 3-(chloromethyl)-2-methoxy-6-(trifluoromethyl)pyridine

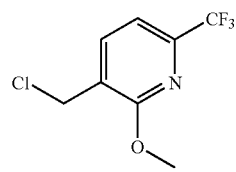

To a stirring solution of 2-methoxy-6-(trifluoromethyl)pyridin-3-yl)methanol (414 mg, 2.0 mmol) in anhydrous $CH_2Cl_2$ (5 mL) at room temperature was added dropwise thionyl chloride (0.44 mL, 6.0 mmol). The resulting mixture was stirred at room temperature for 30 min. Additional thionyl chloride (0.22 mL, 3.0 mmol) was added, then the reaction mixture was stirred at 40° C. for 6 h. After cooling to room temperature, the reaction mixture was concentrated under reduced pressure. The residue was dissolved in $CH_2Cl_2$ (50 mL), washed with saturated aqueous $NaHCO_3$, then saturated aqueous NaCl, dried ($Na_2SO_4$), filtered and concentrated under reduced pressure. The crude product was purified using a silica gel cartridge (40 g) eluted with dichloromethane to afford 360 mg (80%) of the title compound as a colorless oil. HPLC/MS: retention time=3.58 min, $[M+H]^+$=226.3.

Preparation of Reagent 2-chloro-3-(chloromethyl)-6-(trifluoromethyl)pyridine

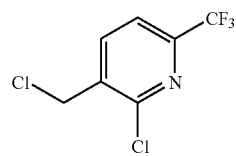

A. Preparation of 2-chloro-6-(trifluoromethyl)pyridin-3-yl)methanol

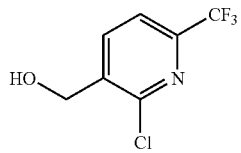

To a stirring solution of 2-chloro-6-(trifluoromethyl)nicotinic acid (790 mg, 3.5 mmol) in anhydrous THF (5 mL) at room temperature was added 1.0 M borane solution in THF (5.25 mL, 5.25 mmol) over 5 min. The resulting mixture was stirred at room temperature for 16 h. Analysis by HPLC/MS indicated that starting acid had been consumed. The reaction mixture was carefully quenched by slow addition of methanol (1 mL). The resulting mixture was stirred at room temperature for 30 min, then diluted with water and extracted with ether (50 mL×2). The combined ether extracts were washed with saturated aqueous NaCl, dried (Na$_2$SO$_4$), filtered and concentrated under reduced pressure. The crude product was purified using a silica gel cartridge (40 g) eluted with a gradient of EtOAc (0-70%) in hexanes to afford 700 mg (96%) of the title compound as a colorless oil. HPLC/MS: retention time=2.31 min, [M+H]$^+$=212.0.

B. Preparation of 2-chloro-3-(chloromethyl)-6-(trifluoromethyl)pyridine

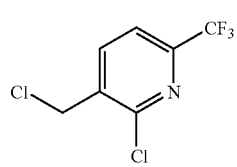

To a stirring solution of 2-chloro-6-(trifluoromethyl)pyridin-3-yl)methanol (0.71 g, 3.36 mmol) in anhydrous CH$_2$Cl$_2$ (5 mL) at room temperature was added dropwise thionyl chloride (0.74 mL, 10.08 mmol). The mixture was stirred at room temperature for 16 h. Analysis by HPLC/MS indicated that the reaction was not complete. The reaction mixture was concentrated under reduced pressure. To the residue was added fresh thionyl chloride (5 mL of 2 M SOCl$_2$ in CH$_2$Cl$_2$). The reaction mixture was stirred at room temperature for 2 days, then concentrated under reduced pressure to afford the crude product as a colorless oil, which was used for the next reaction without further purification.

Preparation of Reagent 3-(hydroxymethyl)-2-methyl-6-(trifluoromethyl)pyridine 1-oxide

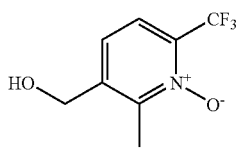

To a stirring solution of (2-methyl-6-(trifluoromethyl)pyridin-3-yl)methanol (2.70 g, 14.1 mmol) in acetonitrile (20 mL) at room temperature was added dropwise a solution of 3-chloroperoxybenzoic acid (77% pure, 3.8 g, 16.9 mmol) in acetonitrile. The reaction mixture was stirred at room temperature for 16 h before concentration under reduced pressure. The residue was diluted with EtOAc, and the EtOAc solution was washed with 5% aqueous Na$_2$S$_2$O$_3$, water, then saturated aqueous NaCl, dried over Na$_2$SO$_4$ and concentrated under reduced pressure. The crude product was purified using a silica gel cartridge (40 g) eluted with a gradient of EtOAc (30-100%) in hexanes to afford 730 mg (25%) of the title compound as a white solid. HPLC/MS: retention time=0.92 min, [M+H]$^+$=208.0. In addition, (2-methyl-6-(trifluoromethyl)pyridin-3-yl)methanol (1.90 g) was recovered.

Preparation of Reagent 3-(bromomethyl)-2-methyl-6-(trifluoromethyl)pyridine 1-oxide

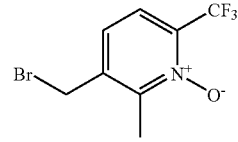

To a stirring solution of 3-(hydroxymethyl)-2-methyl-6-(trifluoromethyl)pyridine 1-oxide (207 mg, 1.0 mmol) and carbon tetrabromide (400 mg, 1.2 mmol) in CH$_2$Cl$_2$ (5 mL) at 0° C. was added Ph$_3$P (393 mg, 1.5 mmol) in small portions over 5 min. The reaction mixture was then stirred at 0° C. for 30 min. Analysis by HPLC/MS indicated the reaction was complete. The reaction mixture was directly loaded onto a silica gel cartridge (40 g) and eluted with a gradient of EtOAc (0-100%) in hexanes to afford 202 mg (75%) of the title compound as a white solid. HPLC/MS: retention time=2.10 min, [M+H]$^+$=269.9.

Preparation of Reagent 3-(6-(chloromethyl)pyridin-3-yl)isoxazole

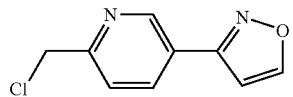

A. Preparation of (6-methylpyridin-3-yl)methanol

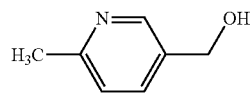

To a solution of lithium aluminum hydride (1 M in diethyl ether, 80 mL, 80 mmol) in 20 mL THF at −78° C. under argon, a solution of methyl 6-methylnicotinate (6.05 g, 40 mmol) in 60 mL diethyl ether was added over 1 h. The resulting reaction mixture was stirred at −78° C. for 1 h before 12 mL EtOAc was added over 10 min. The reaction mixture was allowed to warm up to 0° C. and 12 mL water was added drop-wise over 10 min. The resulting mixture was stirred for 30 min, then filtered through Celite. The filtrate was dried (Na$_2$SO$_4$), filtered and concentrated to obtain 3.07 g (62%) of the title compound as an off-white solid. HPLC: retention time=0.19 min.

B. Preparation of 6-methylnicotinaldehyde

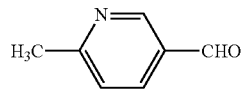

To a solution of oxalyl chloride (2 M in dichloromethane, 9.34 mL, 18.68 mmol) in 30 mL dichloromethane at −60° C. under argon, dimethyl sulfoxide (3.1 g, 2.81 mL, 39.63 mmol) was added over 20 min. The mixture was stirred at −60° C. for 20 min before a solution of (6-methylpyridin-3-yl)methanol in 8 mL dichloromethane was added over 20 min. The reaction mixture was stirred for 20 min, and then triethylamine (8.02 g, 11.05 mL, 79.25 mmol) was added over 10 min. The reaction mixture was allowed to warm up to room temperature and 48 mL water was added. The mixture was extracted with dichloromethane and the combined extracts were dried (Na$_2$SO$_4$), filtered and concentrated. The crude product was purified by automated silica gel chromatography (eluted with ethyl acetate-hexanes) to isolate 1.67 g (85%) of the title compound as a light brown oil. HPLC: retention time=0.19 min.

C. Preparation of 6-methylnicotinaldehyde oxime

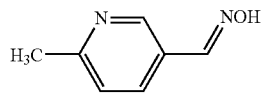

To a solution of 6-methylnicotinaldehyde (1.67 g, 13.79 mmol) in 27.6 mL MeOH, hydroxylamine (50% weight in water, 0.87 mL, 14.2 mmol) was added. The reaction mixture was stirred at room temperature for 2 h and then at 40° C. for an additional 2 h. The reaction mixture was concentrated to obtain 1.76 g (94%) of the title compound as a light brown solid. HPLC: retention time=0.20 min.

D. Preparation of N-hydroxy-6-methylnicotinimidoyl chloride

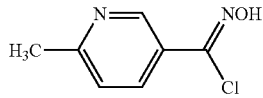

To a stirring mixture of 6-methylnicotinaldehyde oxime (500 mg, 3.67 mmol) in 4 mL DMF at room temperature, was added N-chlorosuccinimide (490 mg, 3.67 mmol) in roughly one tenth portions over 5 min. Additional N-chlorosuccinimide (175 mg, 1.31 mmol) was added after about 4 h. After a total of 6 h, the reaction mixture was diluted with EtOAc, washed with water, saturated aqueous NaCl, dried (Na$_2$SO$_4$) and filtered. The filtrate was passed through a short silica gel column eluted with EtOAc. The eluant was concentrated under vacuum to provide the title compound as a light brown solid. All of this was used in the next step without further purification. HPLC: retention time=0.44 min.

E. Preparation of 3-(6-methylpyridin-3-yl)isoxazole

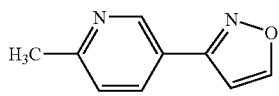

To crude N-hydroxy-6-methylnicotinimidoyl chloride in 10 mL toluene was added vinyl bromide (1 M in THF, 11 mL, 11.0 mmol), followed by bis(tributyltin)oxide (2.12 g, 1.87 mL, 3.67 mmol). The reaction mixture was stirred at room temperature for 5 h and then concentrated. The crude product was purified by automated silica gel chromatography (eluted with ethyl acetate-hexanes) to isolate 155 mg (26%, for two steps) of the title compound as a white solid. HPLC/MS: retention time=0.39 min, [M+H]$^+$=161.

F. Preparation of 3-(6-(chloromethyl)pyridin-3-yl)isoxazole

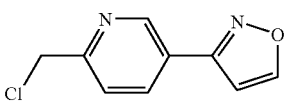

To a stirring mixture of 3-(6-methylpyridin-3-yl)isoxazole (76 mg, 0.474 mmol) and 6 mL carbon tetrachloride, was added N-chlorosuccinimide (69.7 mg, 0.52 mmol), followed by 3 mg benzoyl peroxide. The reaction mixture was refluxed. Additional N-chlorosuccinimide (40 mg, 0.30 mmol) was added in two portions after stirring 2 h and 4 h. After refluxing for a total of 13 h the reaction mixture was diluted with EtOAc, then washed sequentially with 1 N aq. NaOH solution, water and saturated aqueous NaCl. The organic phase was dried (Na$_2$SO$_4$), filtered and concentrated under reduced pressure. The crude product was purified by automated silica gel chromatography (eluted with ethyl acetate-hexanes) to isolate 31 mg (34%) of the title compound as a white solid. HPLC/MS: retention time=1.77 min, [M+H]$^+$=195.

Preparation of Reagent
2-(4-(bromomethyl)phenyl)propan-2-ol

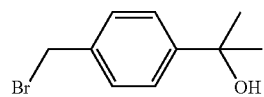

To a stirring solution of 2-p-tolylpropan-2-ol (500 mg, 3.3 mmol) in carbon tetrachloride at room temperature under argon was added N-bromosuccinimide (590 mg, 3.3 mmol), followed by benzoyl peroxide (16 mg, 0.06 mmol). The reaction mixture was stirred at reflux for 4 h. The reaction mixture was concentrated under reduced pressure to obtain a colorless gum. EtOAc (20 mL) and water (20 mL) were added and the layers were separated. The organic layer was dried (MgSO$_4$), filtered and concentrated under vacuum to obtain crude product, which was purified by chromatography (silica gel column eluted with 30% EtOAc/hexanes) to isolate 620 mg of the title compound as a colorless gum. HPLC/MS: retention time=2.908 min, [M+H−H$_2$O]$^+$=211.

Preparation of Reagent
5-chloro-2-(chloromethyl)pyridine

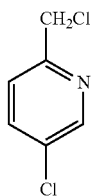

A. Preparation of methyl 5-chloropicolinate

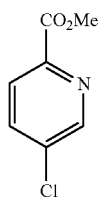

A mixture of 5-chloropicolinonitrile (4 g, 28.87 mmol), concentrated aq. HCl (10 mL) and concentrated $H_2SO_4$ (5 mL) in methanol (30 mL) was stirred at reflux for 35 h under argon. The reaction mixture was concentrated and then carefully diluted with water (50 mL). The pH was adjusted to 6-7 with 20% aqueous NaOH solution. The product was extracted with EtOAc (3×20 mL). The combined organic phase was washed with saturated aqueous NaCl, dried ($MgSO_4$), filtered and concentrated under vacuum to obtain 4.9 g of the title compound as a white solid. HPLC/MS: retention time=1.977 min, $[M+H]^+=172$.

B. Preparation of (5-chloropyridin-2-yl)methanol

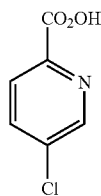

To a stirring solution of methyl 5-chloropicolinate (1 g, 5.8 mmol) in methanol at room temperature under argon was added sodium borohydride (440 mg, 11.57 mmol). The reaction mixture was allowed to stir at room temperature for 1 h. The reaction mixture was concentrated under vacuum to obtain a gum. Water (15 mL) and EtOAc (30 mL) were added and the layers were separated. The organic layer was washed with saturated aqueous NaCl, dried ($MgSO_4$), filtered, and concentrated under reduced pressure to obtain 840 mg of the title compound as colorless gum. HPLC/MS: retention time=0.755 min, $[M+H]^+=144$.

C. Preparation of 5-chloro-2-(chloromethyl)pyridine

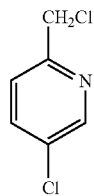

To a stirring solution of (5-chloropyridin-2-yl)methanol (840 mg, 5.8 mmol) in dichloromethane (10 mL) at 0° C. under argon was added thionyl chloride (0.64 mL, 8.77 mmol), followed by 4 drops of DMF (white precipitate formed). The reaction mixture was allowed to stir at room temperature for 1 h. The reaction mixture was concentrated to a white solid. The solid thus obtained was cooled in an ice bath before EtOAc (20 mL) and water (20 mL) and then 10% aqueous $Na_2CO_3$ solution (20 mL) were added. The organic layer was separated, washed with saturated aqueous NaCl, dried ($MgSO_4$), filtered and concentrated to obtain 840 mg of the title compound as a light brown gum. HPLC/MS: retention time=2.392 min, $[M+H]^+=162$.

Preparation of Reagent
1-(chloromethyl)-4-(ethylsulfonyl)benzene

A. Preparation of 4-(ethylsulfonyl)benzoic acid

To a stirring solution of 4-(ethylthio)benzoic acid (1 g, 5.5 mmol) in methanol (30 mL) at 0° C. under argon was added a solution of potassium peroxymonosulfate (6.8 g, 11 mmol) in water (30 mL). The resulted suspension was stirred at room temperature for 15 h. Methanol was evaporated under vacuum, the reaction mixture was diluted with water (30 mL), and the product was extracted with EtOAc (2×30 mL). The combined organic phase was washed with saturated aqueous NaCl, dried ($MgSO_4$), filtered and concentrated under reduced pressure to obtain 910 mg of title compound as a white solid. HPLC/MS: retention time=1.695 min, $[M+H]^+=215$.

B. Preparation of (4-(ethylsulfonyl)phenyl)methanol

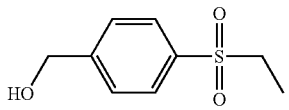

To a stirring solution of 4-(ethylsulfonyl)benzoic acid (500 mg, 2.33 mmol) in THF (5 mL) at 0° C. under argon was added 1 M borane in THF solution (3.5 mL, 3.5 mmol). The reaction mixture was stirred at 70° C. for 20 min. The reaction mixture was then cooled to room temperature, and the THF was removed under reduced pressure. The residue thus obtained was diluted with methanol (5 mL) and stirred for 5 min. Methanol was then removed under reduced pressure. This process was repeated two more times to ensure complete methanolysis of any borane complex. After residual solvent removal under vacuum, 420 mg of the title compound was obtained as a colorless gum. HPLC/MS: retention time=1.373 min, $[M+H]^+=201$.

C. Preparation of 1-(chloromethyl)-4-(ethylsulfonyl)benzene

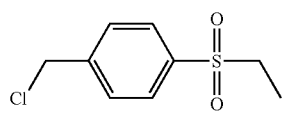

A mixture of (4-(ethylsulfonyl)phenyl)methanol (200 mg, 1 mmol) and thionyl chloride (3 mL) was stirred at reflux for 4 h. The solvent was removed under reduced pressure to obtain a gum. Dichloromethane (10 mL) was added, and the mixture was stirred for 5 min and then concentrated under vacuum. This process was repeated two more times to ensure complete removal of thionyl chloride. After residual solvent removal under vacuum, 205 mg of the title compound was obtained as a white solid. HPLC/MS: retention time=2.308 min, $[M+H]^+=219$.

The following contemplated examples of compounds of Formula I (Table 1) and compounds of Formula II (Table 2) may be prepared by the methods outlined above.

TABLE 1

I

| Example | $R^1$ | $R^2$ | $R^3$ | $R^4$ |
|---|---|---|---|---|
| 44 | 4-Cl—Ph | pyridin-4-yl | Me | cyclohexylmethyl |
| 45 | 4-Cl—Ph | 4-NC—Ph | Et | 6-$CF_3$-pyridin-3-ylmethyl |
| 46 | pyridin-4-yl | 4-Cl—Ph | 6-$CF_3$-pyridin-3-yl-methyl | cyano |
| 47 | pyridin-4-yl | 4-Cl—Ph | 6-$CF_3$-pyridin-3-yl-methyl | MeO |
| 48 | pyridin-4-yl | 4-Cl—Ph | 4-$CF_3$-benzyl | H |
| 49 | 4-Cl—Ph | 4-Cl—Ph | 6-$CF_3$-pyridin-3-yl-methyl | H |
| 50 | pyridin-3-yl-oxy | 4-Cl—Ph | 6-$CF_3$-2-Me-pyridin-3-ylmethyl | H |
| 51 | 1-imidazolyl | 4-Cl—Ph | 4-$CF_3$-benzyl | H |
| 52 | 3-HO-pyrrolidin-1-yl | 2-Cl—Ph | 4-$CF_3$-benzyl | H |
| 53 | 4-Cl—Ph | 4-Cl—Ph | Me | benzyl |
| 54 | 4-Cl—Ph | pyridin-4-yl | Me | PhO |
| 55 | 4-Cl—Ph | pyridin-4-yl | Me | PhHN |

TABLE 2

II

| Example | $R^1$ | $R^2$ | $R^3$ | $R^5$ |
|---|---|---|---|---|
| 56 | pyridin-4-yl | 4-Cl—Ph | 6-$CF_3$-pyridin-3-ylmethyl | H |
| 57 | pyridin-4-yl | 4-Cl—Ph | 4-$CF_3$-benzyl | Me |
| 58 | 4-Cl—Ph | 4-Cl—Ph | 4-$CF_3$-benzyl | Me |
| 59 | H | 4-Cl—Ph | 6-$CF_3$-pyridin-3-ylmethyl | 2-Cl—Ph |

BIOLOGICAL EVALUATION

Cannabinoid Receptor Binding Assay

Radioligand binding studies were conducted in membranes prepared from Chinese Hamster Ovary (CHO) cells that over-express recombinant human CB-1 (CHO-CB-1 cells). Total assay volume for the binding studies was 100 μL. 5 μg of membranes were brought up to a final volume of 95 μl with Binding Buffer (25 mM HEPES, 150 mM NaCl, 2.5 mM $CaCl_2$, 1 mM $MgCl_2$, 0.25% BSA). The diluted membranes were preincubated with a compound or DMSO vehicle. The binding reaction was initiated by the addition of 2 nM final $^3$H-CP-55,940 (120 Ci/mmol) and proceeded for 2.5 hours at room temperature. The binding reaction was terminated by transferring the reaction to GF/B 96 well plates (presoaked with 0.3% polyethylenimine) using a Packard Cell Harvester. The filter was washed with 0.25x PBS, 30 µL MICROSCINT scintillation fluid was added per well, and the bound radiolabel was quantitated by scintillation counting on a Packard TOPCOUNT Scintillation Counter. The CB-2 radioligand binding assay was conducted identically except that the membranes from CHO-CB-2 cells were used.

For a compound to be considered a CB-1 antagonist, the compound must possess a CB-1 receptor binding affinity Ki less than 13000 nM. As determined by the assay described above, the CB-1 receptor binding Ki values of the working Examples fall within the range of 0.01 nM to 10000 nM.

Cannabinoid Receptor Functional Activity Assay

Functional CB-1 inverse agonist activity of test compounds was determined in CHO—CB-1 cells using a cAMP accumulation assay. CHO—CB-1 cells were grown in 96 well plates to near confluence. On the day of the functional assay, growth medium was aspirated and 100 of Assay Buffer (PBS plus 25 mM HEPES/0.1 mM 3-isobutyl-1-methylxanthine/0.1% BSA) was added. Compounds were added to the Assay buffer diluted 1:100 from 100% DMSO and allowed to preincubate for 10 min prior to addition of 5 uM forskolin. The mixture was allowed to proceed for 15 min at room temperature and was terminated by the addition of 0.1 N HCl. The total intracellular cAMP concentration was quantitated using the Amersham cAMP SPA kit.

UTILITIES AND COMBINATIONS

Utilities

The compounds of the present invention are cannabinoid receptor modulators, and include compounds which are, for example, selective agonists, partial agonists, inverse agonists, antagonists or partial antagonists of the cannabinoid receptor. Accordingly, the compounds of the present invention may be useful for the treatment or prevention of diseases and disorders associated with G-protein coupled cannabinoid receptor activity. Preferably, compounds of the present invention possess activity as antagonists or inverse agonists of the CB-1 receptor, and may be used in the treatment of diseases or disorders associated with the activity of the CB-1 receptor.

Accordingly, the compounds of the present invention can be administered to mammals, preferably humans, for the treatment of a variety of conditions and disorders, including, but not limited to metabolic and eating disorders as well as conditions associated with metabolic disorders, (e.g., obesity, diabetes, arteriosclerosis, hypertension, polycystic ovary disease, cardiovascular disease, osteoarthritis, dermatological disorders, hypertension, insulin resistance, hypercholesterolemia, hypertriglyceridemia, cholelithiasis and sleep disorders, hyperlipidemic conditions, bulimia nervosa and compulsive eating disorders) or psychiatric disorders, such as substance abuse, depression, anxiety, mania and schizophrenia. These compounds could also be used for the improvement of cognitive function (e.g., the treatment of dementia, including Alzheimer's disease, short term memory loss and attention deficit disorders); neurodegenerative disorders (e.g., Parkinson's Disease, cerebral apoplexy and craniocerebral trauma) and hypotension (e.g., hemorrhagic and endotoxin-induced hypotension). These compounds could also be used for treatment of catabolism in connection with pulmonary dysfunction and ventilator dependency; treatment of cardiac dysfunction (e.g., associated with valvular disease, myocardial infarction, cardiac hypertrophy or congestive heart failure); and improvement of the overall pulmonary function; transplant rejection; rheumatoid arthritis; multiple sclerosis; inflammatory bowel disease; lupus; graft vs. host disease; T-cell mediated hypersensitivity disease; psoriasis; asthma; Hashimoto's thyroiditis; Guillain-Barre syndrome; cancer; contact dermatitis; allergic rhinitis; and ischemic or reperfusion injury.

Compounds useful in the treatment of appetitive or motivational disorders regulate desires to consume sugars, carbohydrates, alcohol or drugs and more generally to regulate the consumption of ingredients with hedonic value. In the present description and in the claims, appetitive disorders are understood as meaning: disorders associated with a substance and especially abuse of a substance and/or dependency on a substance, disorders of eating behaviors, especially those liable to cause excess weight, irrespective of its origin, for example: bulimia nervosa, craving for sugars. The present invention therefore further relates to the use of a CB-1 receptor antagonist or inverse agonist for the treatment of bulimia and obesity, including obesity associated with type II diabetes (non-insulin-dependent diabetes), or more generally any disease resulting in the patient becoming overweight. Obesity, as described herein, is defined by a body mass index (kg/m$^2$) of at least 26. It may be due to any cause, whether genetic or environmental, including overeating and bulemia, polycycstic ovary disease, craniopharyngeoma, Prader-Willi Syndrome, Frohlich's Syndrome, Type II diabetes, growth hormone deficiency, Turner's Syndrome and other pathological states characterized by reduced metabolic activity or reduced energy expenditure. As used with reference to the utilities described herein, the term "treating" or "treatment" encompasses prevention, partial alleviation, or cure of the disease or disorder. Further, treatment of obesity is expected to prevent progression of medical covariants of obesity, such as arteriosclerosis, Type II diabetes, polycystic ovary disease, cardiovascular disease, osteoarthritis, dermatological disorders, hypertension, insulin resistance, hypercholesterolemia, hypertriglyceridemia, cholelithiasis and sleep disorders.

Compounds in the present invention may also be useful in treating substance abuse disorders, including substance dependence or abuse without physiological dependence. Substances of abuse include alcohol, amphetamines (or amphetamine-like substances), caffeine, cannabis, cocaine, hallucinogens, inhalants, nicotine, opioids, phencyclidine (or phencyclidine-like compounds), sedative-hypnotics or benzodiazepines, and other (or unknown) substances and combinations of the above. The terms "substance abuse disorders" also includes drug or alcohol withdrawal syndromes and substance-induced anxiety or mood disorder with onset during withdrawal.

Compounds in the present invention may be useful in treating memory impairment and cognitive disorders. The condition of memory impairment is manifested by impairment of the ability to learn new information and/or the inability to recall previously learned information. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, HIV, cardiovascular disease, and head trauma as well as age-related cognitive decline. Dementias are diseases that include memory loss and additional intellectual impairment separate from memory.

Cannabinoid receptor modulators may also be useful in treating cognitive impairments related to attentional deficits, such as attention deficit disorder.

Compounds in the present invention may also be useful in treating diseases associated with dysfunction of brain dopaminergic systems, such as Parkinson's Disease and substance abuse disorders. Parkinsons's Disease is a neurodenerative movement disorder characterized by bradykinesia and tremor.

As modulators of the cannabinoid receptor, the compounds of the present invention are further useful for the treatment and prevention of respiratory diseases and disorders. Respiratory diseases for which cannabinoid receptor modulators are useful include, but are not limited to, chronic pulmonary obstructive disorder, emphysema, asthma, and bronchitis. In addition, cannabinoid receptor modulators block the activation of lung epithelial cells by moeties such as allergic agents, inflammatory cytokines or smoke, thereby limiting release of mucin, cytokines, and chemokines, or selectively inhibiting lung epithelial cell activation.

Moreover, the compounds employed in the present invention may stimulate inhibitory pathways in cells, particularly in leukocytes, lung epithelial cells, or both, and are thus useful in treating such diseases. "Leukocyte activation" is defined herein as any or all of cell proliferation, cytokine production, adhesion protein expression, and production of inflammatory mediators. "Epithelial cell activation" is defined herein as the production of any or all of mucins, cytokines, chemokines, and adhesion protein expression.

Use of the compounds of the present invention for treating leukocyte activation-associated disorders is exemplified by, but is not limited to, treating a range of disorders such as: transplant (such as organ transplant, acute transplant, xenotransplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; respiratory and pulmonary diseases including but not limited to chronic obstructive pulmonary disease (COPD), emphysema, bronchitis, and acute respiratory distress syndrome (ARDS); inflammatory bowel disease, including ulcerative colitis and Crohn's disease; lupus (systemic lupus erythematosis); graft vs. host disease; T-cell mediated hypersensitivity diseases, including contact hypersensitivity, delayed-type hypersensitivity, and gluten-sensitive enteropathy (Celiac disease); psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; glomerulonephritis; serum sickness; uticaria; allergic diseases such as respiratory allergies (asthma, hayfever, allergic rhinitis) or skin allergies; scleracierma; mycosis fungoides; acute inflammatory and respiratory responses (such as acute respiratory distress syndrome and ishchemia/reperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schlerosis; and morphea. The term "leukocyte activation-associated" or "leukocyte-activation mediated" disease as used herein includes each of the above referenced diseases or disorders. In a particular embodiment, the compounds of the present invention are useful for treating the aforementioned exemplary disorders irrespective of their etiology. The combined activity of the present compounds towards monocytes, macrophages, T-cells, etc. may be useful in treating any of the above-mentioned disorders.

Cannabinoid receptors are important in the regulation of Fc gamma receptor responses of monocytes and macrophages. Compounds of the present invention inhibit the Fc gamma dependent production of TNF alpha in human monocytes/macrophages. The ability to inhibit Fc gamma receptor dependent monocyte and macrophage responses results in additional anti-inflammatory activity for the present compounds. This activity is especially of value, for example, in treating inflammatory diseases such as arthritis or inflammatory bowel disease. In particular, the present compounds are useful for treating autoimmune glomerulonephritis and other instances of glomerulonephritis induced by deposition of immune complexes in the kidney that trigger Fc gamma receptor responses leading to kidney damage.

Cannabinoid receptors are expressed on lung epithelial cells. These cells are responsible for the secretion of mucins and inflammatory cytokines/chemokines in the lung and are thus intricately involved in the generation and progression of respiratory diseases. Cannabinoid receptor modulators regulate both the spontaneous and the stimulated production of both mucins and cytokines. Thus, such compounds are useful in treating respiratory and pulmonary diseases including, COPD, ARDS, and bronchitis.

Further, cannabinoid receptors may be expressed on gut epithelial cells and hence regulate cytokine and mucin production and may be of clinical use in treating inflammatory diseases related to the gut. Cannabinoid receptors are also expressed on lymphocytes, a subset of leukocytes. Thus, cannabinoid receptor modulators will inhibit B and T-cell activation, proliferation and differentiation. Thus, such compounds will be useful in treating autoimmune diseases that involve either antibody or cell mediated responses such as multiple sclerosis and lupus.

In addition, cannabinoid receptors regulate the Fc epsilon receptor and chemokine induced degranulation of mast cells and basophils. These play important roles in asthma, allergic rhinitis, and other allergic disease. Fc epsilon receptors are stimulated by IgE-antigen complexes. Compounds of the present invention inhibit the Fc epsilon induced degranulation responses, including the basophil cell line, RBL. The ability to inhibit Fc epsilon receptor dependent mast cell and basophil responses results in additional anti-inflammatory and anti-allergic activity for the present compounds. In particular, the present compounds are useful for treating asthma, allergic rhinitis, and other instances of allergic disease.

Combinations

The present invention includes within its scope pharmaceutical compositions comprising, as an active ingredient, a therapeutically effective amount of at least one of the compounds of Formula I or II, alone or in combination with a pharmaceutical carrier or diluent. Optionally, compounds of the present invention can be used alone, in combination with other suitable therapeutic agents useful in the treatment of the aforementioned disorders including: anti-obesity agents; anti-diabetic agents, appetite suppressants; cholesterol/lipid-lowering agents, HDL-raising agents, cognition enhancing agents, agents used to treat neurodegeneration, agents used to treat respiratory conditions, agents used to treat bowel disorders, anti-inflammatory agents; anti-anxiety agents; anti-depressants; anti-hypertensive agents; cardiac glycosides; and anti-tumor agents.

Such other therapeutic agent(s) may be administered prior to, simultaneously with, or following the administration of the cannabinoid receptor modulators in accordance with the invention.

Examples of suitable anti-obesity agents for use in combination with the compounds of the present invention include melanocortin receptor (MC4R) agonists, melanin-concentrating hormone receptor (MCHR) antagonists, growth hormone secretagogue receptor (GHSR) antagonists, galanin receptor modulators, orexin antagonists, CCK agonists, GLP-1 agonists, and other Pre-proglucagon-derived peptides; NPY1 or NPY5 antagonsist, NPY2 and NPY4 modulators, corticotropin releasing factor agonists, histamine receptor-3 (H3) modulators, aP2 inhibitors, PPAR gamma modulators, PPAR delta modulators, acetyl-CoA carboxylase (ACC) inihibitors, 11-β-HSD-1inhibitors, adinopectin receptor modulators; beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a thyroid receptor beta modulator, such as a thyroid receptor ligand as disclosed in WO 97/21993 (U. Cal SF), WO 99/00353 (KaroBjo) and GB98/284425 (KaroBio), a lipase inhibitor, such as orlistat or ATL-962 (ALIZYME), serotonin receptor agonists, (e.g., BVT-933 (BIOVITRUM)), monoamine reuptake inhibitors or releasing agents, such as fenfluramine, dexfenfluramine, fluvoxamine, fluoxetine, paroxetine, sertraline, chiorphentermine, cloforex, clortermine, picilorex, sibutramine, dexamphetamine, phentermine, phenyipropanolamine or mazindol, anorectic agents such as topiramate (Johnson & Johnson), CNTF (ciliary neurotrophic factor)/AXOKINE® (Regeneron), BDNF (brain-derived neurotrophic factor), leptin and leptin receptor modulators, or cannabinoid-1 receptor antagonists, such as SR-141716 (Sanofi) or SLV-319 (Solvay).

Examples of suitable anti-diabetic agents for use in combination with the compounds of the present invention include: insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, PPAR α/γ dual agonists, 11-β—HSD-1 inhibitors, dipeptidyl peptidase IV (DP4) inhibitors, SGLT2 inhibitors, glycogen phosphorylase inhibitors, and/or meglitinides, as well as insulin, and/or glucagon-like peptide-1 (GLP-1), GLP-1 agonist, and/or a PTP-1B inhibitor (protein tyrosine phosphatase-1B inhibitor).

The antidiabetic agent may be an oral antihyperglycemic agent preferably a biguanide such as metformin or phenformin or salts thereof, preferably metformin HCl. Where the antidiabetic agent is a biguanide, the compounds of the present invention will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the beta-cells, with glyburide and glipizide being preferred, which may be administered in the same or in separate oral dosage forms. The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of the present invention may be employed in combination with a PPAR Y agonist such as a thiazolidinedione oral anti-diabetic agent or other insulin sensitizers (which has an insulin sensitivity effect in NIDDM patients) such as rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of the present invention may be employed with a PPARα/γ dual agonist such as MK-767/KRP-297 (Merck/Kyorin; as described in, K. Yajima, et. al., Am. J. Physiol. Endocrinol. Metab., 284: E966-E971 (2003)), AZ-242 (tesaglitazar; Astra-Zeneca; as described in B. Ljung, et. al., J. Lipid Res., 43, 1855-1863 (2002)); muraglitazar; or the compounds described in U.S. Pat. No. 6,414,002.

The compounds of the present invention may be employed in combination with anti-hyperlipidemia agents, or agents used to treat arteriosclerosis. An example of an hypolipidemic agent would be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pitavastatin (Nissan/Sankyo's nisvastatin (NK-104) or itavastatin), disclosed in U.S. Pat. No. 5,011,930, Shionogi-Astra/Zeneca rosuvastatin (visastatin (ZD-4522)) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. No. 4,686,237, octahydronaphthalenes such as disclosed in U.S. Pat. No. 4,499,289, keto analogs of mevinolin (lovastatin) as disclosed in European Patent Application No. 0,142,146 A2, and quinoline and pyridine derivatives disclosed in U.S. Pat. Nos. 5,506,219 and 5,691,322. In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller, et al., J. Med. Chem., 31, 1869-1871 (1998) including isoprenoid (phosphinyl-methyl)phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., *Current Pharmaceutical Design*, 2, 1-40 (1996).

In addition, other squalene synthetase inhibitors suitable for use herein include the terpenoid pyrophosphates disclosed by P. Ortiz de Montellano, et al., *J. Med. Chem.,* 20, 243-249 (1977), the farnesyl diphosphate analog A and presqualene pyrophosphate (PSQ-PP) analogs as disclosed by Corey and Volante, *J. Am. Chem. Soc.,* 98, 1291-1293 (1976), phosphinylphosphonates reported by McClard, R. W. et al., *J. Am. Chem. Soc.,* 109, 5544 (1987) and cyclopropanes reported by Capson, T. L., PhD dissertation, June, 1987, Dept. Med. Chem. U of Utah, Abstract, Table of Contents, pp 16, 17, 40-43, 48-51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (SECHOLEX, POLICEXIDE) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The other hypolipidemic agent may be an ACAT inhibitor (which also has anti-atherosclerosis activity) such as disclosed in, *Drugs of the Future,* 24, 9-15 (1999), (Avasimibe); "The ACAT inhibitor, C1-1011 is effective in the prevention and regression of aortic fatty streak area in hamsters", Nicolosi et al., *Atherosclerosis* (Shannon, Irel), 137 (1), 77-85 (1998); "The pharmacological profile of FCE 27677: a novel ACAT inhibitor with potent hypolipidemic activity mediated by selective suppression of the hepatic secretion of ApoB100-containing lipoprotein", Ghiselli, Giancarlo, *Cardiovasc. Drug Rev.,* 16 (1), 16-30 (1998); "RP 73163: abioavailable alkylsulfinyl-diphenylimidazole ACAT inhibitor", Smith, C., et al., *Bioorg. Med. Chem. Lett,* 6 (1), 47-50 (1996); "ACAT inhibitors: physiologic mechanisms for hypolipidemic and anti-atherosclerotic activities in experimental animals", Krause et al., Editor(s): Ruffolo, Robert R., Jr.; Hollinger, Mannfred A., *Inflammation: Mediators Pathways,* 173-98 (1995), Publisher: CRC, Boca Raton, Fla.; "ACAT inhibitors: potential anti-atherosclerotic agents", Sliskovic et al., *Curr. Med. Chem.,* 1 (3), 204-25 (1994); "Inhibitors of acyl-CoA: cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)-methyl]ureas with enhanced hypocholesterolemic activity", Stout et al., *Chemtracts: Org. Chem.,* 8 (6), 359-62 (1995), or TS-962 (Taisho Pharmaceutical Co. Ltd), as well as F-1394, CS-505, F-12511, HL-004, K-10085 and YIC—C8-434.

The hypolipidemic agent may be an upregulator of LDL receptor activity such as MD-700 (Taisho Pharmaceutical Co. Ltd) and LY295427 (Eli Lilly). The hypolipidemic agent may be a cholesterol absorption inhibitor preferably Schering-Plough's SCH48461 (ezetimibe) as well as those disclosed in Atherosclerosis 115, 45-63 (1995) and *J. Med. Chem.* 41, 973 (1998).

The other lipid agent or lipid-modulating agent may be a cholesteryl transfer protein inhibitor (CETP) such as Pfizer's CP-529,414 as well as those disclosed in WO/0038722 and in EP 818448 (Bayer) and EP 992496, and Pharmacia's SC-744 and SC-795, as well as CETi-1 and JTT-705.

The hypolipidemic agent may be an ileal $Na^+$/bile acid cotransporter inhibitor such as disclosed in Drugs of the Future, 24, 425-430 (1999). The ATP citrate lyase inhibitor which may be employed in the combination of the invention may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 2000/015201; a beta-lactam cholesterol absorption inhibitor such as disclosed in EP 675714; an HDL upregulator such as an LXR agonist, a PPAR α-agonist and/or an FXR agonist; an LDL catabolism promoter such as disclosed in EP 1022272; a sodium-proton exchange inhibitor such as disclosed in DE 19622222; an LDL-receptor inducer or a steroidal glycoside such as disclosed in U.S. Pat. No. 5,698,527 and GB 2304106; an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B12 and Vitamin E; isoniazid as disclosed in WO 97/35576; a cholesterol absorption inhibitor, an HMG-CoA synthase inhibitor, or a lanosterol demethylase inhibitor as disclosed in WO 97/48701; a PPAR δ agonist for treating dyslipidemia; or a sterol regulating element binding protein-I (SREBP-1) as disclosed in WO 2000/050574, for example, a sphingolipid, such as ceramide, or neutral sphingomyelenase (N-SMase) or fragment thereof. Preferred hypolipidemic agents are pravastatin, lovastatin, simvastatin, atorvastatin, fluvastatin, pitavastatin and rosuvastatin, as well as niacin and/or cholestagel.

The compounds of the present invention may be employed in combination with anti-hypertensive agents. Examples of suitable anti-hypertensive agents for use in combination with the compounds of the present invention include beta adrenergic blockers, calcium channel blockers (L-type and/or T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043, 265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Cannbinoid receptor modulators could be useful in treating other diseases associated with obesity, including sleep disorders. Therefore, the compounds described in the present invention could be used in combination with therapeutics for treating sleep disorders. Examples of suitable therapies for treatment of sleeping disorders for use in combination with the compounds of the present invention include melatonin analogs, melatonin receptor antagonists, ML 1B agonists, GABA receptor modulators; NMDA receptor modulators, histamine-3 (H3) receptor modulators, dopamine agonists and orexin receptor modulators.

Cannabinoid receptor modulators may reduce or ameliorate substance abuse or addictive disorders. Therefore, combination of cannabinoid receptor modulators with agents used to treat addictive disorders may reduce the dose requirement or improve the efficacy of current addictive disorder therapeutics. Examples of agents used to treat substance abuse or addictive disorders are: selective serotonin reuptake inhibitors (SSRI), methadone, buprenorphine, nicotine and bupropion.

Cannabinoid receptor modulators may reduce anxiety or depression; therefore, the compounds described in this application may be used in combination with anti-anxiety agents or antidepressants. Examples of suitable anti-anxiety agents for use in combination with the compounds of the present invention include benzodiazepines (e.g., diazepam, lorazepam, oxazepam, alprazolam, chlordiazepoxide, clonazepam, chlorazepate, halazepam and prazepam), 5HT1A receptor agonists (e.g., buspirone, flesinoxan, gepirone and ipsapirone), and corticotropin releasing factor (CRF) antagonists.

Examples of suitable classes of anti-depressants for use in combination with the compounds of the present invention include norepinephrine reuptake inhibitors (tertiary and secondary amine tricyclics), selective serotonin reuptake inhibitors (SSRIs) (fluoxetine, fluvoxamine, paroxetine and sertraline), monoamine oxidase inhibitors (MAOIs) (isocarboxazid, phenelzine, tranylcypromine, selegiline), reversible inhibitors of monoamine oxidase (RIMAs) (moclobemide), serotonin and norepinephrine reuptake inhibitors (SNRIs) (venlafaxine), corticotropin releasing factor (CRF) receptor antagonists, alpah-adrenoreceptor antagonists, and atypical antidepressants (bupropion, lithium, nefazodone, trazodone and viloxazine).

The combination of a conventional antipsychotic drug with a CB-1 receptor antagonist could also enhance symptom reduction in the treatment of psychosis or mania. Further, such a combination could enable rapid symptom reduction, reducing the need for chronic treatment with antipsychotic agents. Such a combination could also reduce the effective antipsychotic dose requirement, resulting in reduced probability of developing the motor dysfunction typical of chronic antipsychotic treatment.

Examples of suitable antipsychotic agents for use in combination with the compounds of the present invention include the phenothiazine (chlorpromazine, mesoridazine, thioridazine, acetophenazine, fluphenazine, perphenazine and trifluoperazine), thioxanthine (chlorprothixene, thiothixene), heterocyclic dibenzazepine (clozapine, olanzepine and aripiprazole), butyrophenone (haloperidol), dipheyylbutylpiperidine (pimozide) and indolone (molindone) classes of antipsychotic agents. Other antipsychotic agents with potential therapeutic value in combination with the compounds in the present invention include loxapine, sulpiride and risperidone.

Combination of the compounds in the present invention with conventional antipsychotic drugs could also provide an enhanced therapeutic effect for the treatment of schizophrenic disorders, as described above for manic disorders. As used here, schizophrenic disorders include paranoid, disorganized, catatonic, undifferentiated and residual schizophrenia, schizophreniform disorder, schizoaffective disorder, delusional disorder, brief psychotic disorder and psychotic disorder not specified. Examples of suitable antipsychotic drugs for combination with the compounds in the present invention include the antipsychotics mentioned above, as well as dopamine receptor antagonists, muscarinic receptor agonists, 5HT2A receptor antagonists and 5HT2A/dopamine receptor antagonists or partial agonists (e.g., olanzepine, aripiprazole, risperidone, ziprasidone).

The compounds described in the present invention could be used to enhance the effects of agents used in the treatment of Parkinson's Disease. Examples of agents used to treat Parkinson's Disease include: levadopa with or without a COMT inhibitor, antiglutamatergic drugs (amantadine, riluzole), alpha-2 adrenergic antagonists such as idazoxan, opiate antagonists, such as naltrexone, other dopamine agonists or transportor modulators, such as ropinirole, or pramipexole or neurotrophic factors such as glial derived neurotrophic factor (GDNF).

The compounds described in the present invention could be used in combination with suitable anti-inflammatory agents. Examples of suitable anti- inflammatory agents for use in combination with the compounds of the present invention include prednisone, dexamethasone, cyclooxygenase inhibitors (i.e., COX-1 and/or COX- 2 inhibitors such as NSAIDs, aspirin, indomethacin, ibuprofen, piroxicam, NAPROXEN®, CELEBREX®, VIOXX®), CTLA4-Ig agonists/antagonists, CD40 ligand antagonists, IMPDH inhibitors, such as mycophenolate (CELLCEPT®), integrin antagonists, alpha-4 beta-7 , integrin antagonists, cell adhesion inhibitors, interferon gamma antagonists, ICAM-1,tumor necrosis factor (TNF) antagonists (e.g., infliximab, OR1384, including TNF-alpha inhibitors, such as tenidap, anti-TNF antibodies or soluble TNF receptor such as etanercept (ENBREL®), rapamycin (sirolimus or RAPAMUNE) and leflunomide (ARAVA)), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., ZELNORM® and MAXI-K® openers such as those disclosed in U.S. Pat. No. 6,184,231 B1).

Exemplary of such other therapeutic agents which may be used in combination with cannabinoid receptor modulators include the following: cyclosporins (e.g., cyclosporin A), anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), gold compounds, antiproliferative agents such as methotrexate, FK506 (tacrolimus, PROGRAF), mycophenolate mofetil, cytotoxic drugs such as azathiprine and cyclophosphamide, anticytokines such as antilL-4 or IL-4 receptor fusion proteins and PDE 4 inhibitors such as ARIFLO, and the PTK inhibitors disclosed in the following U.S. patent applications Ser. Nos., incorporated herein by reference in their entirety: U.S.Ser. No. 09/097,338, filed Jun. 15, 1998; U.S.Ser. No. 09/094,797, filed Jun. 15, 1998; U.S.Ser. No. 09/173,413, filed Oct. 15, 1998; and U.S.Ser. No. 09/262,525, filed Mar. 4, 1999. See also the following documents and references cited therein and incorporated herein by reference: Hollenbaugh, D., et al., "Cleavable CD40Ig Fusion Proteins and the Binding to Sgp39", *J.*

*Immunol. Methods* (Netherlands), 188 (1), pp. 1-7 (Dec. 15, 1995); Hollenbaugh, D., et al., "The Human T Cell Antigen Gp39, A Member of the TNF Gene Family, Is a Ligand for the CD40 Receptor: Expression of a Soluble Form of Gp39 with B Cell Co-Stimulatory Activity", EMBO J(England), 11 (12), pp. 4313-4321 (Dec. 1992); and Moreland, L. W. et al., "Treatment of Rheumatoid Artbritis with a Recombinant Human Tumor Necrosis Factor Receptor (P75)-Fc Fusion Protein, "*New England J. of Medicine,* 337 (3), pp. 141-147 (1997).

The above other therapeutic agents, when employed in combination with the compounds of the present invention, may be used, for example, in those amounts indicated in the Physicians' Desk Reference (PDR) or as otherwise determined by one of ordinary skill in the art.

The compounds of Formulas I and II of the invention can be administered orally or parenterally, such as subcutaneously or intravenously, as well as by nasal application, rectally or sublingually to various mammalian species known to be subject to such maladies, e.g., humans, in an effective amount up to 1 gram, preferably up to 200 mg, more preferably to 50 mg in a regimen of single, two or four divided daily doses.

The compounds of the Formulas I and II can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of Formulas I and II can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or CREMAPHOR.

Exemplary compositions for rectal administration include suppositories which can contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as PLASTIBASE (mineral oil gelled with polyethylene).

It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

It should be understood that while this invention has been described herein in terms of specific embodiments set forth in detail, such embodiments are presented by way of illustration of the general principles of the invention, and the invention is not necessarily limited thereto. Certain modifications and variations in any given material, process step or chemical formula will be readily apparent to those skilled in the art without departing from the true spirit and scope of the present invention, and all such modifications and variations should be considered within the scope of the claims that follow.

What is claimed is:
1. A compound according to Formula I

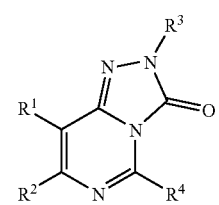

or a pharmaceutically acceptable salt or a stereoisomer thereof
wherein
$R^1$ is selected from the group consisting of phenyl and pyridyl which may each be optionally substituted with 1 to 3 members selected from the group consisting of halogen, cyano, alkyl and hydroxyalkyl;

$R^2$ is phenyl which may be optionally substituted with 1 to 3 halogen;

$R^3$ is an alkyl which may be optionally substituted with 1 to 3 $R^{10}$;

$R^4$ is selected from the group consisting of hydrogen, halogen, cyano, alkyl, alkoxy, —S—$CH_3$, $NH_2$, $NHCH_3$, $NCH(CH_3)_2$,

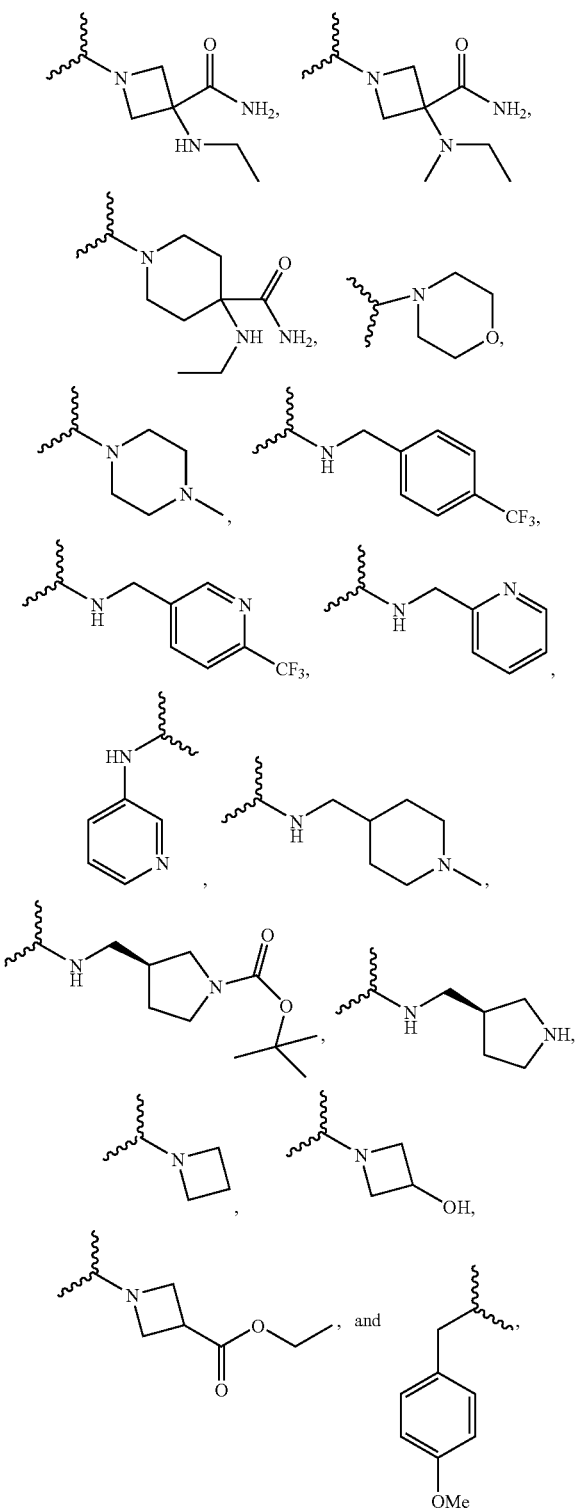
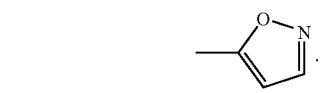
$R^{10}$ in each instance is independently selected from the group consisting of alkyl, phenyl, pyridyl, halogen, and cyano, wherein the alkyl, phenyl and pyridyl may each be optionally substituted with 1 to 3 members selected from the group consisting of halogen, cyano, hydroxyl, carboxyl, $CF_3$, and
2. A compound is selected from the group consisting of:
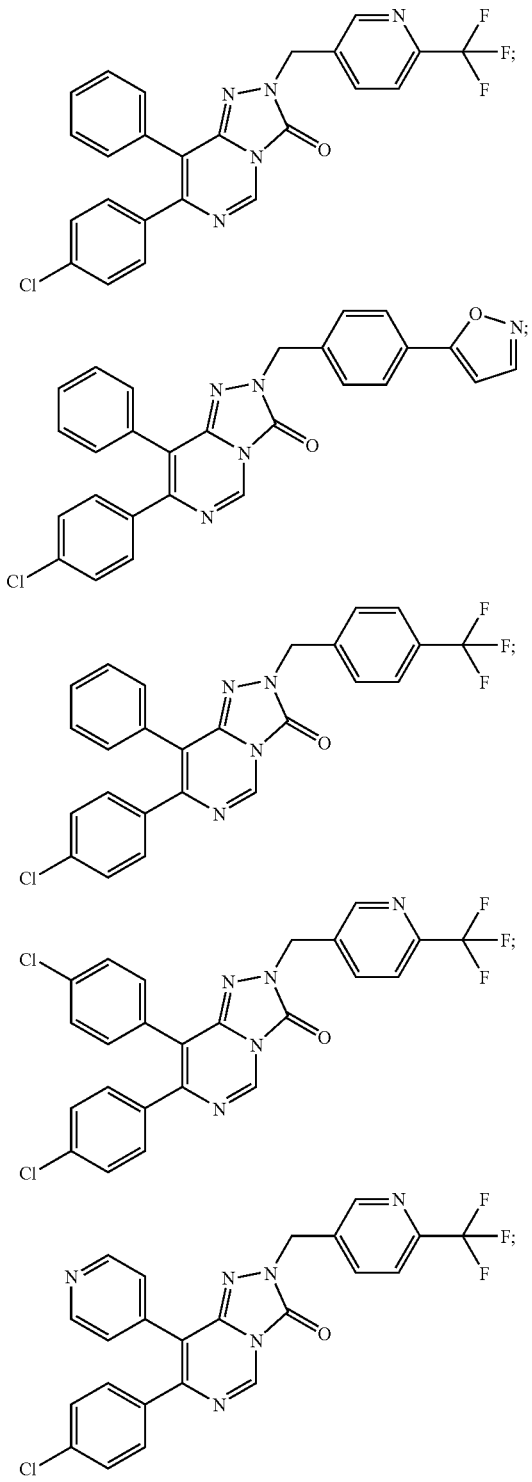

109
-continued
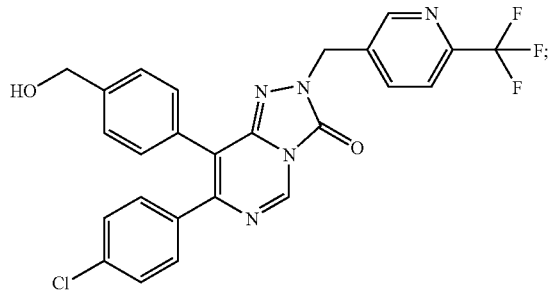
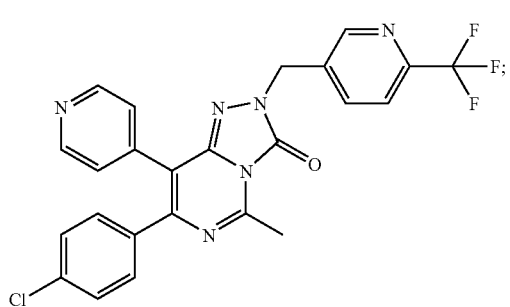
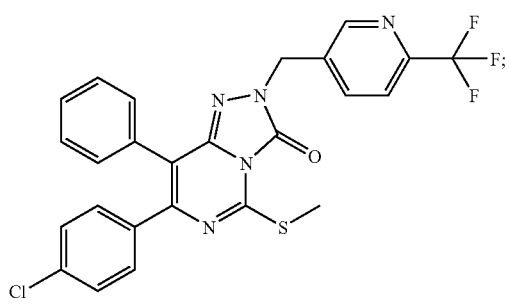
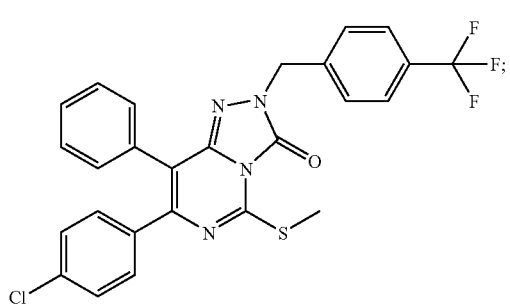
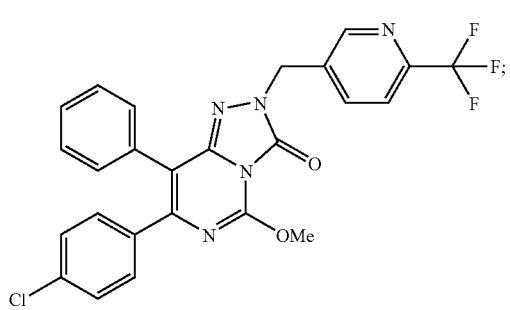
110
-continued
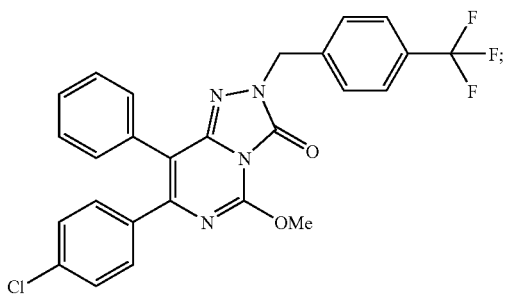
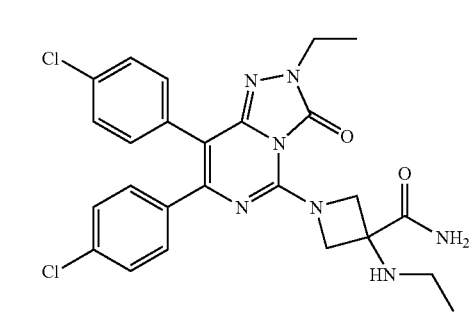
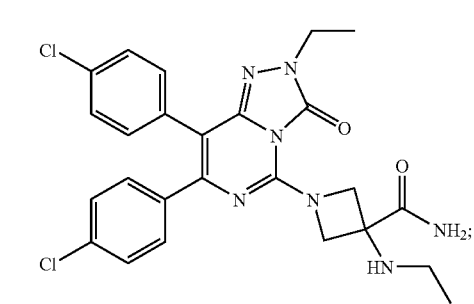
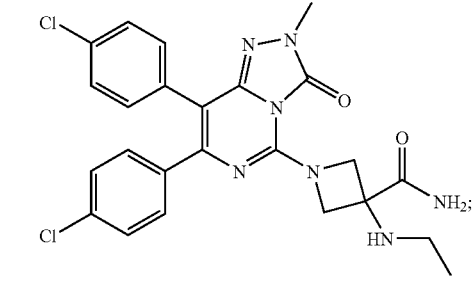
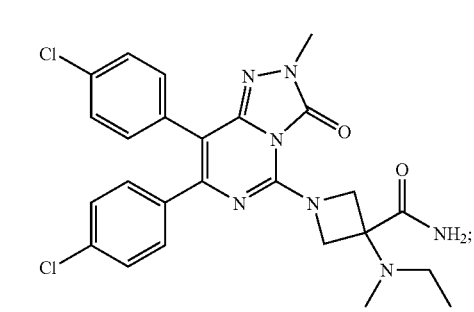

-continued
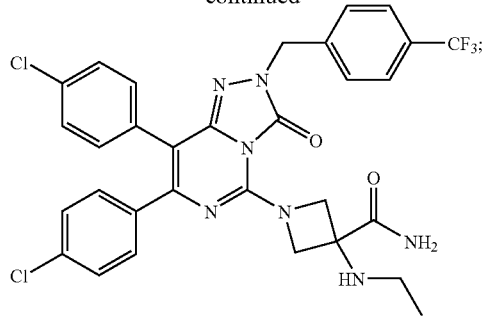
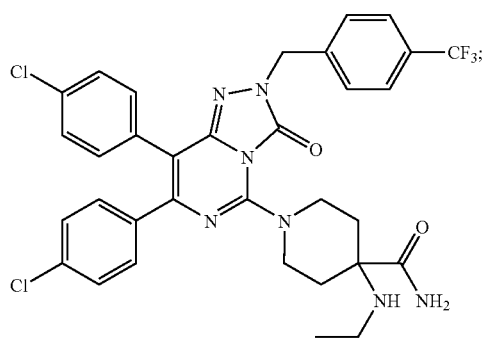
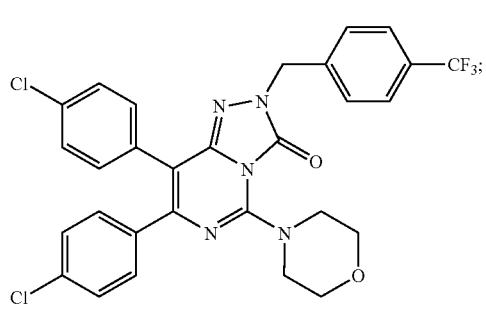
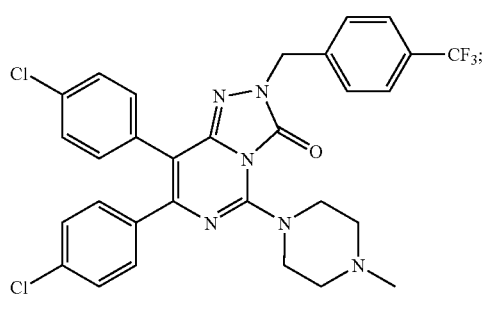
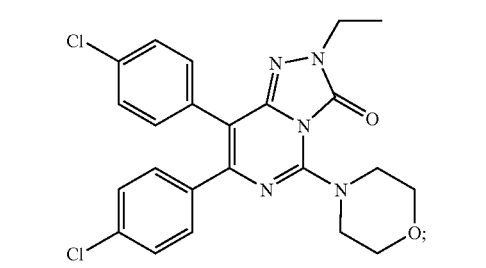
-continued
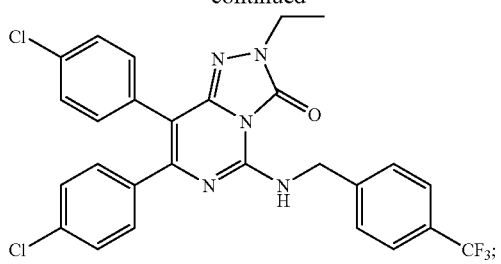
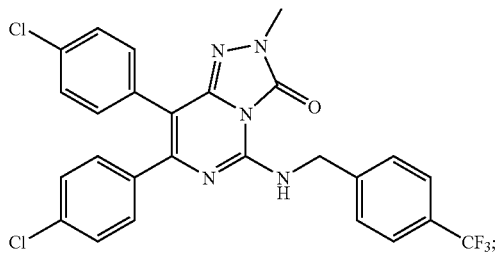
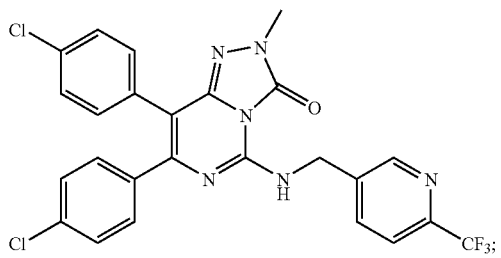
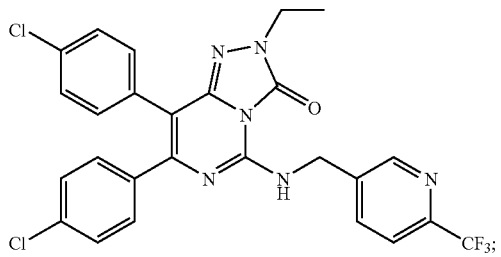
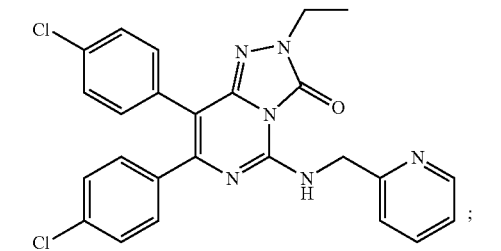

-continued
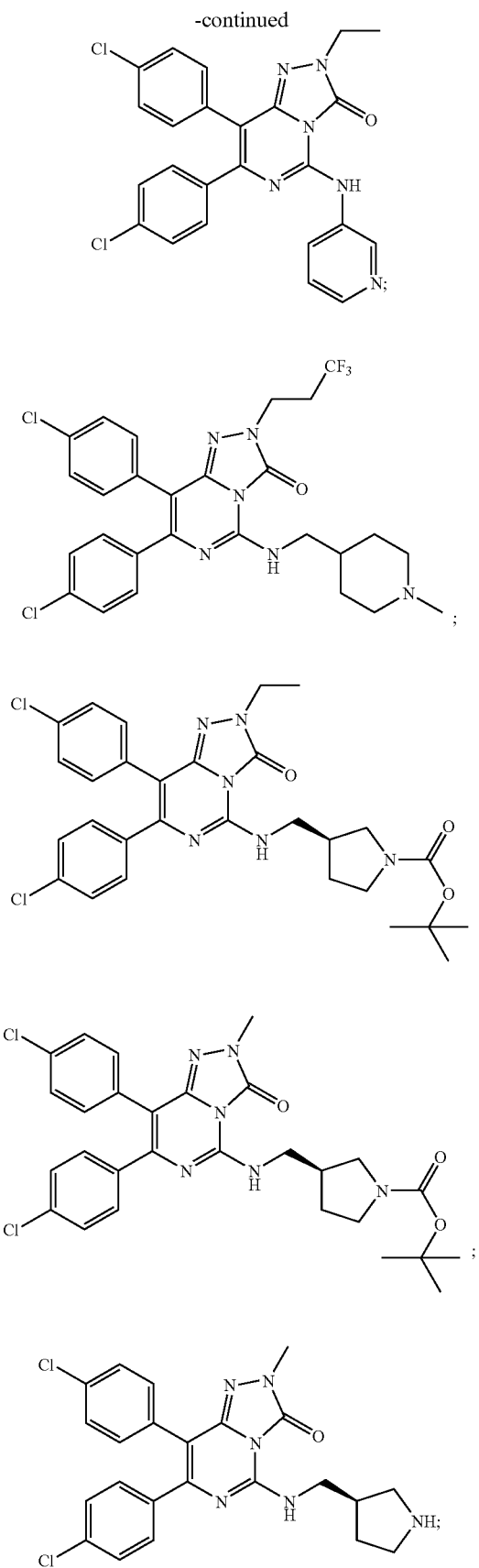
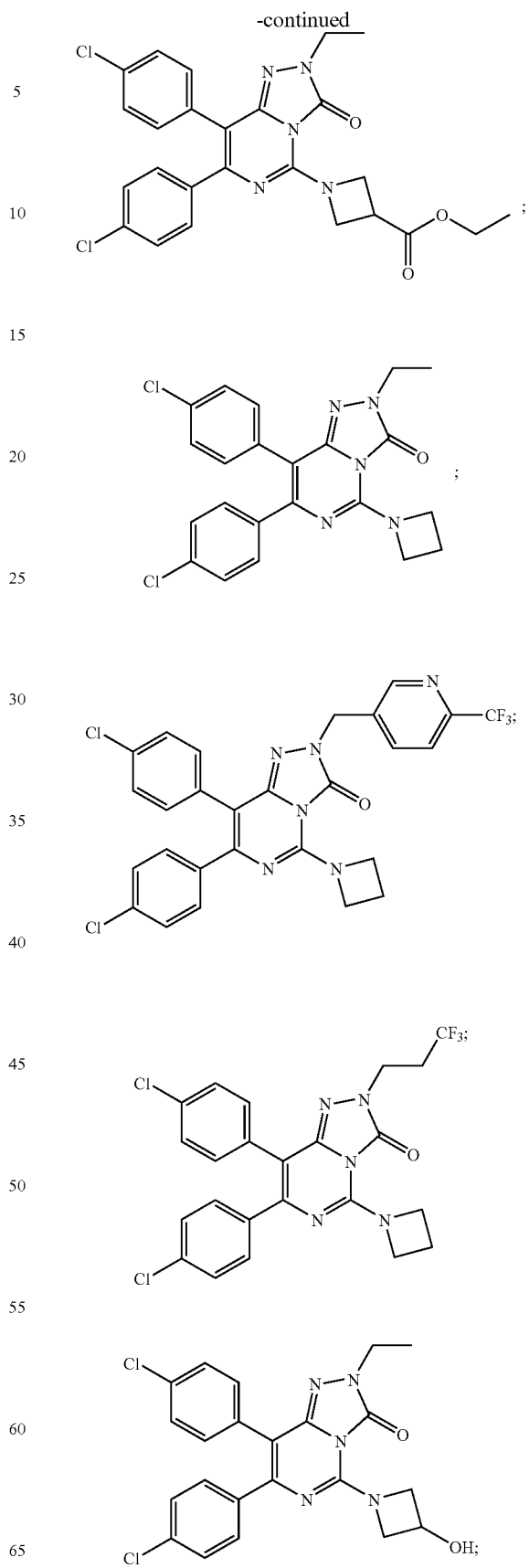

-continued
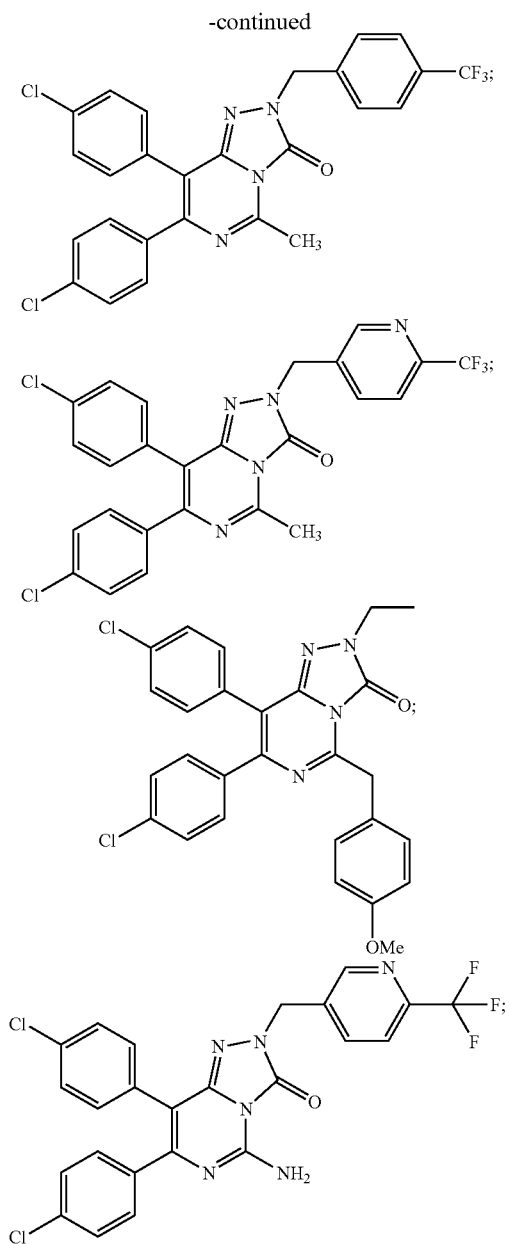
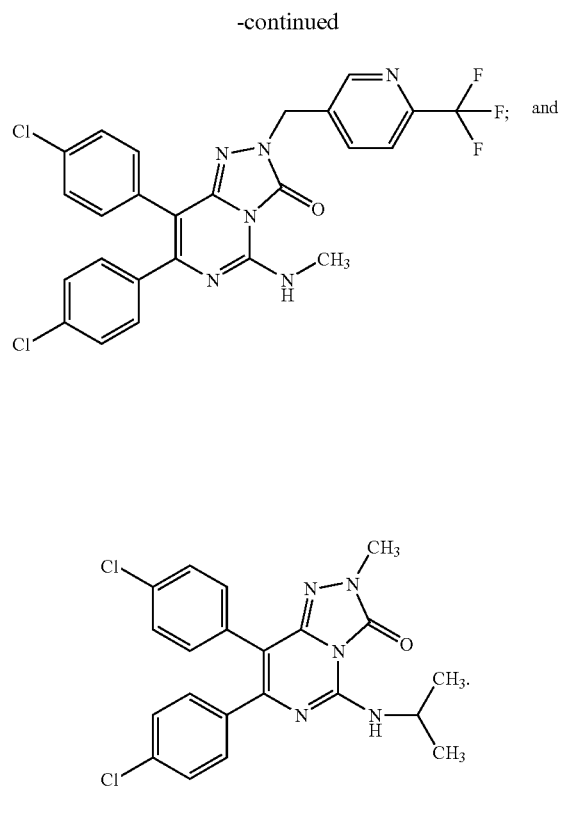
3. A pharmaceutical composition, comprising a compound according to claim 1
and
at least one pharmaceutically acceptable carrier or diluent.
* * * * *

UNITED STATES PATENT AND TRADEMARK OFFICE
CERTIFICATE OF CORRECTION

PATENT NO. : 7,452,892 B2  
APPLICATION NO. : 11/455083  
DATED : November 18, 2008  
INVENTOR(S) : Gang Wu et al.

Page 1 of 2

It is certified that error appears in the above-identified patent and that said Letters Patent is hereby corrected as shown below:

In the Claims:

Claim 1:

Column 107, line 52, after " 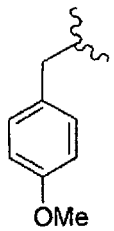 ", change "," to -- ; --.

Claim 2:

Column 108, line 8, after "compound", delete "is".

Column 110, line 24, after " 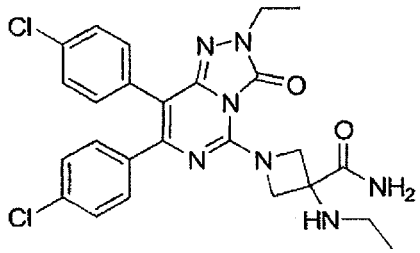 ", insert -- ; --.

Signed and Sealed this  
Fifth Day of July, 2011

David J. Kappos  
*Director of the United States Patent and Trademark Office*

CERTIFICATE OF CORRECTION (continued)
U.S. Pat. No. 7,452,892 B2

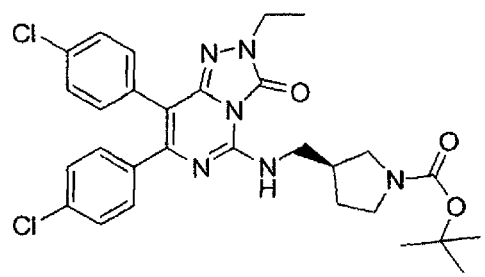

Column 113, line 35, after " ", insert -- ; --.